United States Patent
Mazhari et al.

(10) Patent No.: US 11,479,542 B2
(45) Date of Patent: Oct. 25, 2022

(54) COMPOUNDS, COMPOSITIONS AND METHODS

(71) Applicants: CERECOR, INC., Rockvill, MD (US); MERCK SHARP & DOHME CORP., Rahway, NJ (US)

(72) Inventors: Reza Mazhari, Towson, MD (US); Djelila Mezaache, Stone Ridge, VA (US); Blake M. Paterson, Baltimore, MD (US); James Vornov, Pikesville, MD (US); Rachel M. Garner, Baltimore, MD (US); Todd Nelson, Cream Ridge, NJ (US)

(73) Assignees: CERECOR, INC., Rockvill, MD (US); MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/884,848

(22) Filed: May 27, 2020

(65) Prior Publication Data

US 2021/0107892 A1 Apr. 15, 2021

Related U.S. Application Data

(63) Continuation of application No. 16/272,788, filed on Feb. 11, 2019, now Pat. No. 10,710,976, which is a continuation of application No. 15/538,015, filed as application No. PCT/US2015/066741 on Dec. 18, 2015, now Pat. No. 10,202,363.

(60) Provisional application No. 62/096,077, filed on Dec. 23, 2014.

(51) Int. Cl.

| | |
|---|---|
| *C07D 401/12* | (2006.01) |
| *A61P 5/24* | (2006.01) |
| *A61P 9/00* | (2006.01) |
| *A61P 9/10* | (2006.01) |
| *A61P 11/14* | (2006.01) |
| *A61P 15/00* | (2006.01) |
| *A61P 17/02* | (2006.01) |
| *A61P 25/00* | (2006.01) |
| *A61P 25/04* | (2006.01) |
| *A61P 25/08* | (2006.01) |
| *A61P 25/14* | (2006.01) |
| *A61P 25/16* | (2006.01) |
| *A61P 25/18* | (2006.01) |
| *A61P 25/24* | (2006.01) |
| *A61P 25/28* | (2006.01) |
| *A61P 27/06* | (2006.01) |
| *A61P 27/16* | (2006.01) |
| *A61P 29/02* | (2006.01) |
| *A61P 43/00* | (2006.01) |

(52) U.S. Cl.
CPC ........ *C07D 401/12* (2013.01); *C07B 2200/13* (2013.01)

(58) Field of Classification Search
CPC ..... C07D 401/12; C07B 2200/13; A61P 5/24; A61P 9/00; A61P 9/10; A61P 11/14; A61P 15/00; A61P 17/02; A61P 25/00; A61P 25/04; A61P 25/08; A61P 25/14; A61P 25/16; A61P 25/18; A61P 25/24; A61P 25/28; A61P 27/06; A61P 27/16; A61P 29/02; A61P 43/00
See application file for complete search history.

(56) References Cited

U.S. PATENT DOCUMENTS 10,202,363 B2 * 2/2019 Mazhari .................. A61P 43/00

FOREIGN PATENT DOCUMENTS

WO WO-2016049048 A1 * 3/2016 ........... A61K 31/451

* cited by examiner

*Primary Examiner* — John M Mauro
(74) *Attorney, Agent, or Firm* — Adler Pollock & Sheehan P.C; Michel Morency

(57) ABSTRACT

The disclosed subject matter provides certain polymorphic forms of Compound (I) as well as pharmaceutical compositions comprising Compound (I) or such polymorphic forms, and methods of using or making such compounds and pharmaceutical compositions. It has now been discovered that Compound (I) can exist in multiple crystalline forms (polymorphs). One particular crystalline form, Form II, has been found to be more thermodynamically stable and, thus, likely more suitable for bulk preparation and handling than other polymorphic forms. Efficient and economic methods have been developed to prepare Compound (I) and Form II in high purity on a large scale. In animal studies, Form II has demonstrated safety and efficacy in treating depressive disorders and, when micronized, improved absorption compared to non-micronized Form II.

(I)

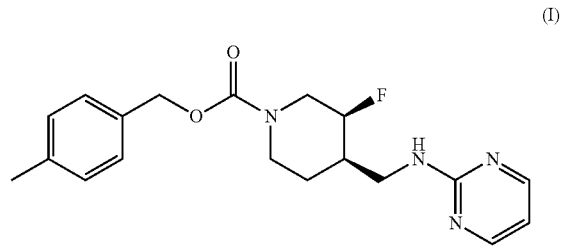

12 Claims, 11 Drawing Sheets

COMPOUNDS, COMPOSITIONS AND METHODS

CROSS-REFERENCE TO RELATED APPLICATIONS

This application claims benefit under 35 U.S.C. § 119(e) of U.S. Provisional Application Ser. No. 62/096,077, filed Dec. 23, 2014, which is hereby incorporated by reference.

BACKGROUND

U.S. Pat. No. 7,592,360 (issued Sep. 22, 2009) discloses Compound (I):

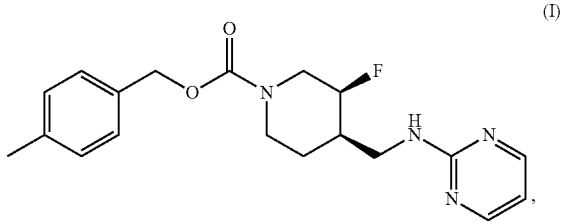 [SMILES: Cc1ccc(COC(=O)N2CC[C@H](CNc3ncccn3)[C@H](F)C2)cc1]

or 4-methylbenzyl (3S, 4R)-3-fluoro-4-[(pyrimidin-2-ylamino) methyl] piperidine-1-carboxylate (referred to in the '360 patent as (3S, 4R)-4-methylbenzyl 3-fluoro-4-[(pyrimidin-2-ylamino)methyl]piperidine-1-carboxylate, and elsewhere as MK-0657 or CERC-301). A potent selective antagonist of N-methyl-D-aspartate receptor subunit 2B (NMDA-GluN2B or NR2B), Compound (I) was initially developed for treatment of Parkinson's disease (Addy et al., *J. Clin. Psychopharmacol.*, 49:856-864 (2009)). A pilot study of Compound (I) in patients with treatment-resistant major depressive disorder (TRMDD) showed antidepressant effects in the 17-item Hamilton Depression Rating Scale (HAM-D17) and Beck Depression Inventory (BDI) (Ibrahim et al., *J. Clin. Psychopharmacol.*, 32(4):551-557 (2012)). Due to the study's small sample size, no definitive conclusions as to Compound (I)'s potential efficacy or safety profile could be drawn from the study's preliminary data.

SUMMARY OF THE DISCLOSURE

The disclosed subject matter provides certain polymorphic forms of Compound (I)

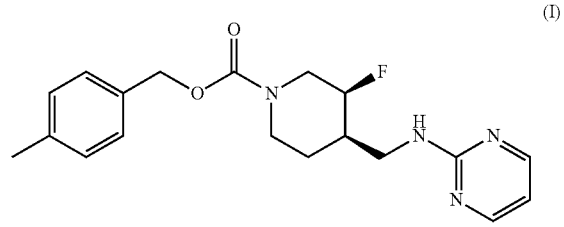 [SMILES: Cc1ccc(COC(=O)N2CC[C@H](CNc3ncccn3)[C@H](F)C2)cc1]

as well as pharmaceutical compositions comprising Compound (I) or such polymorphic forms, and methods of using or making such compounds and pharmaceutical compositions.

It has now been discovered that Compound (I) can exist in multiple crystalline forms (polymorphs). One particular crystalline form, Form II, has been found to be more thermodynamically stable and, thus, likely more suitable for bulk preparation and handling than other polymorphic forms. Efficient and economic methods have been developed to prepare Compound (I) and Form II in high purity on a large scale. In animal studies, Form II has demonstrated safety and efficacy in treating depressive disorders and, when micronized, improved absorption compared to non-micronized Form II.

One aspect of the disclosure provides a compound that is a substantially pure crystalline Form II of Compound (I) exhibiting at least one of:

an X-ray powder diffraction pattern, obtained using copper Kα radiation, comprising peaks of 2-theta angles of about 5.9 and 8.8 degrees;

(ii) an X-ray powder diffraction pattern, obtained using copper Kα radiation, substantially as shown in FIG. 1A;

(iii) an ultraviolet absorbance spectrum, obtained using methanol as diluent, substantially as shown in FIG. 2;

(iv) an infrared spectrum substantially as shown in FIG. 3;

(v) a proton nuclear magnetic resonance spectrum at about 600 MHz in $CD_3CN$ substantially as shown in FIG. 4;

(vi) a $^{13}C$ nuclear magnetic resonance spectrum at about 150 MHz in $CD_3CN$ substantially as shown in FIG. 5;

(vii) a thermogravimetric analysis curve substantially as shown in FIG. 6; and (viii) a differential scanning calorimetry thermogram substantially as shown in FIG. 7.

Also provided herein is a crystalline Form I of Compound (I) as described in FIG. 1B.

Another aspect of the disclosure provides a pharmaceutical composition of the disclosure comprises particles of Compound (I) with an X90 particle size of about 10 μm or less. Suitable particles of Compound (I) include for example microparticles and nanoparticles.

Another aspect of the disclosure provides a method of treating a condition responsive to an NR2B antagonist. The method includes administering to a patient in need thereof an effective amount of a compound or pharmaceutical composition of the present invention.

Another aspect of the disclosure provides a method of treating suicidal ideation, comprising administering Form I or Form II of Compound (I) to a patient who has, is suspected of having, or has been diagnosed with having suicidal ideation.

Another aspect of the disclosure provides a method of targeting N-methyl-D-aspartate (NMDA) receptor subunit 2B (GluN2B) expressed on a cell comprising administering to a patient in need thereof an effective amount of a compound or pharmaceutical composition of the present invention.

Another aspect of the disclosure provides a method of reducing absorption rate of Compound (I) comprising administering to a patient in need thereof an effective amount of the Compound (I) with food, wherein the compound is administered either substantially concurrently with, or up to about 2 hours after, or up to about 30 minutes before administration of food.

Another aspect of the disclosure provides a method of preparing Compound (I), analogs and associated intermediates.

Another aspect of the disclosure provides a method of preparing Compound (I) comprising:
(i) reacting Compound (8)

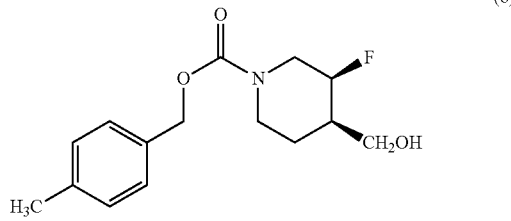

(8)

with triflic anhydride to yield a triflate;
(ii) reacting the triflate with ammonia to yield Compound (9)

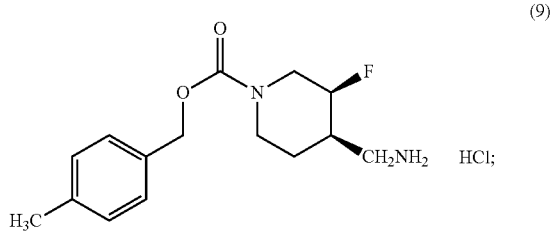

(9)

and
(iii) reacting the Compound (9) with 2-chloropyrimidine to yield Compound (I).

Another aspect of the disclosure provides a method of preparing Form II of Compound (I). By suspending purified Form I of Compound (I) in water for a sufficient period of time or heating solid Form I, conversion to Form II can be readily achieved.

DETAILED DESCRIPTION

Definitions

Figure 1A:
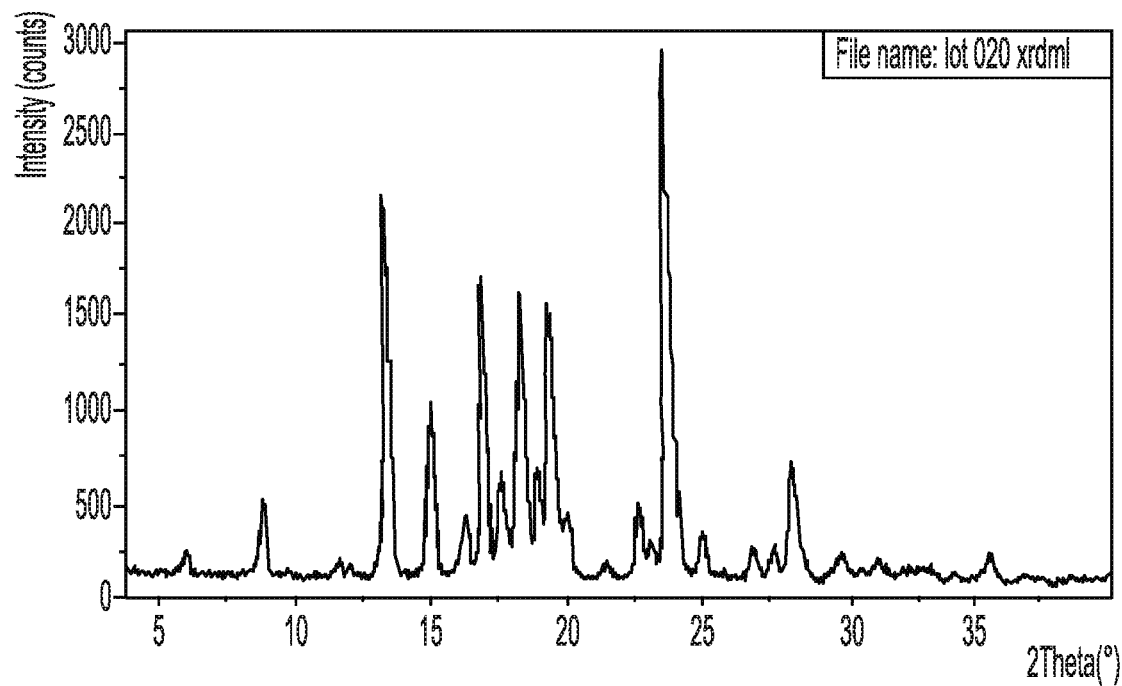
FIG. 1A shows an X-ray powder diffraction pattern of crystalline Form II of Compound (I).

Unless clearly indicated otherwise, the following terms as used herein have the meanings indicated below.

"Micronized" refers to particles with a diameter within the micron range. Methods of producing micronized particles include friction-based techniques, such as milling (e.g., jet-milling) and grinding, and supercritical fluid-based techniques, such as the Rapid Expansion of Supercritical Solutions (RESS), Supercritical Anti-Solvent (SAS), and Particles from Gas Saturated Solutions (PGSS) methods. In some embodiments, the Compound (I) particles are micronized by jet-milling.

"Particle size" refers to the particle dimension of the active pharmaceutical ingredient (API), such as Compound (I) or Form (II) of Compound (I), as ascertained by laser diffraction particle size analysis, performed for example using an analyzer such as Malvern, Sympatec, Microtac or Horibe.

"X90" refers to the particle size corresponding to 90% of the cumulative undersize distribution by volume.

"X50" refers to the particle size corresponding to 50% of the cumulative undersize distribution by volume.

"X10" refers to the particle size corresponding to 10% of the cumulative undersize distribution by volume.

"Mean particle size" or "mean PS" includes D43 particle size.

"D43" refers to the particle size calculated according to the mean diameter over volume or DeBroukere mean.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in *Remington: The Science and Practice of Pharmacy*, 21$^{st}$ Ed. (Lippincott Williams & Wilkins, Baltimore, Md., 2005) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

"Patient" refers to an animal, such as a mammal, including but not limited to, a human. Hence, the methods disclosed herein can be useful in human therapy and veterinary applications. In one embodiment, the patient is a mammal. In another embodiment, the patient is a human.

"Effective amount" or "therapeutically effective amount" refers to an amount of a compound or pharmaceutical composition which, based on its parameters of efficacy and potential for toxicity and the knowledge of one skilled in the art, produces a desired effect, such as treating or preventing a condition. An effective amount can be administered in for example one, two, three, four or more doses per day or per week.

"Treat" or "treating" refers to attain or attaining a beneficial or desired result, such as a clinical result. In some embodiments, the beneficial or desired result is any one or more of the following: inhibiting or suppressing the onset or development of a condition, reducing the severity of the condition, reducing the number or severity of symptoms associated with the condition, increasing the quality of life of a patient suffering from the condition, decreasing the dose of another medication required to treat the condition, enhancing the effect of another medication a patient is taking for the condition, and prolonging the survival of a patient having the condition. For example, in the case of major depressive disorder (MDD), treating may involve a clinically significant decline in at least one measurable marker or symptom of MDD. Measurable markers include electroencephalogram (EEG) slow wave activity (SWA) and brain-derived neurotrophic factor (BDNF). The severity of MDD may be assessed, for example, using the Montgomery-Asberg Depression Rating Scale (MADRS), Hamilton Rating Scale for Depression (HAM-D or HRSD, such as HAM-D17, Beck Depression Inventory (BDI), VAS-depression, Hamilton Anxiety Rating Scale (HAM-A), Brief Psychiatric Rating Scale-positive symptoms (BPRS), the Clinician Administered Dissociative States Scale (CADSS), Young Mania Rating Scale (YMRS), Snaith Hamilton Pleasure Scale-Modified Scoring System (SHAPS-M), Wechsler Depression Rating Scale, Raskin Depression Rating Scale, Inventory of Depressive Symptomatology (IDS), the Quick Inventory of Depressive Symptomatology (QIDS), or any other scale known in the art for rating MDD.

"Prevent" or "preventing" refers to reduce or reducing the probability of that a patient develops a condition which the patient does not have but is at risk of developing. "At risk" denotes that a patient has one or more risk factors, which are measurable parameters that correlate with the development of a condition and are known in the art. A patient having one or more of risk factors has a higher probability of developing the condition than a patient without such risk factors.

"Adjunct" refers to the use of a compound or pharmaceutical composition in conjunction with at least one additional treatment. As an adjunct, the compound or pharmaceutical composition may improve the efficacy of the at least one additional treatment, such as by achieving a faster response to the at least one additional treatment, reducing the severity of a condition, reducing the number or severity of symptoms associated with a condition, or decreasing the dose of the at least one additional treatment. The adjunct may be administered with the at least one additional treatment together in a single composition or separately in individual compositions, at substantially the same time or at different times.

A condition that is "responsive to an NR2B antagonist" includes any condition in which administration of an N-methyl-D-aspartate receptor subunit 2B (NR2B) antagonist treats or prevents the condition, as those terms are defined herein. Hence, a condition whose symptoms are diminished upon administration of an NMDA NR2B antagonist is a condition responsive to an NR2B antagonist. Examples of a condition that is responsive to an NR2B antagonist include Parkinson's disease, neuropathic pain (such as postherpetic neuralgia, nerve injury, "dynias", vulvodynia, phantom limb pain, root avulsions, painful diabetic neuropathy, painful traumatic mononeuropathy, painful polyneuropathy, central pain syndromes, and postsurgical pain syndromes, postmastectomy syndrome, postthoracotomy syndrome, stump pain), bone and joint pain (such as osteoarthritis), repetitive motion pain, dental pain, cancer pain, myofascial pain (muscular injury, fibromyalgia), perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, schizophrenia, stroke, traumatic brain injury, Alzheimer's disease, cerebral ischemia, amyotrophic lateral sclerosis, Huntington's disease, sensorineural hearing loss, tinnitus, glaucoma, neurological damage caused by epileptic seizures or by neurotoxin poisoning or by impairment of glucose and/or oxygen to the brain, vision loss caused by neurodegeneration of the visual pathway, Restless Leg Syndrome, multi-system atrophy, non-vascular headache, chronic (or chronic persistent), subchronic or acute cough, primary hyperalgesia, secondary hyperalgesia, primary allodynia, secondary allodynia, or other pain caused by central sensitization, dyskinesias (such as the side effects accompanying normal doses of L-Dopa), depressive disorders (such as, major depressive disorder (MDD) and treatment-resistant MDD), trauma- and stressor-related disorders (such as acute stress disorder and posttraumatic stress disorder (PTSD)), bipolar disorders with depressive features, anxiety disorders, and obsessive-compulsive and related disorders. See *Diagnostic and Statistical Manual of Mental Disorders*, $5^{th}$ Ed. (American Psychiatric Association, Arlington, Va., 2013) for additional examples of depressive disorders, bipolar disorders, anxiety disorders, obsessive-compulsive and related disorders, and other conditions.

"Anti-hypertensive" refers to any agent that lowers blood pressure. Examples of an anti-hypertensive include calcium channel blockers, angiotensin converting enzyme inhibitors (ACE inhibitors), angiotensin II receptor antagonists (A-II antagonists), diuretics, beta-adrenergic receptor blockers (β-blockers), vasodilators and alpha-adrenergic receptor blockers (α-blockers).

"Administered intermittently" refers to administration at irregular time periods throughout, for example, a 24 hour period, or a 7 day period, or on an as needed basis.

"Reacting" refers to combining or mixing two or more agents under appropriate conditions to produce the indicated or desired product. The indicated or desired product may not necessarily result directly from reacting the agents; reacting the agents may yield one or more intermediates that ultimately lead to the formation of the indicated or desired product.

"Recrystallization" refers to a purification process whereby a solid compound is dissolved in an appropriate solvent and recrystallized to provide a solid of higher purity. Types of recrystallization include single solvent, multi-solvent, hot filtration and seeding.

"Slurrying" refers to a purification process of suspending crystals of a compound in an appropriate solvent, stirring the suspension, and isolating the crystals.

"Such as" has the same meaning as "such as but not limited to." Similarly, "include" has the same meaning as "include but not limited to", while "including" has the same meaning as "including but not limited to".

"Between about X and about Y" refers to values between about X and about Y, including about X and about Y.

Other than in the working examples, or where otherwise indicated, all numbers expressing quantities of ingredients, reaction conditions, and so forth as used in the specification and claims are to be understood as being modified by the term "about". Accordingly, unless indicated to the contrary, such numbers are approximations that may vary depending upon the desired properties sought to be obtained by the disclosed subject matter. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the disclosed subject matter are approximations, the numerical values set forth in the working examples are reported as precisely as possible. Any numerical value, however, inherently contains certain errors necessarily resulting from the standard deviation found in their respective testing measurements.

Compounds

It has been discovered that Compound (I) can exist in multiple crystalline or polymorphic forms. The polymorphic forms of Compound (I) identified to date are: Form I, Form II and Form III. Form I is composed of acicular particles (rods) while Form II has plate-like morphology. Form III has been detected only in polymorphic mixtures. Neither is Compound (I)'s polymorphism nor any of its polymorphic forms disclosed in U.S. Pat. No. 7,592,360.

Form II, the thermodynamically most stable of the three polymorphs, is a white crystalline powder. This form is an anhydrate with a melting point of 123-124° C. Forms I and III have been shown to convert to Form II both thermally in the solid state as well as in aqueous suspensions.

One aspect of the disclosure provides a compound that is crystalline Form II of Compound (I)

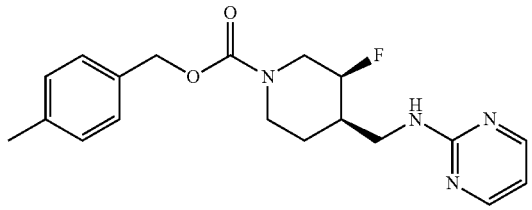

Figure 2:
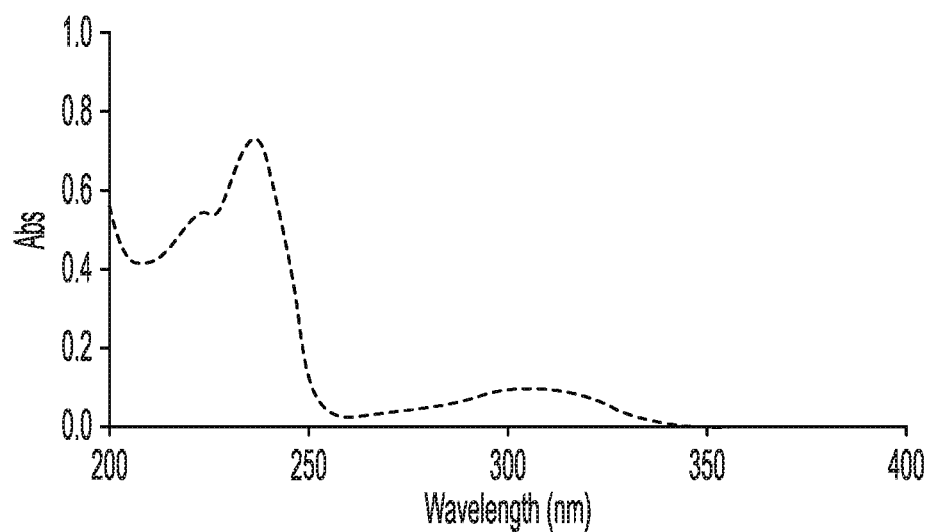
FIG. 2 shows an ultraviolet absorbance spectrum of crystalline Form II of Compound (I).
Figure 3:
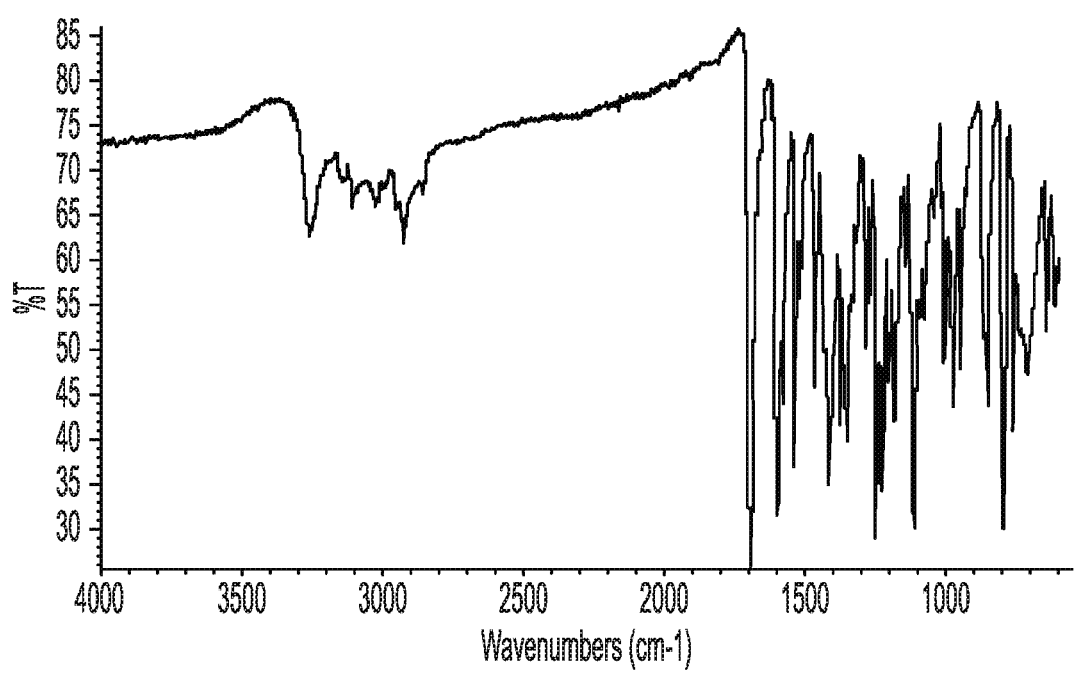
FIG. 3 shows an infrared spectrum of crystalline Form II of Compound (I).
Figure 4:
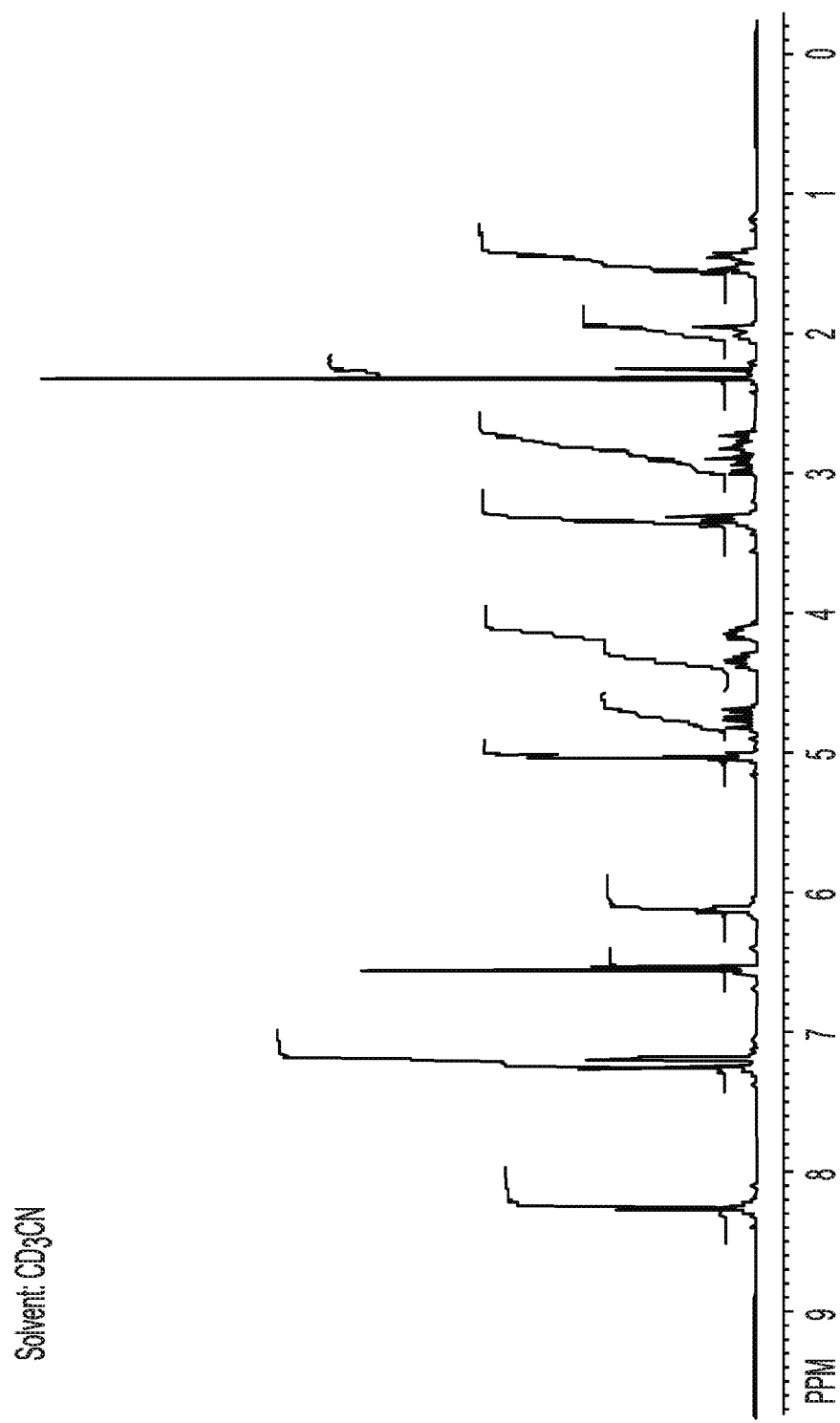
FIG. 4 shows proton nuclear magnetic resonance spectrum of crystalline Form II of Compound (I).
Figure 5:
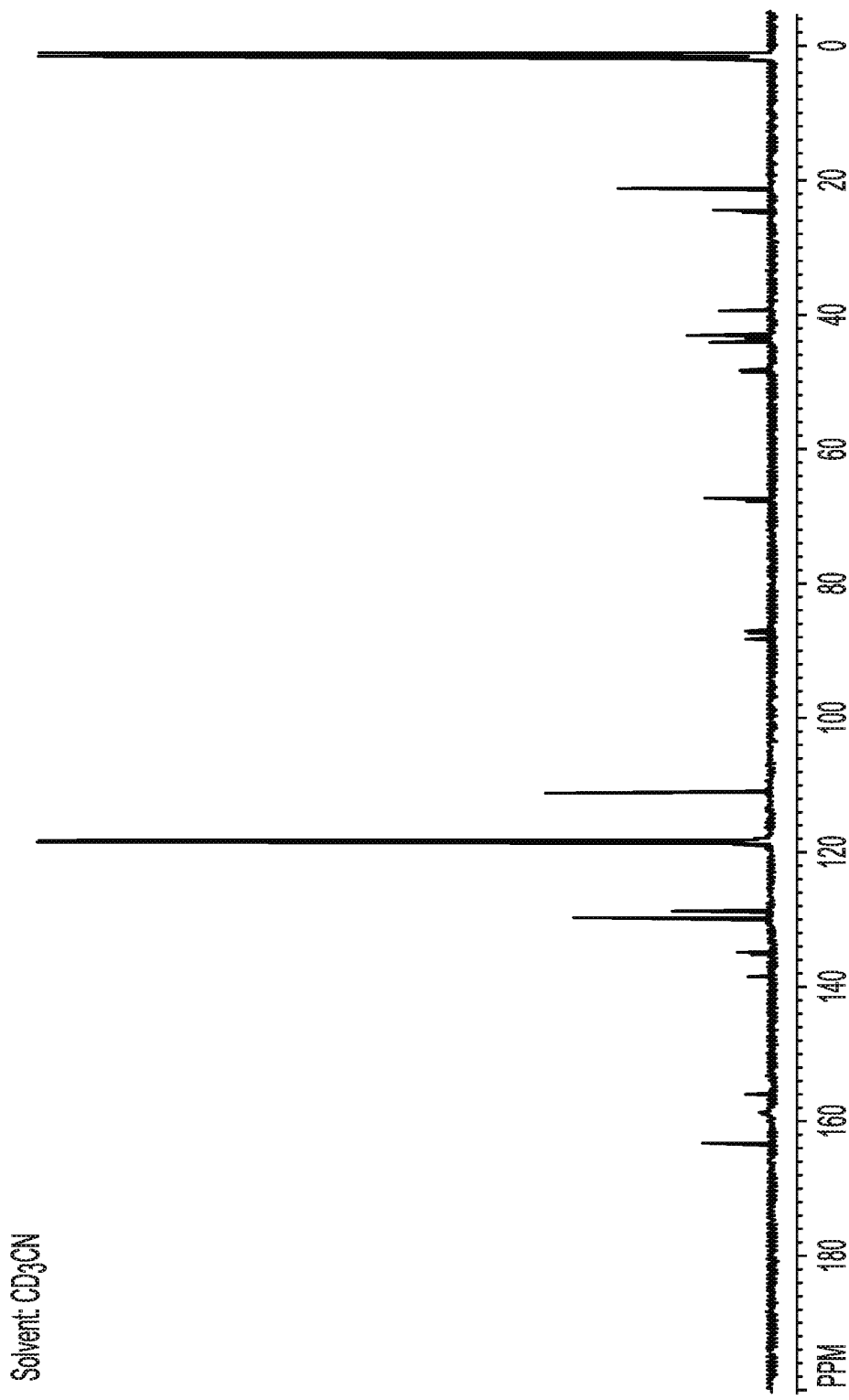
FIG. 5 shows a $^{13}C$ nuclear magnetic resonance spectrum of crystalline Form II of Compound (I).
Figure 6:
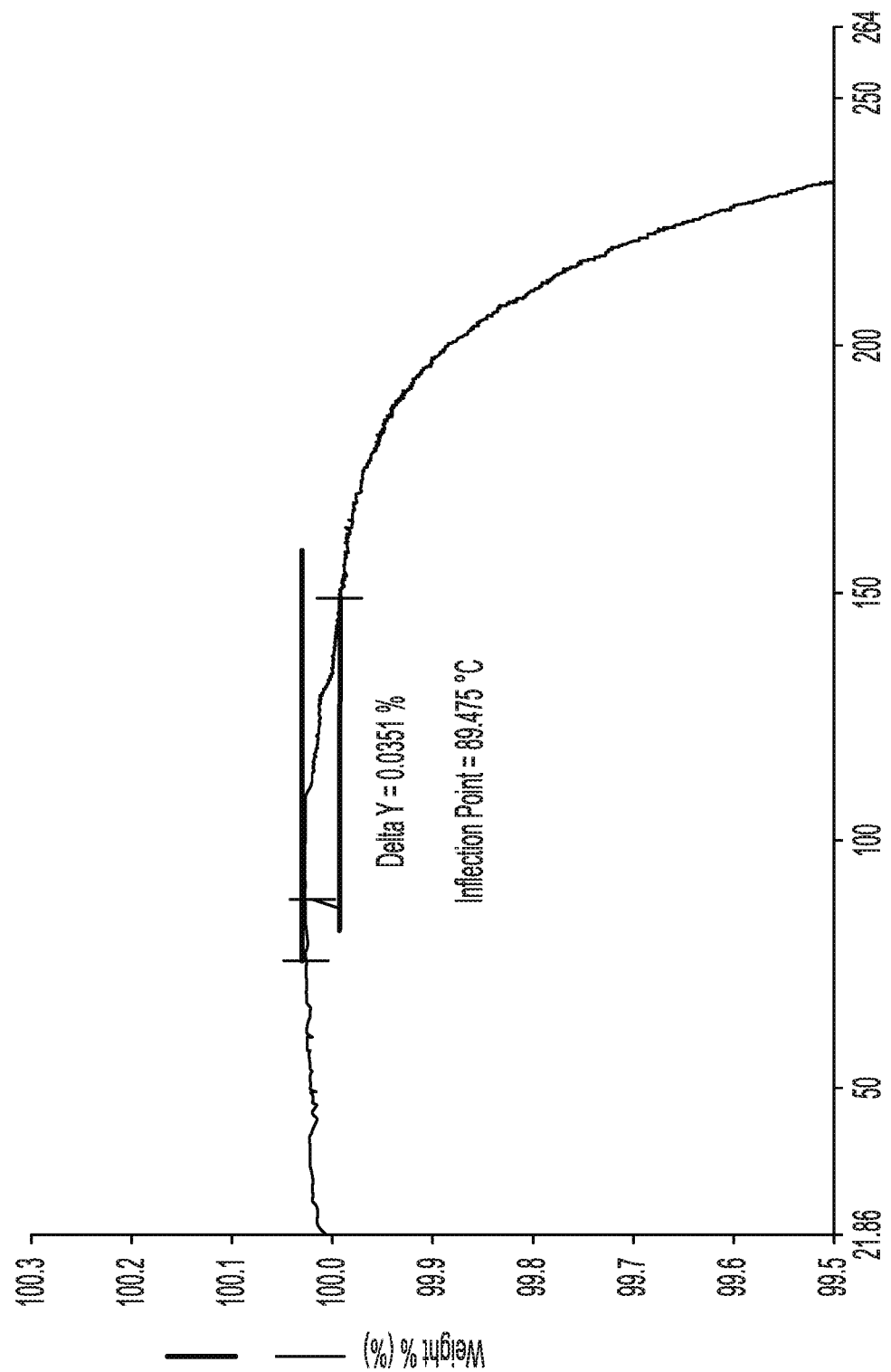
FIG. 6 shows a thermogravimetric analysis curve of crystalline Form II of Compound (I).
Figure 7:
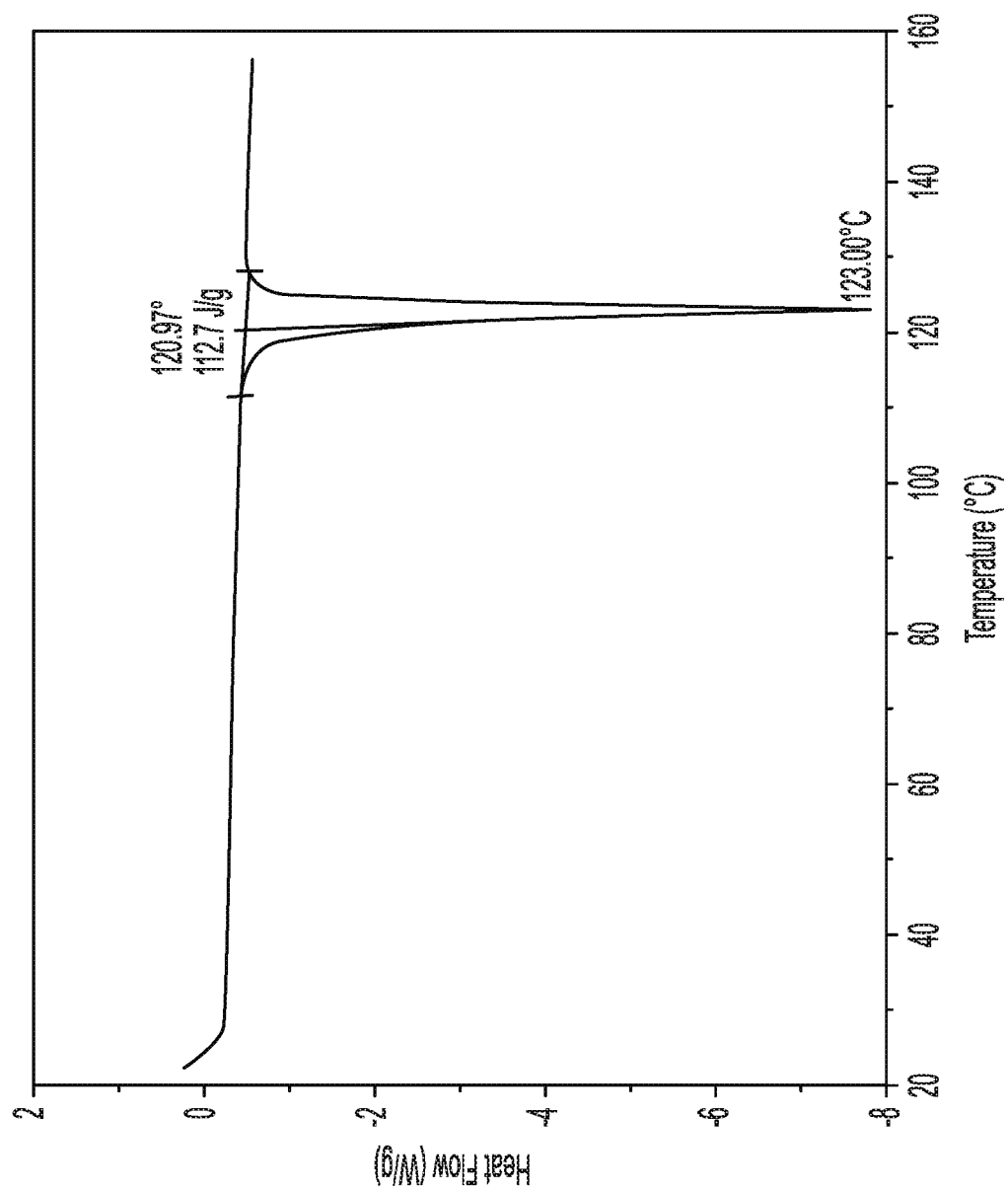
FIG. 7 shows a differential scanning calorimetry thermogram of crystalline Form II of Compound (I).

(I)

exhibiting at least one of:
(i) an X-ray powder diffraction pattern, obtained using copper Kα radiation, comprising peaks of 2-theta angles of about 5.9 and 8.8 degrees;
(ii) an X-ray powder diffraction pattern, obtained using copper Kα radiation, substantially as shown in FIG. 1A;
(iii) an ultraviolet absorbance spectrum, obtained using methanol as diluent, substantially as shown in FIG. 2;
(iv) an infrared spectrum substantially as shown in FIG. 3;
(v) a proton nuclear magnetic resonance spectrum at about 600 MHz in $CD_3CN$ substantially as shown in FIG. 4;
(vi) a $^{13}C$ nuclear magnetic resonance spectrum at about 150 MHz in $CD_3CN$ substantially as shown in FIG. 5;
(vii) a thermogravimetric analysis curve substantially as shown in FIG. 6; and
(viii) a differential scanning calorimetry thermogram substantially as shown in FIG. 7.

In one embodiment, the crystalline Form II of Compound (I) is substantially pure. "Substantially pure" refers to crystalline Form II of Compound (I) in isolated form that is at least about 90% by weight pure or free of impurities, including other polymorphic forms. In one embodiment, the substantially pure crystalline Form II of Compound (I) is at least about 95% by weight pure. In another embodiment, the substantially pure crystalline Form II of Compound (I) is at least about 96% by weight pure. In another embodiment, the substantially pure crystalline Form II of Compound (I) is at least about 97% by weight pure. In another embodiment, the substantially pure crystalline Form II of Compound (I) is at least about 98% by weight pure. In another embodiment, the substantially pure crystalline Form II of Compound (I) is at least about 99% by weight pure. In another embodiment, the substantially pure crystalline Form II of Compound (I) is at least about 99.5% by weight pure. In another embodiment, the substantially pure crystalline Form II of Compound (I) is at least about 99.6% by weight pure. In another embodiment, the substantially pure crystalline Form II of Compound (I) is at least about 99.7% by weight pure. In another embodiment, the substantially pure crystalline Form II of Compound (I) is at least about 99.8% by weight pure. In another embodiment, the substantially pure crystalline Form II of Compound (I) is at least about 99.9% by weight pure. Percent purity may be assessed by any method known in the art, such gas chromatography (GC), column chromatography (CC), liquid chromatography (LC), high-pressure liquid chromatography (HPLC), thin layer chromatography (TLC), mass spectrometry (MS) and/or high-resolution mass spectrometry (FIRMS).

In another embodiment, the compound exhibits an X-ray powder diffraction pattern comprising peaks of 2-theta angles of about 5.9 and 8.8 degrees that correspond, respectively, to d-spacing at about 14.9 and 10.0 Angstroms (Å).

In another embodiment, the compound exhibits an X-ray powder diffraction pattern substantially as shown in FIG. 1A. In another embodiment, the compound further exhibits at least one of: an ultraviolet absorbance spectrum substantially as shown in FIG. 2, an infrared spectrum substantially as shown in FIG. 3, a proton nuclear magnetic resonance spectrum substantially as shown in FIG. 4, a $^{13}C$ nuclear magnetic resonance spectrum substantially as shown in FIG. 5, a thermogravimetric analysis curve substantially as shown in FIG. 6, and a differential scanning calorimetry thermogram substantially as shown in FIG. 7.

In another embodiment, the compound exhibits an ultraviolet absorbance spectrum substantially as shown in FIG. 2. In another embodiment, the ultraviolet absorbance spectrum comprises an absorbance maximum at about 236±2 nm.

In another embodiment, the compound exhibits an infrared spectrum substantially as shown in FIG. 3.

In another embodiment, the compound exhibits a proton nuclear magnetic resonance spectrum substantially as shown in FIG. 4. In another embodiment, the proton nuclear magnetic resonance spectrum comprises peaks substantially as set out in Table 1.

In another embodiment, the compound exhibits a $^{13}C$ nuclear magnetic resonance spectrum comprises peaks substantially as shown in FIG. 5. In another embodiment, the $^{13}C$ nuclear magnetic resonance spectrum comprises peaks substantially as set out in Table 2.

In another embodiment, the compound exhibits a thermogravimetric analysis curve substantially as shown in FIG. 6. In another embodiment, the thermogravimetric analysis curve corresponds to a weight loss of about 0.16% up to about 250° C.

In another embodiment, the compound exhibits a differential scanning calorimetry thermogram substantially as shown in FIG. 7. In another embodiment, the differential scanning calorimetry thermogram comprises an endothermic peak at a temperature of about 124° C.

Figure 1B:
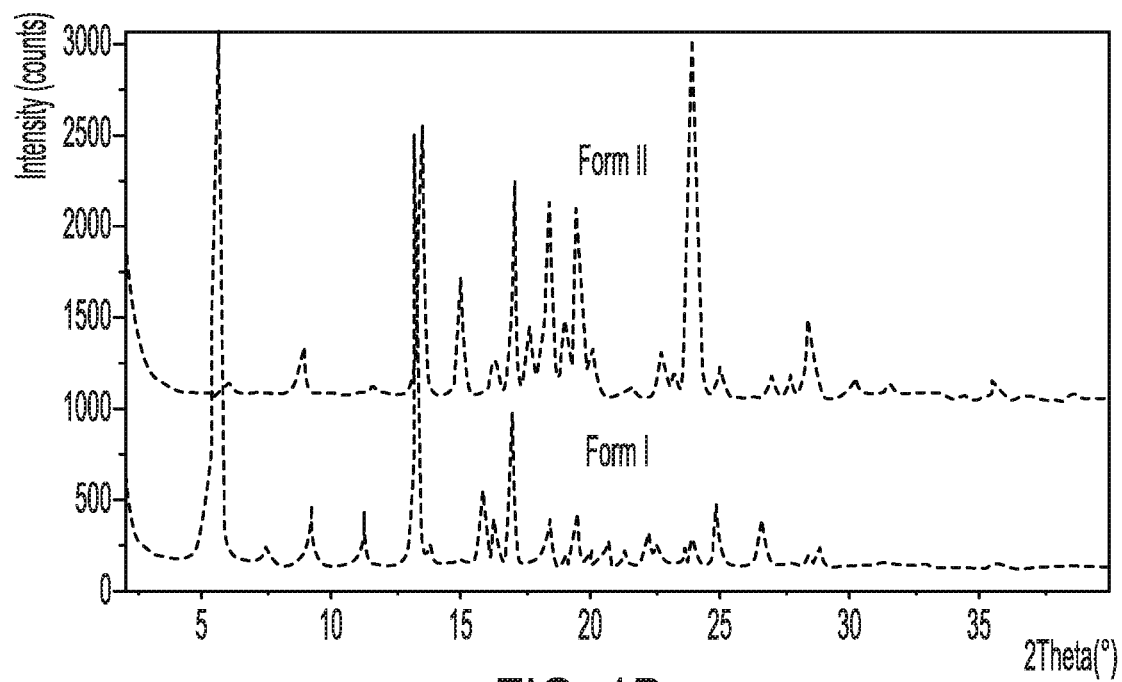
FIG. 1B shows X-ray powder diffraction patterns of crystalline Form I and crystalline Form II of Compound (I).

Also provided herein is a crystalline Form I of Compound (I) as described in FIG. 1B. The purity of Form I can be at least about 50%, at least about 60%, at least about 70%, at least about 80%, at least about 90%, or at least about 95%.

Pharmaceutical Compositions

Another aspect of the disclosure provides a pharmaceutical composition comprising an effective amount of crystalline Form II of Compound (I) as in any of the embodiments described above. In one embodiment, the crystalline Form II of Compound (I) is substantially pure as in any of the embodiments described above. Also provided herein is a pharmaceutical composition comprising an effective amount of crystalline Form I of Compound (I) as described herein.

Another aspect of the disclosure provides a pharmaceutical composition comprising an effective amount of Compound (I) in particulate form with an X90 particle size of about 10 μm or less. In one embodiment, the X90 particle size is about 8 μm or less. In another embodiment, the X90 particle size is about 6 μm or less. In another embodiment, the X90 particle size is about 5 μm or less. In another embodiment, the X90 particle size is between about 1 μm and about 10 μm. In another embodiment, the X90 particle size is between about 2 μm and about 8 μm. In another embodiment, the X90 particle size is between about 3 μm and about 6 μm. In another embodiment, the X90 particle size is between about 4 μm and about 5 μm. In another embodiment, the X90 particle size is about 4.5 μm. Other exemplary embodiments of the X90 particle size include about 4 μm, about 3.5 μm, about 3 μm, about 2.5 μm, about 2 μm, about 1.5 μm, about 1 μm, about 0.9 μm, about 0.8 μm, about 0.7 μm, about 0.6 μm, about 0.5 μm, about 0.4 μm, about 0.3 μm, about 0.2 μm, and about 0.1 μm. In another embodiment, the Compound (I) is crystalline Form II. In another embodiment, the Compound (I) is substantially pure crystalline Form II. In another embodiment, the Compound (I) is crystalline Form I.

Another aspect of the disclosure provides a pharmaceutical composition comprising an effective amount of Compound (I) in particulate form with an X50 particle size of about 5 μm or less. In one embodiment, the X50 particle size is about 4 μm or less. In another embodiment, the X50 particle size is about 3 μm or less. In another embodiment, the X50 particle size is about 3 μm or less. In another embodiment, the X50 particle size is about 2 μm or less. In another embodiment, the X50 particle size is between about 1 μm and about 5 μm. In another embodiment, the X50 particle size is between about 1 μm and about 4 μm. In another embodiment, the X50 particle size is between about 1 μm and about 3 μm. In another embodiment, the X50 particle size is between about 1 μm and about 2 μm. In another embodiment, the X50 particle size is about 2 μm. In another embodiment, the X50 particle size is about 1.9 μm.

Another aspect of the disclosure provides a pharmaceutical composition comprising an effective amount of Compound (I) in particulate form with an X10 particle size of about 2 μm or less. In one embodiment, the X10 particle size is about 1 μm or less. In another embodiment, the X10 particle size is between about 0.1 μm and about 1 μm. In another embodiment, the X10 particle size is between about 0.1 μm and about 0.9 μm. In another embodiment, the X10 particle size is between about 0.5 μm and about 0.9 μm. In another embodiment, the X10 particle size is between about 0.7 μm and about 0.8 μm. In another embodiment, the X10 particle size is about 0.8 μm. In another embodiment, the X50 particle size is about 7.9 μm.

In some embodiments of the pharmaceutical compositions disclosed herein, the pharmaceutical composition further comprises a pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in *Remington: The Science and Practice of Pharmacy*, 21$^{st}$ Ed. (Lippincott Williams & Wilkins, Baltimore, Md., 2005).

In some embodiments of the pharmaceutical compositions disclosed herein, the pharmaceutical composition further comprises at least one additional active agent. Examples of such active agent include: (1) non-steroidal anti-inflammatory agents; (2) COX-2 inhibitors; (3) bradykinin B1 receptor antagonists; (4) sodium channel blockers and antagonists; (5) nitric oxide synthase (NOS) inhibitors; (6) glycine site antagonists; (7) potassium channel openers; (8) AMPA/kainate receptor antagonists; (9) calcium channel antagonists; (10) GABA-A receptor modulators (e.g., a GABA-A receptor agonist); (11) matrix metalloprotease (MMP) inhibitors; (12) thrombolytic agents; (13) opioids such as morphine; (14) neutrophil inhibitory factor (NIF); (15) L-Dopa; (16) carbidopa; (17) levodopa/carbidopa; (18) dopamine agonists such as bromocriptine, pergolide, pramipexole, ropinirole; (19) anticholinergics; (20) amantadine; (21) carbidopa; (22) catechol O-methyltransferase (COMT) inhibitors such as entacapone and tolcapone; (23) Monoamine oxidase B (MAO-B) inhibitors; (24) opiate agonists or antagonists; (25) 5HT receptor agonists or antagonists; (26) NMDA receptor agonists or antagonists; (27) NK1 antagonists; (28) selective serotonin reuptake inhibitors (SSRI) and selective serotonin and norepinephrine reuptake inhibitors (SSNRI); (29) tricyclic antidepressant drugs, (30) norepinephrine modulators; (31) lithium; (32) valproate; (33) D-serine; (34) neurontin (gabapentin); (35) antitussives; (36) antihistamines (e.g., first generation antihistamines); (37) decongestants; (38) expectorants; (39) mucolytics; (40) antipyretics; and (41) analgesics.

In some embodiments of the pharmaceutical compositions disclosed herein, the pharmaceutical composition further contains an anti-hypertensive agent. In some embodiments, the anti-hypertensive agent is an $\alpha_1$-adrenoreceptor antagonist or an $\alpha_2$-adrenoreceptor antagonist. Non-limiting examples of $\alpha_1$-adrenoreceptor antagonists include doxazosin, prazosin, terazosin, indoramin, metabolites thereof, and analogs thereof non-limiting examples of $\alpha_2$-adrenoreceptor antagonists include clonidine, guanabenz, guanoxabenz, metabolite thereof, and analogs thereof.

The pharmaceutical compositions can be prepared as any appropriate unit dosage form. For example, the pharmaceutical compositions can be formulated for administration in solid or liquid form, including those adapted for the following: (1) oral administration, for example, as drenches, tablets (such as those targeted for buccal, sublingual and systemic absorption, including over-encapsulation tablets), capsules (such as dry filled, hard gelatin, soft gelatin or over-encapsulation capsules), caplets, boluses, powders, sachets, granules, pastes, mouth sprays, troches, lozenges, pellets, syrups, suspensions, elixirs, liquids, liposomes, emulsions and microemulsions; or (2) parenteral administration by, for example, subcutaneous, intramuscular, intravenous or epidural injection as, for example, a sterile solution or suspension. Additionally, the pharmaceutical compositions can be formulated for immediate, sustained, extended, delayed or controlled release.

In one embodiment, the pharmaceutical composition is formulated for oral administration. In another embodiment, the pharmaceutical composition is in tablet or capsule form. In another embodiment, the pharmaceutical composition is in tablet form. In another embodiment, the pharmaceutical composition is in capsule form. In another embodiment, the tablet or capsule is formulated for immediate release. In another embodiment, the tablet or capsule is formulated for sustained, extended, delayed or controlled release.

Tablets can be made by compression or molding, optionally with one or more accessory ingredients. Compressed tablets can be prepared by compressing in a suitable machine Compound (I) in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide sustained, extended, delayed or controlled release of Compound (I). Methods of formulating such sustained, extended, delayed or controlled release compositions are known in the art and disclosed in issued U.S. patents, including but not limited to U.S. Pat. Nos. 4,369,174, 4,842,866, and the references cited therein. Coatings can be used for delivery of compounds to the intestine (see, e.g., U.S. Pat. Nos. 6,638, 534, 5,217,720, 6,569,457, and the references cited therein). In addition to tablets, other dosage forms, such as capsules, granulations and gel-caps, can be formulated to provide sustained, extended, delayed or controlled release of Compound (I).

In another embodiment, the pharmaceutical composition is formulated for parenteral administration. Examples of a pharmaceutical composition suitable for parenteral administration include aqueous sterile injection solutions and non-aqueous sterile injection solutions, each containing, for example, anti-oxidants, buffers, bacteriostats and/or solutes that render the formulation isotonic with the blood of the intended recipient; and aqueous sterile suspensions and non-aqueous sterile suspensions, each containing, for example, suspending agents and/or thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use. In one embodiment, the pharmaceutical composition is formulated for intravenous administration.

In another embodiment, the effective amount of the Compound (I) or crystalline Form (I) or (II) of Compound I is between about 1 mg and about 200 mg. In another embodiment, the effective amount is between about 4 mg and about 16 mg. In another embodiment, the effective amount is between about 4 mg and about 12 mg. In another embodiment, the effective amount is between about 4 mg and about 8 mg. In another embodiment, the effective amount is between about 8 mg and about 20 mg. In another embodiment, the effective amount is between about 12 mg and about 20 mg. In another embodiment, the effective amount is between about 16 mg and about 20 mg. In another embodiment, the effective amount is between about 8 mg and about 20 mg. In another embodiment, the effective amount is between about 8 mg and about 16 mg. In another embodiment, the effective amount is between about 8 mg and about 12 mg. In another embodiment, the effective amount is between about 12 mg and about 20 mg. In another embodiment, the effective amount is between about 12 mg and about 16 mg. In another embodiment, the effective amount is about 4 mg. In another embodiment, the effective amount is about 8 mg. In another embodiment, the effective amount is about 12 mg. In another embodiment, the effective amount is about 16 mg. In another embodiment, the effective amount is about 20 mg.

In connection with the embodiments described herein, there is also provided a kit containing the above disclosed Compound (I) and a secondary agent. In an exemplary embodiment, the kit contains Compound (I) and one or more secondary agent selected from a selective serotonin reuptake inhibitor (S SRI), a selective serotonin and norepinephrine reuptake inhibitor (SSNRI), a tricyclic antidepressant drug, a norepinephrine modulator, an antitussive, an antihistamine, a decongestant, an expectorants, a mucolytics, a antipyretics, an analgesics, and an anti-hypertensive agent. In some embodiments, two or more ingredients (Compound (I) and secondary agents) may be administered simultaneously.

In some embodiments, the kit may include an anti-hypertensive agent as a secondary. In some embodiments, the anti-hypertensive agent is an $\alpha_1$-adrenoreceptor blocker. Non-limiting examples of $\alpha_1$-adrenoreceptor antagonists include doxazosin, prazosin, terazosin, indoramin, metabolites thereof, pharmaceutically acceptable salts thereof, and analogs thereof.

In some embodiments, the agents can be administered sequentially. The specific administration mode and dosing schedule can be determined by one of ordinary skill in the art (e.g. a practicing physician) without undue experimentation.

Methods of Use

Another aspect of the disclosure provides a method of treating or preventing a condition responsive to an NR2B antagonist, comprising administering to a patient in need thereof an effective amount of crystalline Form I or II of Compound (I) or a pharmaceutical composition comprising crystalline Form I or II of Compound (I). In one embodiment, the method is of treating a condition responsive to an NR2B antagonist. In another embodiment, the crystalline Form II is substantially pure as in any of the embodiments described above.

In another embodiment, the condition responsive to an NR2B antagonist is a depressive disorder. In another embodiment, the condition is major depressive disorder (MDD). In another embodiment, the condition is treatment-resistant major depressive disorder (TRMDD). In another embodiment, the condition is bipolar disorder with depressive feature. In another embodiment, the condition is anxiety disorder. In another embodiment, the condition is posttraumatic stress disorder (PTSD). In another embodiment, the condition is a depressive disorder, MDD or TRMDD with suicidal ideation.

In another embodiment, the compound or pharmaceutical composition is administered with food. In another embodiment, the compound or pharmaceutical composition is administered without food.

Also provided is a method of targeting N-methyl-D-aspartate (NMDA) receptor subunit 2B (GluN2B) expressed on a cell by administering to a subject in need thereof a therapeutically effective amount of Form I or Form II of compound I, allowing sufficient amount of time for the compound to bind to GluN2B. As explained above, GluN2B plays a key role in various diseases including for example schizophrenia, stroke, traumatic brain injury, Alzheimer's disease, cerebral ischemia, amyotrophic lateral sclerosis, Huntington's disease, sensorineural hearing loss, tinnitus, glaucoma, neurological damage caused by epileptic seizures or by neurotoxin poisoning or by impairment of glucose and/or oxygen to the brain, vision loss caused by neurodegeneration of the visual pathway, Restless Leg Syndrome, multi-system atrophy, non-vascular headache, chronic (or chronic persistent), subchronic or acute cough, primary hyperalgesia, secondary hyperalgesia, primary allodynia, secondary allodynia, or other pain caused by central sensitization, dyskinesias (such as the side effects accompanying normal doses of L-Dopa), depressive disorders (such as, major depressive disorder (MDD) and treatment-resistant MDD), trauma- and stressor-related disorders (such as acute stress disorder and posttraumatic stress disorder (PTSD)), bipolar disorders with depressive features, anxiety disorders, and obsessive-compulsive and related disorders. By antagonizing GluN2B with the compound I (Form I or II), the present invention provides a novel approach in treating GluN2B-associated diseases.

Another aspect of the disclosure provides a method of treating or preventing a condition responsive to an NR2B antagonist, comprising administering to a patient in need thereof an effective amount of Compound (I) in particulate form (Form I or Form II) with an X90, X50 or X10 particle size as in any of the embodiments described above. In one embodiment, the method is of treating a condition responsive to an NR2B antagonist. In another embodiment, the Compound (I) is crystalline Form II as in any of the embodiments described above. In another embodiment, the crystalline Form II is substantially pure as in any of the embodiments described above. In another embodiment, the condition responsive to an NR2B antagonist is a depressive disorder. In another embodiment, the condition is major depressive disorder (MDD). In another embodiment, the condition is treatment-resistant major depressive disorder (TRMDD). In another embodiment, the condition is a depressive disorder, MDD or TRMDD with suicidal ideation. In one embodiment, the compound or pharmaceutical composition is administered with food. In another embodiment, the compound or pharmaceutical composition is administered without food.

Another aspect of the disclosure provides a method of treating or preventing suicidal ideation, comprising administering an effective amount of Compound (I) (Form I or Form II) to a patient who has, is suspected of having, or has been diagnosed with having suicidal ideation. In one embodiment, the method is of treating suicidal ideation. In another embodiment, the Compound (I) is in particulate form with an X90, X50 or X10 particle size as in any of the embodiments described above. In another embodiment, the Compound (I) is crystalline Form II as in any of the embodiments described above. In another embodiment, the crystalline Form II is substantially pure as in any of the embodiments described above. In another embodiment, the Compound (I) is crystalline Form I as in any of the embodiments described above.

In another embodiment, the patient has been diagnosed with having suicidal ideation within about 4 weeks prior to administration of the compound. In another embodiment, the patient has been further diagnosed with having a depressive disorder. In another embodiment, the patient has been further diagnosed with having major depressive disorder (MDD). In another embodiment, the patient has been further diagnosed with having treatment-resistant major depressive disorder (TRMDD). In one embodiment, the compound or pharmaceutical composition is administered with food. In another embodiment, the compound or pharmaceutical composition is administered without food.

Another aspect of the disclosure provides a method of reducing absorption rate of Compound (I) comprising administering to a patient in need thereof an effective amount of the Compound (I) (Form I or Form II) with food, wherein the Compound (I) is administered either substantially concurrently with, or up to about 2 hours after, or up to about 30 minutes before administration of food. In one embodiment, the Compound (I) is in particulate form with an X90, X50 or X10 particle size as in any of the embodiments described above. In another embodiment, the Compound (I) is crystalline Form II as in any of the embodiments described above. In another embodiment, the crystalline Form II is substantially pure as in any of the embodiments described above.

In another embodiment, the method results in a lower $C_{max}$ or a higher $T_{max}$ compared to that of a method comprising administering the Compound (I) without food. In another embodiment, the Compound (I) is administered either substantially concurrently with, or up to about 90 minutes after, or up to about 15 minutes before administration of food. In another embodiment, the Compound (I) is administered either substantially concurrently with, or up to about 60 minutes after, or up to about 10 minutes before administration of food. In another embodiment, the Compound (I) is administered substantially concurrently with administration of food.

In any of the methods provided herein, administration of the compound or pharmaceutical composition may be via any accepted mode known in the art, such as orally or parenterally. The term "parenterally" includes without limitation subcutaneously, intravenously, intramuscularly, intraperitoneally, intrathecally, intraventricularly, intrasternally, intracranially, by intraosseous injection and by infusion techniques. In one embodiment, the compound or pharmaceutical composition is administered orally. In another embodiment, the compound or pharmaceutical composition is administered parenterally. In another embodiment, the compound or pharmaceutical composition is administered intravenously.

In any of the methods provided herein, the method may further comprise monitoring the patient's blood pressure; and if hypertension is detected, administering an anti-hypertensive to the patient.

In any of the methods provided herein, the compound or pharmaceutical composition may be used in combination with at least one additional active agent as disclosed above. The compound or pharmaceutical composition may be administered with the at least one additional active agent either together in a single composition or separately in individual compositions at substantially the same time or at different times (e.g., sequentially). Examples of such active agent include: (1) non-steroidal anti-inflammatory agents; (2) COX-2 inhibitors; (3) bradykinin B1 receptor antagonists; (4) sodium channel blockers and antagonists; (5) nitric oxide synthase (NOS) inhibitors; (6) glycine site antagonists; (7) potassium channel openers; (8) AMPA/kainate receptor antagonists; (9) calcium channel antagonists; (10) GABA-A receptor modulators (e.g., a GABA-A receptor agonist); (11) matrix metalloprotease (MMP) inhibitors; (12) thrombolytic agents; (13) opioids such as morphine; (14) neutrophil inhibitory factor (NIF); (15) L-Dopa; (16) carbidopa; (17) levodopa/carbidopa; (18) dopamine agonists such as bromocriptine, pergolide, pramipexole, ropinirole; (19) anticholinergics; (20) amantadine; (21) carbidopa; (22) catechol O-methyltransferase (COMT) inhibitors such as entacapone and tolcapone; (23) Monoamine oxidase B (MAO-B) inhibitors; (24) opiate agonists or antagonists; (25) 5HT receptor agonists or antagonists; (26) NMDA receptor agonists or antagonists; (27) NK1 antagonists; (28) selective serotonin reuptake inhibitors (SSRI) and selective serotonin and norepinephrine reuptake inhibitors (SSNRI); (29) tricyclic antidepressant drugs, (30) norepinephrine modulators; (31) lithium; (32) valproate; (33) D-serine; and (34) neurontin (gabapentin); (35) antitussives; (36) antihistamines (e.g., first generation antihistamines); (37) decongestants; (38) expectorants; (39) mucolytics; (40) antipyretics; and (41) analgesics. In some embodiments, the compound or pharmaceutical composition is administered with at least one additional active agent selected from antitussives, first generation antihistamines, decongestants, expectorants, mucolytics, antipyretics, analgesics.

In some embodiments, the compound or pharmaceutical composition is administered as an adjunct to a selective serotonin reuptake inhibitor (SSRI) or selective serotonin and norepinephrine reuptake inhibitor (SSNRI). Examples of SSRI and SSNRI include binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine. In another embodiment, the method improves the efficacy of the SSRI or SSNRI in the treatment or prevention of a condition responsive to an NR2B antagonist. In another embodiment, the method reduces the time it takes for a patient to respond to treatment with an SSRI or SSNRI. In another embodiment, the method reduces the dose of SSRI or SSNRI that a patient would otherwise need. In another embodiment, the method reduces the severity of a condition or the number or severity of symptoms associated with a condition. In another embodiment, the condition is a depressive disorder. In another embodiment, the condition is major depressive disorder (MDD). In another embodiment, the condition is treatment-resistant major depressive disorder (TRMDD). In another embodiment, the condition is a depressive disorder, MDD or TRMDD with suicidal ideation. The adjunct may be administered with the at least one additional treatment either together in a single composition or separately in individual compositions at substantially the same time or at different times.

In any of the methods provided herein, Compound (I) (Form I or Form II) may be administered in conjunction with an anti-hypertensive agent. The use of Compound (I) may be associated with an increase in blood pressure that is likely due to increased $\alpha_1$-adrenergic tone in peripheral arterioles mediated by circulating norepinephrine. The increase on blood pressure is mostly transient as it relates to arteriolar vasoconstriction, in contrast to other frequent causes of hypertension such as cardiac stimulation, arterial wall hypertrophy, salt retention and fluid overload.

Accordingly, in some embodiments, the anti-hypertensive agent is an $\alpha_1$-adrenoreceptor, that blocks peripheral $\alpha_1$-adrenergic receptors. Non-limiting examples of $\alpha_1$-adrenoreceptor antagonists include Doxazosin, Prazosin, Terazosin, indoramin, metabolites thereof, pharmaceutically acceptable salts thereof, and analogs thereof. These agents are highly selective for α1-adrenoceptor subtypes (alpha1A, alpha1B, alpha1D). When given in large doses, they do not inhibit the $\alpha_2$-adrenoceptors (alpha2A, alpha2B, alpha2C), the β-adrenoceptors (beta1, beta2, beta3), or other receptors such as acetylcholine (muscarinic), dopamine, and 5-hydroxytryptamine (5-HT, serotonin) receptors. In some embodiments, the anti-hypertensive agent is an $\alpha_2$-adrenoreceptor antagonist, that reduces central adrenergic outflow. Non-limiting examples of $\alpha_2$-adrenoreceptor antagonists include clonidine, guanabenz, guanoxabenz, metabolite thereof, and analogs thereof. Compound (I) and the anti-hypertensive agent may be administered simultaneously or separately. These agents stimulate α2-adrenoceptors and inhibit brainstem vasomotor center-mediated norepinephrine release.

Other suitable antihypertensives include calcium channel blockers, diuretics and angiotensin converting enzyme (ACE) inhibitors. Non-limiting examples of calcium channel blockers include diltiazem, amlodipine, verapamil, diltiazem, nifedipine, amlodipine, felodipine, isradipine, nicardipine, cinnarizine, nisoldipine, and pharmaceutically acceptable salts thereof. Non-limiting examples of diuretics include thiazide diuretics, potassium-sparing diuretics, loop diuretics, and pharmaceutically acceptable salts thereof. Non-limiting examples of angiotensin converting enzyme (ACE) inhibitors include alacepril, benazepril, benazeprilat, captopril, ceronapril, cilazapril, delapril, enalapril, enalaprilat, fosinopril, imidapril, lisinopril, moexipril, moveltopril, perindopril, quinapril, quinaprilat, ramipril, ramiprilat, spirapril, temocapril, trandolapril, zofenopril, and pharmaceutically acceptable salts thereof.

The antihypertensives described herein may be used in any suitable forms. Examples include doxazosin mesylate, prazosin hydrochloride, and terazosin hydrochloride.

Because the transient increase in blood pressure relates to the increased α1-adrenergic tone in peripheral arterioles mediated by circulating norepinephrine, blocking the α1-adrenoceptor or α2-adrenoceptor is able effectively to mitigate the blood pressure effect. In some embodiments, the active ingredient of the anti-hypertensive agent consists essentially of an al-adrenoreceptor antagonist, an α2-adrenoceptor antagonist, or both. In some embodiments, the active ingredient of the anti-hypertensive agent consists essentially of an α1-adrenoreceptor antagonist. The above described al-adrenoreceptor antagonist or α2-adrenoceptor antagonist can be administered before, during, or after the administration of Compound (I). In exemplary embodiments, the anti-hypertensive agent is administered 1, 2, 5, 10, 15, 20, 30, 60, 100 minutes prior to the administration of Compound (I). In other exemplary embodiments, the anti-hypertensive agent is administered 1, 2, 5, 10, 15, 20, 30, 60, 100 minutes after the administration of Compound (I). In some embodiments, the antihypertensive agent is administered at about the same time or sequentially with the administration of Compound (I). In some embodiments, the $\alpha_1$-adrenoreceptor antagonist or $\alpha_2$-adrenoceptor antagonist is administered only in the above described timeframe to control the transient blood pressure effect from Compound (I). In some embodiments, the $\alpha_1$-adrenoreceptor antagonist or $\alpha_2$-adrenoceptor antagonist is administered within 5, 10, 20, 30, or 60 minutes of the administration of Compound (I).

The effective amount or unit dosage of the hypertensive agent may range from about of between 0.001 to 100 mg/kg. of body weight. In some exemplary embodiments, the effective amount will be about 0.5 mg to 2500 mg, in yet some other embodiments about 5 mg to 50 mg.

In any of the methods provided herein, the compound or pharmaceutical composition may be administered intermittently. In some embodiments, the compound, secondary agent, combination of agents, or pharmaceutical composition may be independently administered once, twice, three times, four times or more per day. In some embodiments, the compound, secondary agent, combination of agents, or pharmaceutical composition may be independently administered once every 1, 2, 3, 4, 5, 6, 7, 10, 14, 15, 10 or 30 days.

In any of the methods provided herein, the effective amount or unit dosage of Compound (I) may be between about 1 mg and about 2000 mg daily, weekly or intermittently. For daily administration, the effective amount may be divided into two, three or more doses for multiple administrations a day. In one embodiment, the effective amount is between about 1 mg/day and about 60 mg/day. In another embodiment, the effective amount is between about 4 mg/day and about 20 mg/day. In another embodiment, the effective amount is between about 4 mg/day and about 8 mg/day. In another embodiment, the effective amount is about 4 mg/day. In another embodiment, the effective amount is about 8 mg/day. In another embodiment, the effective amount is about 16 mg/day. In another embodiment, the effective amount is about 20 mg/day. In another embodiment, the effective amount is between about 4 mg and about 60 mg intermittently. In another embodiment, the effective amount is between about 4 mg and about 60 mg intermittently throughout a 24 hour period. In another embodiment, the effective amount is between about 4 mg/day and about 20 mg/day intermittently throughout a 24 hour period. In another embodiment, the effective amount is between about 4 mg/day and about 8 mg/day intermittently throughout a 24 hour period.

Compound (I) may be administered intermittently in any of the methods of the present invention described herein. As exemplified in FIG. 13, Compound (I) demonstrated marketed effects in immobility, climbing and swimming 24 hours after administration. Accordingly, Compound (I) can be administered intermittently to achieve sustained therapeutic effects. In some embodiments, the therapeutically effective amount or unit dosage of Compound (I) is between about 4 mg and about 2000 mg intermittently throughout 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day period. Examples of intermittent administration include the administration of a therapeutically effect amount or a unit dosage of about 1, 2, 4, 6, 8, 10, 12, 14, 16, 18, 20, 25, 30, 35, 40, 50, 60, 70, 80, 90, 100, 200, 300, 400, or 500 mg of Compound (I) once every 1, 2, 3, 4, 5, 7, 10, 14, 15, 20, or 30 day period. In some embodiments, Compound (I) exists substantially in Form II. In further examples, such effective amount or unit dosage is administered once every day, once every 7 days, once every two weeks, once every 3 weeks, or once every month. In another embodiment, the effective amount is between about 8 mg and about 200 mg intermittently throughout a 7 day period. In another embodiment, the effective amount is between about 12 mg and about 60 mg intermittently throughout a 7 day period. In another embodiment, the effective amount is between about 16 mg and about 60 mg intermittently throughout a 7 day period. In another embodiment, the effective amount is between about 20 mg and about 60 mg intermittently throughout a 7 day period.

There may be an interval of between about 1 and 30 days between days of administration of Compound (I). Depending on the disease condition, treatment response and phase of treatment, the length of the interval may vary accordingly. For example, each interval may independently be 1, 2, 3, 4, 5, 6, 7, 8, 9 or 10 day long. In an exemplary embodiment, an initial administration of the compound on the first day may be followed by a 2-day interval before a second administration on the third day, which is then followed by a 6-day interval before a third administration.

In some embodiments of the methods disclosed herein, the compound or pharmaceutical composition is administered at a weight base dose. Therefore, in some embodiments, the effective amount is about 0.01 to about 1 mg/kg daily or intermittently.

The dose level can be adjusted for intravenous administration. In such case, the compound or pharmaceutical composition can be administered in an amount of between about 0.01 µg/kg/min to about 100 ng/kg/min.

In some embodiments, the administration regimen comprises a first initiation phase and a second maintenance phase. The dose in the first phase serves to reach a desirable therapeutic level whereas the dose of the second phase provides a sustained therapeutic effect. The daily dose of the first initiation phase may be more, less than or the same as that of the maintenance phase. The effective amount of Compound (I) for each phase may be, for example, between about 4 mg and about 60 mg daily or intermittently. Independently during each phase, the compound or pharmaceutical composition can be administered 1, 2, 3, 4 or more times on the day of administration. The length of the initiation phase may be any suitable period of time from a day to a week or a month, including for example 1, 2, 3, 4, 5, 6, 7, 8, 9, 10, or 15 days. The maintenance phase may last from days to years or as long as needed. In exemplary embodiments, the intermittent dosing schedule for initiation phase and maintenance phase independently includes administration of the compound every two days, every three days, every four days, every five days, every six days, every week, every 10 days, every two weeks, or every month. The effective amount for the initiation phase and the maintenance phase is independently selected from the range or value describe above for daily or intermittent administration.

With each of the above phases, additional adjustment in the dose and dosing schedule can be made. The adjustment will depend on the specific circumstances (for example, the presence or absence of a predisposition to the disease or condition being treated, the severity or expected severity of the disease, or the age or general health of the patient), even doses outside the aforementioned ranges may be in order. For example, the initiation phase may start with a higher daily dose than the dose for rest of the administration regimen. The administration may also include a toleration phase, where the compound is administered to a subject at a dose and for a period sufficient to allow the subject/patient to tolerate the dose without showing any adverse effects. The dose can then be increased at selected intervals of time until a therapeutic dose is achieved. The particular dose given the specific circumstances can be determined by a physician or other health-care professional of ordinary skill.

These compositions of the present invention may contain immediate release, sustained or extended release, delayed release components, or combinations thereof. The preparation of pharmaceutical or pharmacological compositions are known to those of skill in the art in light of the present disclosure. General techniques for formulation and administration are found in "Remington: The Science and Practice of Pharmacy, Twentieth Edition," Lippincott Williams & Wilkins, Philadelphia, Pa. Tablets, capsules, pills, powders, granules, dragées, gels, slurries, ointments, solutions suppositories, injections, inhalants and aerosols are examples of such formulations. For instance, extended or modified release oral formulation can be prepared using methods known in the art. An extended release form of the pharmaceutical composition may be a matrix tablet or capsule composition.

Another aspect of the disclosure provides a method of increasing bioavailability of Compound (I), comprising administering to a patient in need thereof an effective amount of Compound (I), or a pharmaceutical composition comprising Compound (I), wherein the Compound (I) is in particulate form with an X90, X50 or X10 particle size as in any of the embodiments described above. In one embodiment, the Compound (I) is crystalline Form II as in any of the embodiments described above. In another embodiment, the crystalline Form II is substantially pure as in any of the embodiments described above. In another embodiment, the Compound (I) is crystalline Form I as in any of the embodiments described above.

In another embodiment, the method results in a higher area under the curve compared to that of a method comprising administering Compound (I) having an X90 particle size of about 10 μm or higher. In another embodiment, the method results in a higher area under the curve compared to that of a method comprising administering Compound (I) having an X90 particle size of about 11 μm or higher. In another embodiment, the method results in a higher area under the curve compared to that of a method comprising administering Compound (I) having an X90 particle size of about 12 μm or higher. In another embodiment, the method results in a higher area under the curve compared to that of a method comprising administering Compound (I) having an X90 particle size of about 13 μm or higher. In another embodiment, the method results in a higher area under the curve compared to that of a method comprising administering Compound (I) having an X90 particle size of about 14 μm or higher.

In another embodiment, the method results in a higher area under the curve compared to that of a method comprising administering Compound (I) having a D43 particle size of about 10 μm or higher. In another embodiment, the method results in a higher area under the curve compared to that of a method comprising administering Compound (I) having a D43 particle size of about 11 μm or higher. In another embodiment, the method results in a higher area under the curve compared to that of a method comprising administering Compound (I) having an D43 particle size of about 12 μm or higher. In another embodiment, the method results in a higher area under the curve compared to that of a method comprising administering Compound (I) having a D43 particle size of about 13 μm or higher. In another embodiment, the method results in a higher area under the curve compared to that of a method comprising administering Compound (I) having a D43 particle size of about 14 μm or higher.

In one embodiment, the compound or pharmaceutical composition is administered with food. In another embodiment, the compound or pharmaceutical composition is administered without food.

Methods of Manufacture

Another aspect of the invention provides a method for the conversion from compound A to compound B under transition metal catalyzed hydrogenation conditions:

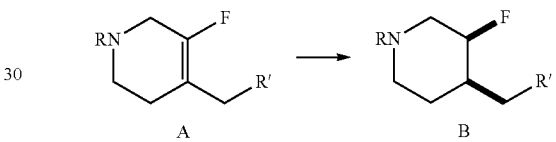

Wherein R' is
1). OH;
2). NH2: or
3). NHHet, wherein Het is a 5 or 6 membered heteroaromatic ring containing 1 or 2 nitrogen ring atoms, thiazolyl, or thiadiazolyl, the NH is linked to a carbon ortho to a nitrogen on the Het ring, and Het is optionally substituted with 1 or 2 substituents, each substituent independently is C1-4alkyl, fluoro, chloro, bromo, or iodo.

Examples of compound A include:

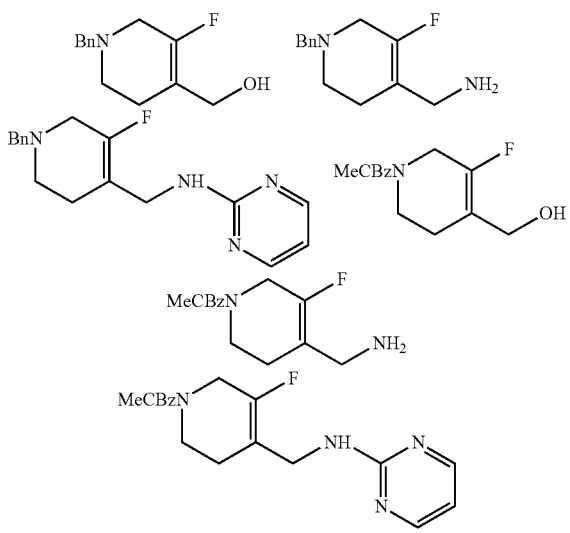

Besides Bn (Benzyl) and Bz (Benzoyl), other protecting groups may also be used to prepare analogs of compound A.

Various transition metals, including for example palladium and ruthenium, can be used as the catalyst. The catalyst can be prepared from transition precursor complexes and suitable ligands. For example, ruthenium precursor complexes include [(COD)]RhCl]2 and similar complexes employing cationic OTf⁻ and $BF_4^-$ salts. Suitable ligands include, for example, Josiphos and Walphos:

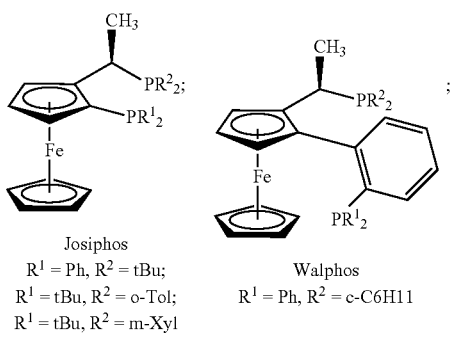

Josiphos
$R^1$ = Ph, $R^2$ = tBu;
$R^1$ = tBu, $R^2$ = o-Tol;
$R^1$ = tBu, $R^2$ = m-Xyl Walphos
$R^1$ = Ph, $R^2$ = c-C6H11

In some embodiments, compound A may exist in an acid form such as HCl salt, toluenesulfonic acid (TSA) salt, and methanesulfonic acid (MSA) salt. Various solvents, including co-solvents of two or more solvents may be used in the hydrogenation reaction. The exact condition, such as the ratio of the catalyst to the substrate and the amount of the ligand, can be determined by one of ordinary skill in the art without undue experimentation.

Novel methods have been developed to prepare Compound (I) and crystalline Form I or II of Compound (I) in high purity on a large scale. The methods provided herein differ from the methods disclosed in U.S. Pat. No. 7,592,360 and PCT International Publication No. WO 2006/069287 in many respects, including the type and amount of reactants, intermediates, reaction conditions, and inclusion or omission of specific steps. For example, neither of the methods disclosed in the '360 patent and the '287 PCT publication includes steps for converting Form I of Compound (I) into Form II. Furthermore, whereas the methods provided herein use intermediate Compound (8)

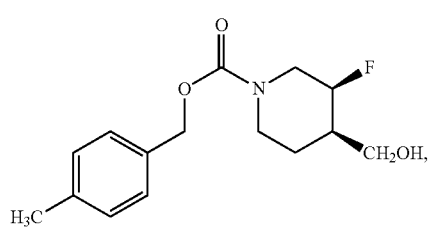

(8)

the method disclosed in the '360 patent uses the intermediate (±)-((cis)-3-fluoro-1-{[(4-methylbenzyl)oxy]carbonyl}piperidin-4-yl)acetic acid

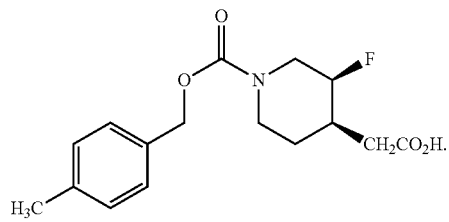

Additionally, the methods provided herein use different reactants, amounts of reactants and reaction conditions than those recited in the '287 PCT publication.

One aspect of the disclosure provides a method of preparing Compound (I) comprising:

(i) reacting Compound (8)

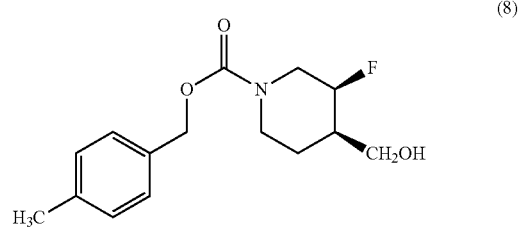 [SMILES: Cc1ccc(COC(=O)N2CC[C@H](CO)[C@H](F)C2)cc1]

(8)

with triflic anhydride to yield a triflate;

(ii) reacting the triflate with ammonia to yield Compound (9)

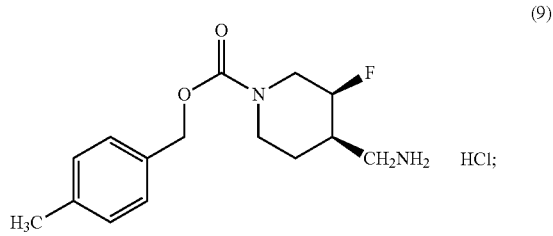

(9)

and (iii) reacting the Compound (9) with 2-chloropyrimidine to yield Form I of Compound (I).

In one embodiment, the method further comprises seeding Form I of Compound (II) with Form II of Compound (I).

In another embodiment, the method further comprises reacting Compound (6)

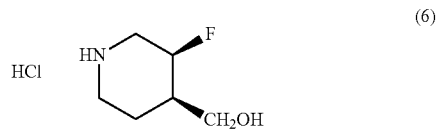

(6)

with carbonyldiimidazole and Compound (7)

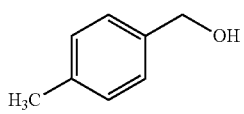
(7)

to yield Compound (8).

In another embodiment, the method further comprises debenzylating Compound (5)

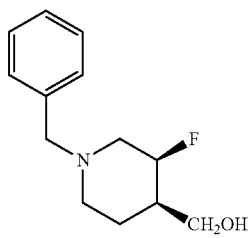
(5)

with hydrogen over palladium to yield Compound (6).

In another embodiment, the method further comprises reducing Compound (4)

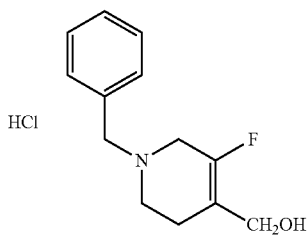
(4)

with chloro(1,5-cyclooctadiene)rhodium (I) dimer under hydrogen atmosphere to yield Compound (5).

In another embodiment, the method further comprises purifying the Compound (I). In another embodiment, the purifying comprises slurrying or recrystallization. In another embodiment, the purifying comprises slurrying followed by recrystallization. In some embodiments, Form I of Compound (I) is purified by recrystallization in a suitable solvent such as ethyl acetate or a co-solvent including ethyl acetate and heptane.

Form I of Compound (I) can be converted to Form II in different ways. In some embodiments, Form I of Compound (I) in solid state is heated to a temperature above room temperature for a desirable period of time. Exemplary temperatures for promoting such conversion includes about 50° C., 60° C., 70° C., 80° C., 90° C., 100° C., 105° C., 110° C., 115° C., 120° C., 125° C., 130° C., 135° C., 140° C., and 150° C. In some embodiments, the temperature ranges from about 90-135° C., all subranges included. In some more exemplary embodiments, the temperature is about 100-105° C., 100-110° C., or 100-115° C. The heating can be maintained for a period, for example from about 1 minute to 30 hours, all subranges included. Exemplary length of heating include about 10 minutes, 20 minutes, 30 minutes, 40 minutes, 50 minutes, 1 hour, 2 hours, 3 hours, 5 hours, 10 hours and 24 hours.

Form II of Compound (I) may also be obtained by the slurrying of Form I in a suitable solvent or co-solvents. Stirring or heating may be applied. In an exemplary embodiment, Form I of Compound (I) can be suspended in water at room temperature for over 24 hours. If necessary, the time can be further extended to allow the complete conversion of Form I to Form II.

Subsequent to the conversion of Form I of Compound (I), Form II may be isolated using routine steps. In some embodiments, the isolation includes filtration and/or washing with a suitable solvent.

Large scale production of Form II can be achieved by seeding Form I with Form II. Seeding is an important step to induce the growth of crystal material from a small crystal of the target form. A system of a single solvent or multiple solvents may be used for seeding and crystal growth. In some embodiments, the system contains the co-solvent of methanol and acetic acid.

EXAMPLES

The following examples are presented for illustrative purposes and should not serve to limit the scope of the disclosed subject matter.

Example 1: Preparation of Compound (I) and Crystalline Form II

Scheme I

Step 1
1) Hexyllithium / THF
   DIPA / DMF, -60° C.
2) Water, RT
3) NaBH4 / NaOH, <0° C.
4) HCl then NaOH solutions
5) iPrOAc
6) iPrOAc / nHeptane

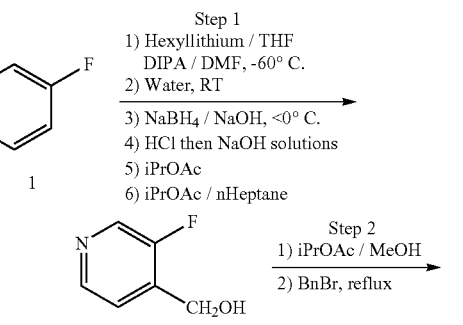

Step 2
1) iPrOAc / MeOH
2) BnBr, reflux

Step 3
1) MeOH
2) NaBH4 / NaOH, 0° C.
3) iPrOAc
4) NaCl aq, RT
5) HCl / MeOH, 55° C.
6) iPrOAc / MeOH, 5 C.
7) Darco G 60
8) iPrOAc / MeOH, <40° C.

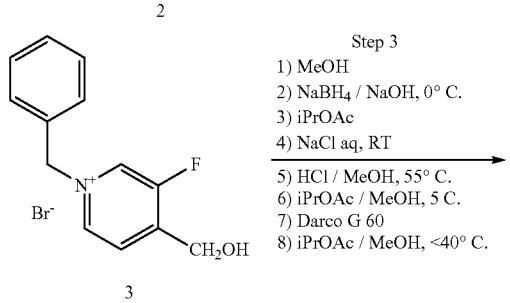

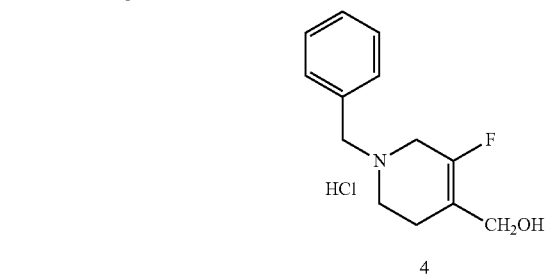

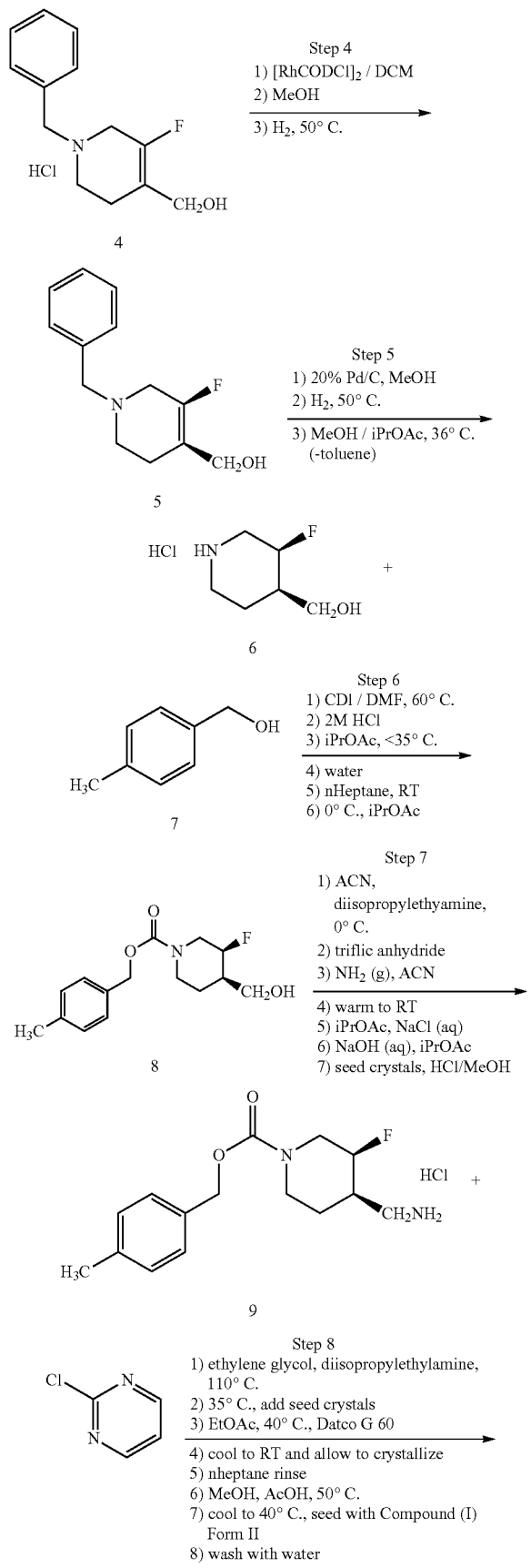

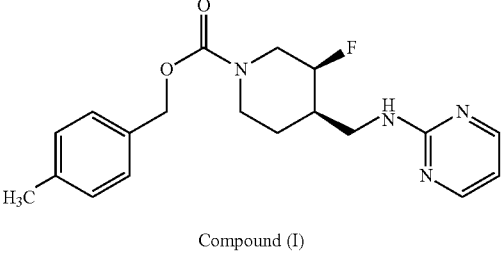

Compound (I)

Abbreviations used herein denote the following:
ACN=acetonitrile
AcOH=acetic acid
BnBr=benzyl bromide
CDI=1,1'-carbonyldiimidazole
Darco G=activated charcoal
DCM=dichloromethane
DIPA=diisopropylamine
DMT=dimethylformamide
EtOAc=ethyl acetate
HCl=hydrogen chloride
iProAc=isopropyl acetate
MeOH=methanol
$NaBH_4$=sodium borohydride
NaCl=sodium chloride
NaOH=sodium hydroxide
$NH_3$=ammonia
Pd/C=palladium on carbon
$[RhCODCl]_2$=chloro(1,5-cyclooctadiene)rhodium (I) dimer (also known as 1,5-cyclooctadienerhodium (I) chloride dimer, bis(1,5-cyclooctadiene)dirhodium (I) dichloride, di-µ-chlorobis[(1,2,5,6-η)-1,5-cyclooctadiene]dirhodium, rhodium (I) chloride 1,5-cyclooctadiene complex dimer, and $[Rh(COD)Cl]_2$)
RT=room temperature
THF=tetrahydrofuran Step 1

Compound 1 was treated with LDA and then reacted with DMF to produce an in situ aldehyde intermediate, which was reduced with $NaBH_4$ to yield Compound 2. Purification of compound 2 was completed by recrystallization.

Step 2

Compound 2 was reacted with benzyl bromide to yield Compound 3.

Step 3

Compound 3 was reduced with $NaBH_4$ to produce Compound 4 as the HCl salt. Purification of Compound 4 was completed by recrystallization.

Step 4

An asymmetric reduction of compound 4 using Walphos under hydrogen atmosphere produced Compound 5.

Step 5

Compound 5 was then deprotected (debenzylated) with a further reduction step using hydrogen over palladium to yield Compound 6.

Step 6

Compound 6 was coupled with 4-methylbenzylalcohol (compound 7) and carbonyldiimidazole to produce Compound 8.

Step 7

Compound 8 was then converted to an in-situ triflate, which was further reacted with ammonia to yield Compound 9.

Step 8

Compound 9 was reacted with chloropyrimidine to produce crude Form I of Compound (I) or 4-methylbenzyl (3S, 4R)-3-fluoro-4-[(pyrimidin-2-ylamino) methyl] piperidine-1-carboxylate. Form I of Compound (I) was seeded with Form II of Compound (I). Purification by slurrying in the presence of Darco G60 followed by recrystallization produced purified Form II, that was co-milled to the desired particle size distribution.

Example 2: X-Ray Powder Diffraction Pattern

Crystalline Form II of Compound (I) was characterized using X-ray powder diffraction (XRPD)(FIG. 1A). The XRPD pattern corresponds to an anhydrous form denoted as Form II, which is highly crystalline. In addition to Form II, Compound (I) can exist as another anhydrous polymorph, denoted as Form I. The XRPD patterns of these phases are shown in FIG. 1B. A slurry experiment was performed at room temperature by adding approximately equal proportions of the two anhydrous phases to methyl-tert-butyl ether. The XRPD of the filtered solids from the slurry showed phase conversion to Form II. XRPD analysis of solids recovered from heating Form I to 115° C. showed phase conversion to Form II. Based on these experiments, Form II is the thermodynamically stable form between room temperature and 121° C.

Example 3: Ultraviolet Absorbance Spectrum

The ultraviolet (UV) absorbance spectrum of crystalline Form II of Compound (I) shown in FIG. 2 was obtained using a Cary 300 Bio UV-Vis spectrophotometer and methanol as diluent. The spectrum is characterized by maxima at 236±2 nm.

Example 4: Infrared Transmittance Spectrum

The infrared (IR) transmittance spectrum of crystalline Form II of Compound (I), shown in FIG. 3, was obtained with the ATR accessory using a Nicolet Nexus 670 FTIR spectrometer.

Example 5: Proton Nuclear Magnetic Resonance Spectrum

The proton nuclear magnetic resonance CH NMR) spectrum of crystalline Form II of Compound (I), shown in FIG. 4, was obtained using a Bruker DRX-600 nuclear magnetic resonance (NMR) spectrometer operating at a frequency of 600.13 MHz. The sample concentration was approximately 3.1% (w/v) in $CD_3CN$. The reference compound was $CHD_2CN$ (1.94 ppm). The spectrum was obtained at 0° C. to sharpen signals that were broad at ambient temperature. Signal assignments following the numbered structural formula of Compound (I) below are provided in Table 1.

(I)

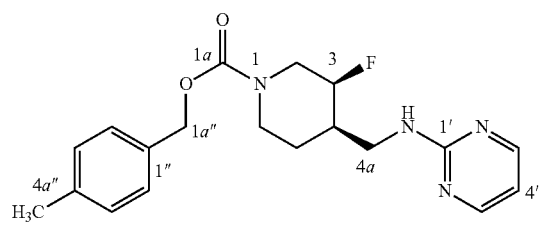

TABLE 1

$^1$H NMR Signal Assignments

| $\delta_H$ (ppm) | Multiplicity* | Assignment[†, #, $] |
|---|---|---|
| 8.24 | d, J~4 | $C_{3'}H$, $C_{5'}H$ |
| 7.24 | o m | $C_{2''}H$, $C_{6''}H$ |
| 7.17 | o m | $C_{3''}H$, $C_{5''}H$ |
| 6.54 | t, J = 4.8 | $C_{4'}H$ |
| 6.11 | br t, J~6 | NH |
| 5.03 | o m | $C_{1a''}H$ |
| 4.78 | br d, $J_{HF}$-48.0 | $C_3H$ (rotamer) |
| 4.73 | br d, $J_{HF}$-47.9 | $C_3H$ (rotamer) |
| 4.34 | o m | $C_2H$ |
| 4.15 | o m | $C_6H$ |
| 3.33 | o m | $C_{4a}H_2$ |
| 2.99-2.73 | o m | $C_2H$, $C_6H$ |
| 2.31 | s | $C_{4a''}H_3$ |
| 2.00 | o m | $C_4H$ |
| 1.54 | o m | $C_5H$ |
| 1.45 | o m | $C_5H$ |

*Multiplicity: s = singlet; d = doublet; br = broad; t = triplet; m = multiplet; o = overlapped; J = coupling constant in Hertz.
[†]In solution, L-001067743-005K exists as a 1:1 mixture of carbamate rotamers. Assignments are grouped except where noted by: (rotamer).
[#]The signal at 2.26 ppm is due to $H_2O$.
[$]A multiplet at 3.36 ppm is assigned to a low-level unknown.

Example 6: $^{13}$C Nuclear Magnetic Resonance Spectrum

The $^{13}$C nuclear magnetic resonance ($^{13}$C NMR) spectrum of crystalline Form II of Compound (I) shown in FIG. 5 was obtained using a Bruker DRX-600 NMR spectrometer operating at a frequency of 150.90 MHz. The sample concentration was approximately 3.1% (w/v) in $CD_3CN$. The reference compound was $CD_3CN$ (1.39 ppm for the $CD_3$ group; the —CN group was observed at 118.45 ppm). The spectrum was obtained at 0° C. to sharpen signals that were broad at ambient temperature. Signal assignments following the numbered structural formula of Compound (I) below are provided in Table 2.

(I)

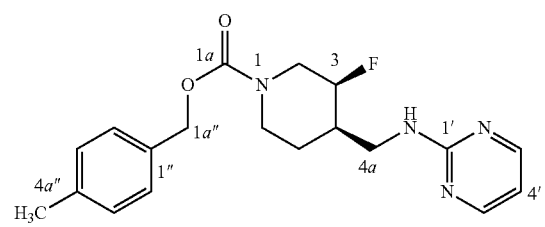

TABLE 2

$^{13}$C NMR Signal Assignments

| δc (ppm) | Assignment* | δc (ppm) | Assignment* |
|---|---|---|---|
| 163.56 | $C_{1'}$ | 87.69, d, $J_{CF}$ = 174.1 | $C_3$ (rotamer) |
| 158.9 (broad) | $C_{3'}$, $C_{5'}$ | 67.46, 67.36 | $C_{1a''}$ |
| 156.29, 156.25 | $C_{1a}$ | 48.40, d, $J_{CF}$ = 20.7 | $C_2$ (rotamer) |
| 138.75, 138.71 | $C_{4''}$ | 48.16, d, $J_{CF}$ = 20.7 | $C_2$ (rotamer) |
| 135.13 | $C_{1''}$ | 44.06, 43.90 | $C_6$ |
| 129.96 | $C_{3''}$, $C_{5''}$ | 43.09, d, $J_{CF}$ = 2.7 | $C_{4a}$ |
| 128.89, 128.78 | $C_{2''}$, $C_{6''}$ | 39.22, d, $J_{CF}$ = 20.3 | $C_4$ |
| 111.34 | $C_{4'}$ | 24.58, 24.38 | $C_5$ |
| 87.88, d, $J_{CF}$ = 174.3 | $C_3$ (rotamer) | 21.15 | $C_{4''}$ |

Example 7: Thermogravimetric Analysis Curve

The thermogravimetric (TG) analysis curve for Form II of Compound (I) was obtained under nitrogen flow at a heating rate of 10° C. per minute. A weight loss of 0.04% was observed up to 150° C. (FIG. 6). Further weight loss above 150° C. was attributed to decomposition.

Example 8: Differential Scanning Calorimetry

The differential scanning calorimetry (DSC) curve for Form II of Compound (I) was obtained under nitrogen flow at a heating rate of 10° C. per minute in a crimped pan (FIG. 7). The DSC curve displayed a melting endotherm with extrapolated onset temperature of 121° C., a peak temperature of 123° C., and a heat of fusion of 112.7 J/g.

Example 9: Particle Size Evaluation

Samples of micronized crystalline Form II of Compound (I) were evaluated for particle size and development of particle size analysis method.

Particle size information was obtained using a Sympatec HELOS/KF particle size analyzer equipped with RODOS/M dispersion module, VIBRI vibratory feeder and an R2 lens (upper limit=87.5 microns). 100±10 mg sample of micronized Form II of Compound (I) was transferred to the VIBRI and spread evenly to sure a consistent feed rate. Analysis was conducted using a feed rate of 25% and a feed pressure of 3.0 bar. Trigger conditions were as follows: timebase-100 ms; start-c.opt ≥1.0%; valid-always; stop-5 s, c.opt ≤1.0% or 10 s real time. The data was analyzed using Sympatec's WINDOX 5 software. The results are provided in Table 3.

TABLE 3

X10, X50 and X90 Particle Size of Micronized Form II

| | Analysis 1 | | | Analysis 2 | | |
|---|---|---|---|---|---|---|
| Replicate | X10 (μm) | X50 (μm) | X90 (μm) | X10 (μm) | X50 (μm) | X90 (μm) |
| 1 | 0.78 | 1.90 | 4.41 | 0.79 | 1.93 | 4.45 |
| 2 | 0.79 | 1.93 | 4.43 | 0.80 | 1.95 | 4.63 |
| 3 | 0.79 | 1.92 | 4.46 | 0.79 | 1.92 | 4.42 |
| 4 | 0.78 | 1.98 | 4.75 | 0.79 | 1.93 | 4.43 |
| 5 | 0.79 | 1.94 | 4.62 | 0.79 | 1.93 | 4.60 |
| 6 | 0.79 | 1.95 | 4.48 | 0.79 | 1.91 | 4.42 |
| Average | 0.79 | 1.94 | 4.53 | 0.79 | 1.93 | 4.49 |
| Standard Deviation | 0.01 | 0.03 | 0.13 | 0.00 | 0.01 | 0.10 |
| % Relative Standard Deviation | 1.27 | 1.55 | 2.87 | 0.00 | 0.52 | 2.23 |

Based on the development studies, the method parameters considered suitable for routine particle size analysis of micronized Compound (I) samples are set forth below:

| | | | |
|---|---|---|---|
| Calculation Mode: | HRLD | Trigger Conditions: | |
| Sample Mass: | 100 ± 25 mg | Timebase: | 100 ms |
| Feeder: | VIBRI | Start: | c.opt ≥1.0% |
| Dispenser: | RODOS/M | Valid: | always |
| Feed Pressure: | 3.0 bar | Stop: | 5 s, c.opt ≤1.0% or 10 s real time |
| Feed Rate: | 25% | Lens: | R2 (upper limit 87.5 microns) |

Example 10: Effect of Particle Size on Drug Absorption

To test the particle size (PS) effect on absorption, monkey studies were conducted at a 90-mg/kg dose to compare the unmilled and jet-milled Compound (I) as suspensions in 0.5% methocel. Male Rhesus monkeys were administered unmilled and jet-milled crystalline Form II of Compound (I) as suspensions in 0.5% methocel at a dose of 90 mg/kg. The monkeys were fed approximately one hour prior to dosing. As shown in Table 4, the jet-milled Form II with a mean PS of 4.5 μm increased drug exposure by 1.43 fold vs. the unmilled Form II with a mean PS of 14 μm.

TABLE 4

Particle Size Effect in Fed Male Rhesus Monkeys*

| Mean parameters | Particle size** (μm) | Surface area (m²/g) | $AUC_{0-24}$ (μM*hr) | Cmax (μM) | Tmax (hr) |
|---|---|---|---|---|---|
| Jet-milled Form II | 4.5 | 2.3 | 119.3 ± 20.9 | 9.70 ± 3.00 | 6.67 ± 1.20 |
| Unmilled Form II | 14 | 1.5 | 83.7 ± 14.9 | 6.53 ± 2.76 | 3.33 ± 1.15 |

*The monkeys were fed 10 biscuits approximately one hour prior to dosing.
**PS was measured using bulk drug powder.

Example 11: Affinity for NMDA-GluN2B Receptors

Radioligand binding assays were performed at room temperature (or 37° C.) in 96-well microtiter plates with a final assay volume of 1.0 mL in 20 mM HEPES buffer (pH 7.4) containing 150 mM NaCl. Crystalline Form II of Compound (I) was prepared at 10 mM in dimethylsulfoxide (DMSO) and serially diluted with DMSO to yield 20 μL of each of 10 solutions differing by 3-fold in concentration (Mosser et al., 2003). Nonspecific binding was assessed using N-(3-chlorobenzyl)-4-iodobenzimidamide (final concentration, 10 μM), and total binding was measured by addition of DMSO (final concentration, 2%). L(tk-) cell membranes expressing human GluN1a/GluN2B receptors (final concentration, 40 μM) and [$^3$H]-[(E)-N1-(2-methoxybenzyl)-cinnamamidine] (final concentration, 1 nM) were added to all wells of the microtiter plate. After 3 h (24 h or 48 h) of incubation at room temperature (or 37° C.), samples were filtered through Packard GF/B filters (presoaked in 0.05% polyethylenimine [PEI; Sigma P-3143]) and washed 10 times with 1 mL of cold 20 mM HEPES buffer per wash. After vacuum drying of the filter plates, 50 μL of Packard Microscint-20 was added and the bound radioactivity determined in a Packard TopCount.

Analogous binding experiments, to those described above for the cloned human receptor expressed in L(tk-) cells, were also performed using whole brain homogenate (rat), frontal cortex homogenate (dog and rhesus monkey), and temporal cortex homogenate (human).

Form II potently inhibited radioligand ([$^3$H]Compound-2) binding to human NMDA-GluN1a/GluN2B receptors expressed in L(tk-) cells as well as brain tissue homogenates from all tested species (rat, dog, rhesus monkey, human). The binding affinity of Form II determined using human temporal cortex homogenate yielded $K_i$ values of 3.1 nM (0.0031 μM) and 8.1 nM (0.0081 μM) at room temperature and 37° C., respectively. Findings in other species were consistent with the human data (Table 5).

TABLE 5

Binding Affinities to Expressed Human GluN1a/GluN2B Receptors in L (tk-) Membranes and Brain Tissue Homogenates

| Species | $K_i$ (nM) 4° C. | $K_i$ (nM) Room Temp. | $K_i$ (nM) 37° C. |
|---|---|---|---|
| Human GluN1a/GluN2B in L (tk-) | 1.8 | 4.9 | 31 |
| Human Temporal Cortex | — | 3.1 | 8.1 |
| Rhesus Frontal Cortex | — | 3.1 | 14 |
| Dog Frontal Cortex | — | 3.2 | 13 |
| Rat Brain Homogenate | — | 3.3 | 14 |

Values are geometric means.

Example 12: Functional Activity and Selectivity for NMDA Receptors

The inhibition of calcium influx into L(tk-) cells expressing either GluN1a/GluN2B or GluN1a/GluN2A human receptors was measured to determine the $IC_{50}$ of Compound (I) inhibition of NMDA receptor functions.

GluN1a/GluN2B (or GluN1a/GluN2A) receptor-transfected L(tk-) cells were plated in 96-well format at $3 \times 10^4$ cells per well and grown for 1 day in normal growth medium (Dulbecco's modified Eagle medium with Na pyruvate, 4500 mg glucose, penicillin/streptomycin, glutamine, 10% fetal calf serum, and 0.5 mg/mL geneticin). GluN1a/GluN2B (GluN1a/GluN2A) expression in these cells was induced by the addition of 10 nM dexamethasone in the presence of 500 μM ketamine for 16-24 h. Crystalline Form II of Compound (I) was prepared in DMSO and serially diluted with DMSO to yield 10 solutions differing by 3-fold in concentration. A 96-well drug plate was prepared by diluting the DMSO solution 250-fold into assay buffer ($Mg^{2+}$-free Hanks Balanced Salt Solution containing 20 mM HEPES, 2 mM $CaCl_2$, 0.1% bovine serum albumin, and 250 probenecid). After induction, the cells were washed twice (Labsystem cell washer; 3-fold dilutions leaving 100 μL) with assay buffer and loaded with the calcium fluorescence indicator fluo-3 AM (4 μM) in assay buffer containing Pluronic F-127 and 100 μM ketamine at 37° C. for 1 h. The cells were then washed 8 times with assay buffer leaving 100 μL of buffer in each well. Fluorescence intensity was immediately measured in a FLIPR (Fluorometric Imaging Plate Reader; Molecular Devices, Sunnyvale, Calif.) using an excitation of 488 nm and emission at 530 nm. Five seconds after starting the recording of fluorescence intensity, 50 μL of agonist solution (40 μM glutamate/glycine; final concentration, 10 μM) was added, and after 1 min, when the fluorescence signal was stable, 50 μL of Form II and control solutions from the drug plate were added and the fluorescence intensity recorded for another 30 min.

Form II inhibited calcium influx into agonist-stimulated NMDA-GluN1a/GluN2B L(tk-) cells with an $IC_{50}$ of 3.6 nM (0.0036 μM) but had no effect on calcium influx into agonist-stimulated NR1a/NR2A cells at concentrations up to 30,000 nM (30 μM). The results demonstrate that Form II is a potent, highly selective antagonist of NMDA receptors containing the GluN2B subunit.

Example 13: Single-Dose Pharmacokinetics in Rats and Monkeys (Oral and IV)

Male Sprague-Dawley rats (N=8; N=4 oral and N=4 intravenous [IV]) weighing approximately 250-280 g and male rhesus monkeys (N=4, crossover) weighing 6.0-8.8 kg were used for the PK studies. In rats, the IV dose of crystalline Form II of Compound (I) at 2 mg/kg (0.4 mL/kg) was administered as a bolus and the oral dose was administered by gavage at 15 mg/kg (5 mL/kg). In monkeys, the IV dose of Form II at 2 mg/kg (0.1 mL/kg) was administered as a slow bolus and the oral dose was administered via nasogastric tube at 15 mg/kg (5 mL/kg). Blood samples were serially collected pre-dose, and at 0.083 (IV only), 0.25, 0.50, 1, 2, 4, 6, 8, 10, 24, 48, 72, and 96 h post-dose. The concentrations of Form II in rat and monkey plasma were determined by LC/MS/MS analysis in the positive ion mode using a heated nebulizer interface. The lower limit of quantitation was 2.5 ng/mL (approximately 0.00697 μM).

PK parameters are summarized in Table 6. After oral administration to both rats and monkeys, Form II was rapidly absorbed (Tmax <1 h for rats and approximately 2 h for monkeys) and exhibited good bioavailability in both species (60% in rats and 50% in monkeys). Volume of distribution (Vdss) was estimated after IV administration and exceeded total body water in rats (mean Vdss=3.1 L/kg) and was moderate in monkeys (mean Vdss=2.9 L/kg). High total plasma clearance (CLp) was exhibited after IV administration in both species (mean CLp=28.4 mL/min/kg in rats and 15.1 mL/min/kg in monkeys). Half-life (t½), which was calculated after the IV dose, was longer in monkeys (mean t½=4.2 h) compared to rats (mean t½=1.7 h).

TABLE 6

Pharmacokinetics in Rats and Monkeys during Oral (PO) and Intravenous (IV) Administration at Doses of 2 and 15 mg/kg

| Parameter[a] | Rat (N = 4) | Monkey (N = 4) |
|---|---|---|
| IV Dose (mg/kg) | 2 | 2 |
| $AUC_{(0-\infty)}$ (μM · h) | 3.31 (0.41) | 6.67 (2.12) |
| $CL_p$ (mL/min/kg) | 28.4 (3.4) | 15.1 (4.8) |
| $Vd_{ss}$ (L/kg) | 3.1 (0.3) | 2.9 (2.5) |
| $t_{1/2}$ (h) | 1.7 (0.4) | 4.2 (3.7) |
| PO Dose (mg/kg) | 15 | 15 |
| $AUC_{(0-\infty)}$ (μM · h) | 14.9 (2.1) | 25.1 (11.9) |
| $C_{max}$ (μM) | 5.9 (1.1) | 3.6 (1.3) |
| $T_{max}$ (h) | 0.44 (0.1) | 2.1 (1.4) |
| Bioavailability (%) | 60[b] | 50 (12)[c] |

[a]Data are presented as mean (S.D.)
[b]Based on AUC0-∞☐(dose normalized) values after IV and PO dosing (non-crossover study design).
[c]Based on AUC0-∞☐(dose normalized) values after IV and PO dosing (crossover study design).
AUC, area under the curve;
$CL_p$, total plasma clearance;
$C_{max}$, maximum plasma concentration of drug;
$T_{max}$, time to $C_{max}$;
$t_{1/2}$, half-life;
$Vd_{ss}$, volume of distribution at steady state.

Example 14: Acute Depression Model—Forced Swim Test

Young, adult, male Sprague-Dawley rats were randomly assigned across the treatment groups and were administered vehicle (0.5% MC/0.02% SLS), the reference compound desipramine (20 mg/kg; a tricyclic antidepressant; Sigma, Lot #078K1326) dissolved in sterile water, or crystalline Form II of Compound (I) (0.1, 0.3, 1, 3, 10, and 30 mg/kg) suspended in 0.5% MC/0.02% SLS, twice on Day 1 (after habituation; ~24 h prior to test, and prior to dark cycle) and once on Day 2 (30 min pre-test for desipramine and 45 min pre-test for Form II and vehicle).

Each Forced Swim chamber was constructed of clear acrylic (height, 40 cm; diameter, 20.3 cm). Rats were subjected to a pre-dose swim test of one 15-min session in cylinders containing water at 23° C.±1° C., followed approximately 24 h later by the experimental 5-min session. The water level was 16 cm deep during habituation and 30 cm deep during the test. Immobility, climbing, and swimming behaviors were recorded every 5 s for a total of 60 counts per subject. When an animal was unable to maintain a posture with its nose above water, it was immediately removed from the water and eliminated from the study. Blood was collected at the completion of swim test procedures and plasma was analyzed for Form II concentrations.

Form II (1, 3, 10, and 30 mg/kg) significantly decreased immobility frequency (P<0.001) and significantly increased swimming behavior (P<0.01 for 1, 3, and 30 mg/kg; P <0.05 for 10 mg/kg) compared to the vehicle control (FIG. 8), but did not affect climbing behavior except at the dose of 3 mg/kg (P<0.05). Desipramine (20 mg/kg) significantly decreased immobility (P<0.001) and significantly increased climbing behavior (P<0.01) compared to the vehicle control, with no change in swimming behavior. Form II plasma levels were approximately 15, 120, 390, 1420, 4700, and 14110 nM at the time of sampling, corresponding to approximately 5, 29, 56, 83, 94, and 98% RO, respectively, in rats. The $ED_{50}$ for increase in frequency of swimming and decrease in immobility were ~0.3 and 0.7 mg/kg, respectively, corresponding to RO of ~30% and 50%.

Example 15: Acute Depression Model—Locomotor Assay

To confirm that the effect of Form II in the forced swim test was not due to a general increase in activity levels, rats were subjected to a locomotor assay following oral Form II administration. Adult male Sprague-Dawley rats (N=42) were randomly assigned across the treatment groups (vehicle or Compound (I) at 0.1, 0.3, 1, 3, 10, and 30 mg/kg; N=6/group). Locomotor activity was assessed during the light cycle in photocell-monitored cages (Hamilton Kinder, San Diego, Calif.). Each cage consisted of a standard plastic rat cage (24×45.5 cm) surrounded by a stainless steel frame. Infrared photocell beams were located across the long axis of the frame to measure the ambulatory distance traveled. A second set of beams was placed above the floor and was used to measure rearing activity. Photocell beam interruptions were recorded by a computer system. Filter tops were placed on top of the test enclosures during testing. Rats were administered either vehicle or test compound via oral gavage twice on Day 1 (approximately 24 h before the test and prior to dark cycle) and once on Day 2 (45 min prior to placing in the locomotor cages for a 60-min test). Locomotor activity was captured in 5-min bins.

Figure 8:
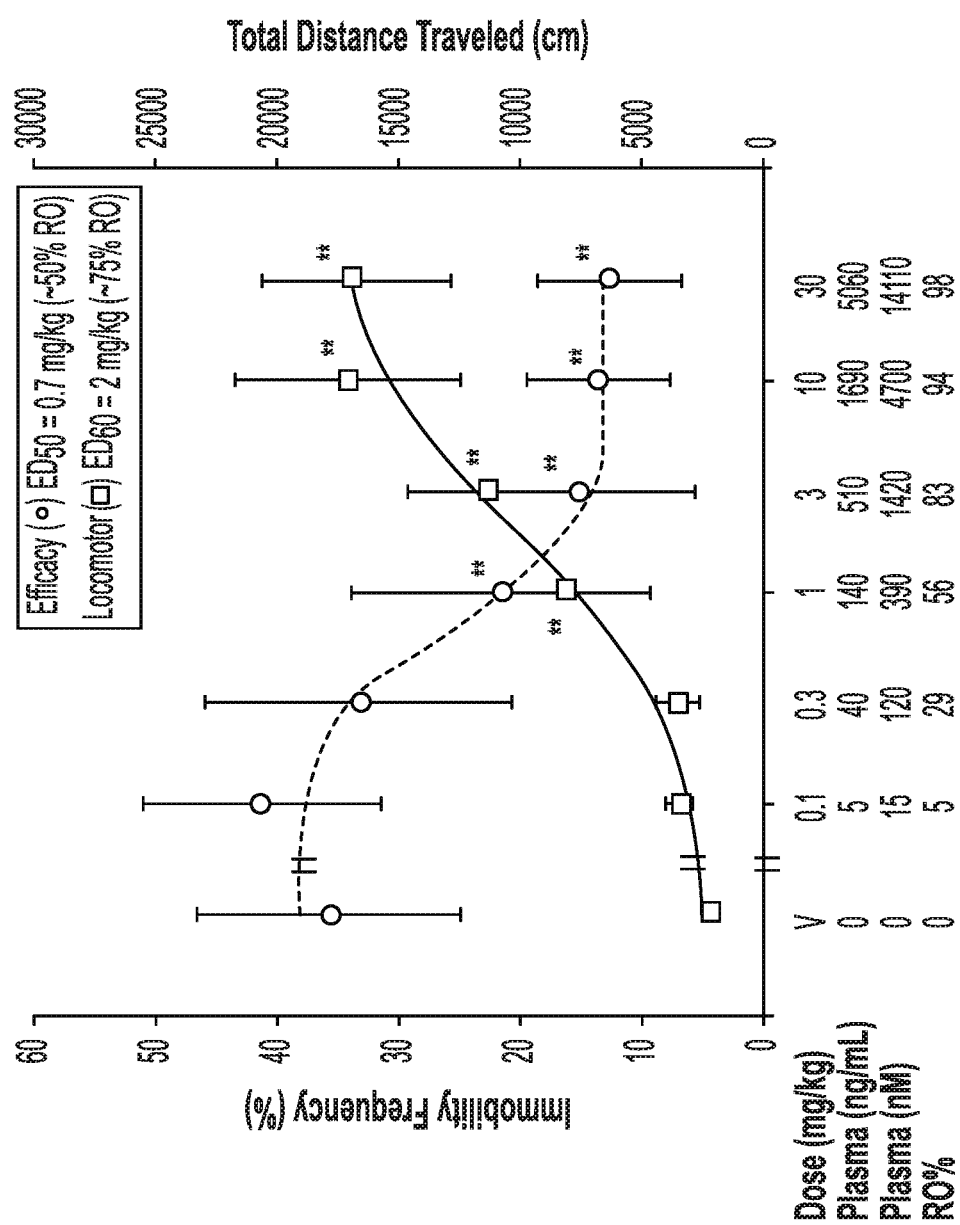
FIG. 8 shows the dose response curve for antidepressant effects of crystalline Form II of Compound (I) relative to its locomotor effect in rats.

Form II (1, 3, 10, and 30 mg/kg) significantly increased distance traveled (P<0.01 for 1 and 3 mg/kg; P<0.001 for 10 and 30 mg/kg) compared to vehicle control during the first 5 min of testing (timing correlates with time of forced swim test). Form II (1, 3, 10, and 30 mg/kg) significantly increased total distance traveled (P<0.01 for 1 mg/kg; P<0.001 for 3, 10, and 30 mg/kg) compared to vehicle control summed over the 60-min test. The $ED_{50}$ for increase in locomotor activity was ~2 mg/kg, translating to an RO of ~75%, which is higher than the $ED_{50}$ for increase in frequency of swimming and decrease in immobility. No locomotor effects were observed for the 0.1 and 0.3 mg/kg dose groups (FIG. 8).

Example 16: Blood Pressure Profile in Chronically Instrumented Rats

Six (n=6) rats were used to study the effect of crystalline Form II of Compound (I) on systemic blood pressure and heart rate. A single oral gavage dose was administered (volume: 5 mL/kg). Prior to dosing, a 24 hours baseline was recorded. The effect of crystalline Form II of Compound (I) was recorded for 24 hours. A Latin square was performed on using 3 doses of crystalline Form II of Compound (I) (0.3, 1, and 3 mg/kg) and corresponding vehicle (n=6 per group). Following the completion of the Latin square, two additional dose concentrations were evaluated (0.6 and 10 mg/kg, n=3 per group).

Three (3) rats were used to study the effect of MK-801 (dizocilpine). On day 1, baseline readings were recorded for 24 hours prior to dosing. On day 2, the rats were administered a single intravenous (tail vein) bolus of 0.9% saline (volume ~0.2 mL) and monitored continuously (via telemetry) for at least 24 hours. On day 3, the rats were administered a single intravenous (tail vein) bolus of MK-801 (200 µg/kg; volume ~0.2 mL) and monitored continuously (via telemetry) for at least 24 hours.

In order to investigate a potential mechanism of crystalline Form II of Compound (I), crystalline Form II of Compound (I) was administered in combination with different pharmacological inhibitors. Atenolol (β1 blocker, 1 mg/kg, IV bolus) and prazosin (α1 adrenergic receptor antagonist, 200 µg/kg, IV bolus) were administered 30 minutes prior to crystalline Form II of Compound (I) (1 mg/kg). All IV doses were administered in manually restrained rats via tail vena-puncture. It should be noted that vehicle controls were also administered.

Figure 9:
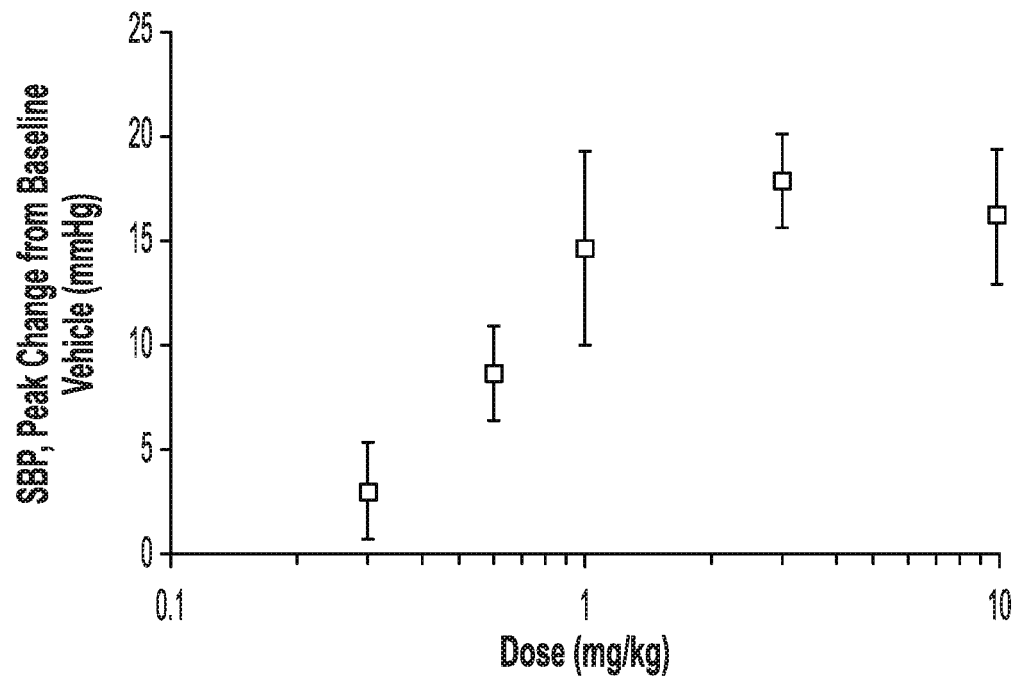
FIG. 9 shows the dose response curve for hypertensive effects of crystalline Form II of Compound (I) in rats.

One hour following a single oral gavage dose, crystalline Form II of Compound (I) elicited a dose-dependent increase in mean arterial pressure (MAP) (4.2±0.9, 6.8±1.2, 15.7±3.2, 17.1±2.3, and 19.1±2.4 mmHg for 0.3, 0.6, 1, 3, and 10 mg/kg respectively). Heart rate (HR) also increased over the dose ranges, however, the dose-dependency of these effects was not evident, as markedly larger but similar effects were noted at 3 and 10 mg/kg (i.e., 15±10 and 10±15, and 34±13 bpm at 0.3, 0.6, and 1 mg/kg vs. 66±9, and 71±25 bpm at 3 and 10 mg/kg) (FIG. 9). Thus, crystalline Form II of Compound (I) (when given orally as a single-dose) elicited hemodynamic responses consistent (albeit markedly to a lower extent) with those seen for MK-801, a well-established NMDA antagonist. The latter finding was unexpected for crystalline Form II of Compound (I).

Rat activity (recorded via telemetry) followed a similar trend as the heart rate response. That is, the 3 and 10 mg/kg doses had much larger effects than the lower doses (0.012±0.025, 0.003±0.033, and 0.049±0.037 at 0.3, 0.6, and 1 mg/kg versus 0.174±0.048 and 0.232±0.057 at 3 and 10 mg/kg). Interestingly, the hemodynamic changes during the first 3.5 hours post administration were linearly correlated with the level of activity (as estimated from telemetry recordings); in particular, activity was an excellent predictor of HR ($R^2$=0.67), and therefore, the excitatory effects of crystalline Form II of Compound (I) may explain the observed increases in HR (particularly at the higher dose-levels) in rats.

To investigate a potential mechanism of the crystalline Form II of Compound (I)-medicated hemodynamic changes, crystalline Form II of Compound (I) was administered in combination with either atenolol (β1 AR blocker, 1 mg/kg) or prazosin (α1 AR antagonist, 200 µg/kg). As anticipated, atenolol minimally affected MAP (−3.3±3.1 mmHg) but markedly reduced HR (−87±11 bpm), while prasozin reduced MAP (18±2 mmHg) but minimally reduced HR (−9±24 bpm). In these settings (i.e., β1 AR or α1 AR blockade), crystalline Form II of Compound (I) (at 1 mg/kg PO) was administered and the hemodynamic responses were studied 1 hour post dosing. In β1 AR blocked animals, crystalline Form II of Compound (I) (1 mg/kg) had negligible effects in MAP (5.8±4.8 mmHg) and HR (−7±17 bpm) when compared to pre-blockade values (i.e., baseline); however, HR did increase 53±17 bpm post-dosing. Crystalline Form II of Compound (I) (1 mg/kg), in the setting of α1 AR blockade, increased HR (118±20 bpm) but lacked MAP changes (−3.8±2.0 bpm) when compared to pre-blockade values (i.e., baseline); however, MAP did increase (11.3±2.0 mmHg) with dosing.

TABLE 7

Peak systemic hemodynamics changes 1 hour post single oral gavage dose of Crystalline Form II of Compound (I); represented as vehicle subtracted change from time-controlled baseline

| Parameters | Crystalline Form II of Compound (I) | | | | |
|---|---|---|---|---|---|
| | 0.3 mg/kg | 0.6 mg/kg* | 1.0 mg/kg | 3.0 mg/kg | 10 mg/kg* |
| SAP (mmHg) | 4.3 ± 1.2 | 6.3 ± 1.6 | 16.8 ± 3.7 | 19.2 ± 2.4 | 20.7 ± 2.4 |
| DAP (mmHg) | 4.1 ± 0.9 | 7.8 ± 1.1 | 15.2 ± 3.0 | 15.0 ± 2.0 | 17.3 ± 1.9 |
| MAP (mmHg) | 4.2 ± 0.9 | 6.8 ± 1.2 | 15.7 ± 3.2 | 17.1 ± 2.3 | 19.1 ± 2.4 |
| PP (mmHg) | 0.1 ± 1.0 | −1.5 ± 1.4 | 1.4 ± 1.1 | 4.0 ± 0.9 | 3.1 ± 1.3 |
| HR (bpm) | 15 ± 10 | 10 ± 15 | 34 ± 13 | 66 ± 9 | 71 ± 25 |
| Activity (arbitrary unit) | 0.012 ± 0.025 | 0.003 ± 0.033 | 0.049 ± 0.037 | 0.174 ± 0.048 | 0.232 ± 0.057 |

Values are mean ± standard error of the mean (n = 6), *n = 3.

Example 17: Human Pharmacokinetic Study

Twenty-four healthy, young male subjects were assigned to 1 of 3 sequential treatment panels (A, B, and C). For each panel of 8 subjects, 2 subjects received placebo and 6 subjects were administered single ascending oral doses of crystalline Form II of Compound (I) with a minimum 7-day washout between each dose: Panel A (0.1, 0.2, 0.5, 1, and 2 mg); Panel B (2, 4, 8, and 15 mg, and 4 mg with food); and Panel C (15 and 20 mg). Blood samples were collected pre-dose and 0.5, 1, 1.5, 2, 3, 4, 6, 9, 12, 18, 24, 30, 48, and 72 h post dose. Plasma samples were analyzed for Form II concentrations using reversed phase high performance liquid chromatography with tandem mass spectrometric detection (Merck Research Laboratories). The analytical range was 0.5 to 500 nM (0.180 to 180 ng/mL).

Figure 10A:
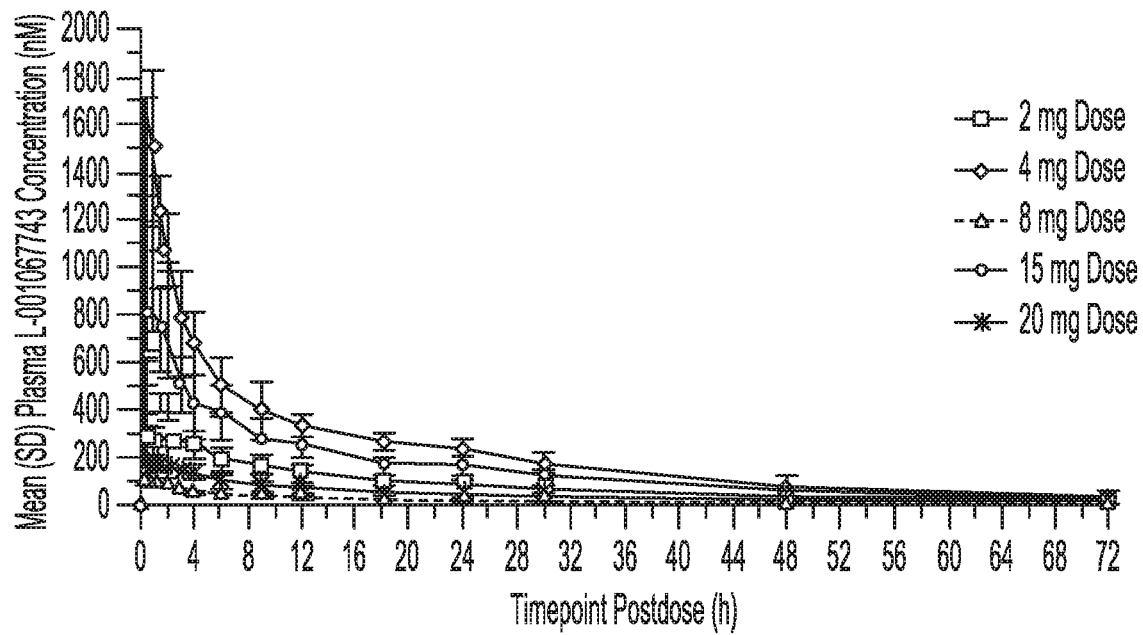
FIG. 10A shows the pharmacokinetic profile (plasma concentrations) of crystalline Form II of Compound (I) in healthy humans in fasted state.
Figure 10B:
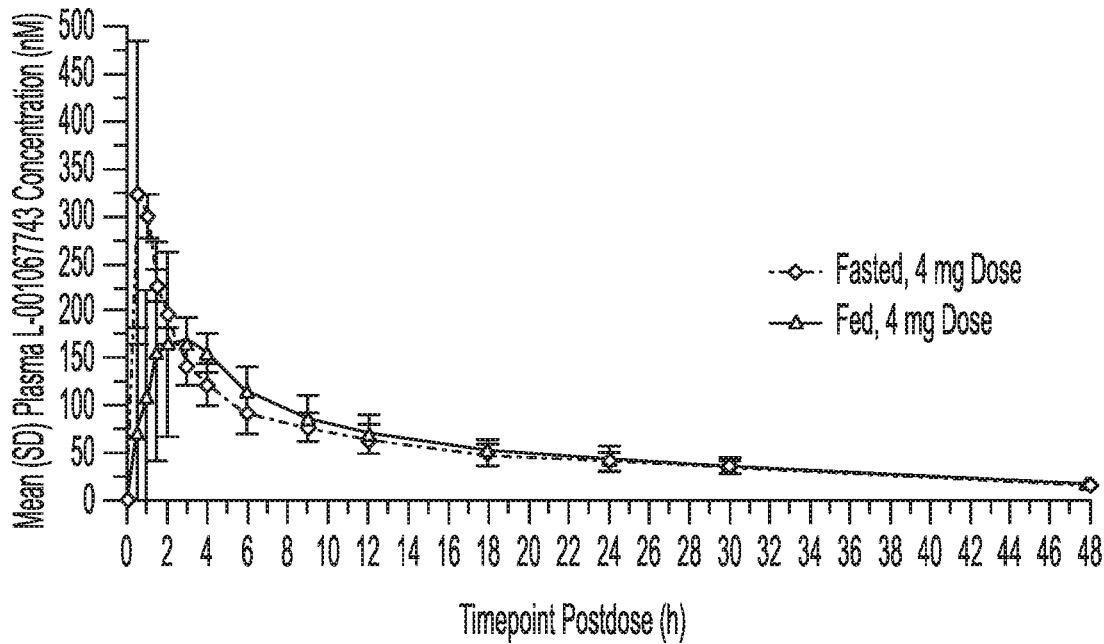
FIG. 10B shows the difference in pharmacokinetics of crystalline Form II of Compound (I) in fed versus fasted state in healthy humans.

Form II was rapidly absorbed (FIG. 10A) with mean $T_{max}$ within 1 h post-dose across all fasted dose levels and terminal elimination half-life ranging from approximately 12 to 17 h over the 4- to 20-mg dose range. $C_{max}$ and AUC behaved in a dose-proportional manner over the dose range studied. The 4-mg dose was administered in the fasted and fed states. Dosing in the fed state led to an approximate 1-h delay in $T_{max}$ and an approximate 56% decrease in $C_{max}$, but the overall extent of absorption (AUC) was not affected (FIG. 10B, Table 8).

pharmacology studies that included an in vitro human ether-a-go-go-related gene (hERG) assay and in vivo studies in rats, dogs, and monkeys. CNS effects were tested in rats at single doses at 15, 75, and 225 mg/kg.

Effects of Form II on the cardiovascular system were tested in several studies. Potential QTc effects were tested in vitro and in vivo. Form II inhibited hERG current in vitro with an $IC_{50}$ of approximately 13 µM (4660 ng/mL). In anesthetized dogs dosed by continuous IV infusion for 90 min at escalating rates, Form II did not affect heart rhythm or any ECG parameter, including QTc interval duration, even though the plasma concentration of Form II at the end of infusion was approximately 74 µM (25450 ng/mL). In conscious, chair-restrained monkeys given single oral doses at 15, 75, and 150 mg/kg and monitored for 6 h post-dose, Form II did not affect heart rhythm or ECG parameters at any dose level, even though the peak plasma concentration was approximately 15 µM (5375 ng/mL) at the highest dose level.

Hemodynamic effects were tested in dogs and monkeys. Form II did not affect heart rate, arterial blood pressure, or femoral blood flow in anesthetized dogs dosed by continuous IV infusion for 90 min at escalating rates. However, Form II did produce dose-independent increases in systolic (12-15 mm Hg), diastolic (7-10 mm Hg), and mean arterial

TABLE 8

Plasma Pharmacokinetic Parameters in Healthy Male Volunteers

| Parameter (unit) | 2 mg (N = 12) | 4 mg (N = 6) | 4 mg (fed) (N = 6) | 8 mg (N = 6) | 15 mg (N = 12) | 20 mg (N = 6) |
|---|---|---|---|---|---|---|
| $C_{max}$ (ng/mL) | 51.47 (16.96) | 140.59 (22.27) | 80.00 (18.46) | 211.93 (42.70) | 385.21 (99.15) | 590.22 (87.09) |
| $T_{max}$ (h) | 1.08 (0.42) | 0.67 (0.26) | 2.00 (1.30) | 0.92 (0.20) | 1.04 (0.33) | 1.00 (0.32) |
| $AUC_{0-t}$ (h*ng/mL) | 397.64 (83.40) | 1063.42 (196.97) | 1080.32 (252.37) | 2151.14 (442.25) | 3521.08 (702.88) | 5593.55 (874.71) |
| $AUC_{0-\infty}$ (h*ng/mL) | 493.25 (101.99) | 1110.27 (200.68) | 1137.98 (261.23) | 2255.09 (473.43) | 4396.45 (966.26) | 5909.82 (1173.62) |
| $t_{1/2}$ (h) | 16.14 (3.12) | 16.92 (1.88) | 17.31 (2.20) | 16.96 (2.10) | 16.79 (4.67) | 15.90 (5.91) |

Data are presented as mean (S.D.)
AUC, area under the curve; $C_{max}$, maximum plasma concentration of drug; $T_{max}$, time to $C_{max}$; $t_{1/2}$, half-life.

Example 18: Safety Pharmacology Studies

The potential effects of Form II of Compound (I) on the functions of the nervous system, cardiovascular system, and respiratory system were evaluated in a battery of safety pressures (9-12 mm Hg) in conscious, chair-restrained monkeys given single oral doses at 15, 75, or 150 mg/kg and monitored for 6 h post-dose. At these dose levels, $C_{max}$ was approximately 3, 9, and 15 µM, (1075, 3225, and 5375 ng/mL), respectively.

Respiratory effects were investigated in rats and dogs. Single oral doses of Form II at 15, 75, and 225 mg/kg produced respiratory stimulation in male rats, reflected in increased respiratory rate, tidal volume, and minute ventilation, and decreased PenH (an index of airway resistance). Respiratory function returned to baseline within 5 to 6 h at 15 mg/kg but remained altered at the end of the 6-h monitoring period at ≥75 mg/kg. In anesthetized dogs dosed at 3 mg/kg by 5-min IV infusion and monitored at intervals for 60 min, Form II did not affect intrapulmonary pressure, peak expiratory flow, airway resistance, lung compliance, tidal volume, respiration rate, or blood pH, $pCO_2$, or $pO_2$. Mean Form II plasma concentration was approximately 30 µM (10600 ng/mL) at the end of infusion and approximately 4 µM (1250 ng/mL) at 60 min post-infusion.

Example 19: Neurotoxicity in Rats

Four groups of 24 Sprague-Dawley rats (12/sex) were given single doses of vehicle (0.5% methylcellulose [MC] and 0.02% sodium lauryl sulfate [SLS] in deionized water) or crystalline Form II of Compound (I) at 10, 30 or 100 mg/kg by oral gavage at a dose volume of 10 mL/kg. An additional group of 12 male rats was given single doses of (5S,10R)-(+)-5-methyl-10,11-dihydro-5H-dibenzo-[a,d]cyclohepten-5,10-imine maleate; NBF, neutral buffered formalin ("MK-801", a non-competitive antagonist of the NMDA receptor; positive control) at 10 mg/kg by subcutaneous injection at a dose volume of 2 mL/kg. Six rats per sex in each group were terminated and necropsied at 4 to 6 h post-dose, and the remaining rats in each group were terminated and necropsied 3 days post-dose (on Day 4). In-life observations and measurements included body weight and clinical observations. At termination, rats were anesthetized and perfusion fixed. At necropsy, the brain was collected for histopathological evaluation.

Animals in Form II and MK-801 assessment groups were terminated at the scheduled necropsy intervals (4-6 h post-dose or Day 4). All animals were anesthetized with an isoflurane/oxygen mixture and perfused via the left cardiac ventricle with heparinized 0.001% sodium nitrite in saline. The saline wash was followed by perfusion of 10% neutral buffered formalin (NBF). Brains were harvested, weighed, and stored in 10% NBF.

The brains were sectioned into 2 mm coronal sections to produce multiple sections in 3 blocks for each animal. The following brain regions were stained: neocortex, paleocortex, basal nuclei, limbic system, thalamus/hypothalamus, midbrain regions, cerebellum, pons region, and medulla oblongata. All brain sections from all animals sacrificed 4 to 6 h after dosing and all animals sacrificed 3 days after dosing were embedded in paraffin, sectioned at 5 µm, stained with hematoxylin and eosin and examined microscopically. For rats sacrificed on Day 4 (3 days after dosing), serial sections from Blocks 1 and 2 were stained with Fluoro-Jade B (a stain increasing the sensitivity of evaluating the brain for neuronal degeneration) and glial fibrillary acidic protein (a stain for astrocyte reactions) and examined microscopically. Three additional groups of rats (4 males and 3 females per group) were orally dosed in the same manner with Form II, and 24-h serial blood samples were obtained and analyzed for Compound (I) plasma concentrations and evaluated for systemic exposure.

There were no Form II-associated morphologic effects at any of the dose levels or time points. In rats, single doses of Form II (10, 30, and 100 mg/kg) did not produce vacuolation or necrosis in all examined regions of the brain. At these doses, mean $C_{max}$ was approximately 4, 14, and 26 µM (1433, 5018, and 9319 ng/mL), respectively. By contrast, all of the MK-801 (10 mg/kg)-dosed animals had vacuolation and necrosis in cingulate gyms neurons, consistent with previous reports (Fix et al., *Brain Res,* 696:194-204 (1995)). At the 4-6 h time point, the animals treated with MK-801 (6 males; Group 5) all had numerous vacuolated neurons in cortical layers 3 and 4 in the cingulate gyms region of the cerebral cortex. The appearance of the MK-801-treated males was completely consistent with previously published descriptions. Affected neurons were characterized by numerous, tightly packed, somewhat distinct, vacuoles filling the cytoplasm. At the 4-6 h time point, none of the vehicle controls and none of the Form II-treated animals had any evidence of cytoplasmic vacuoles in any of the neurons in the cingulate gyms.

On Day 4, all the animals treated with MK-801 (6 males; Group 5) had necrotic neurons in cortical layers 3 and 4 in the cingulate gyms region of the cerebral cortex. The appearance of the MK-801-treated males was completely consistent with previously published descriptions (Fix et al., 1996). Using the Fluoro-Jade B stain, necrotic neurons were easily visualized in all of the Day 4 MK-801-treated animals. In the MK-801-treated animals, sections stained (immunohistochemically) for glial fibrillary acidic protein showed a very slight increase of staining in the region of the cingulate gyms. On Day 4, none of the vehicle controls and none of the Form II-treated animals had any evidence of necrotic neurons in the cingulate gyms.

Example 20: Pharmacodynamic Effects in Healthy Subjects

A randomized, double-blind, placebo-controlled, parallel-dose group in-patient study is conducted to investigate the pharmacodynamic (PD) effects of crystalline Form II of Compound (I) in healthy subjects.

The study is designed as a three-part, sequential study. The sequential nature of the study ensures that a range of doses are investigated first in a young, healthy population (Part 1) before proceeding to higher doses in the healthy population and the comparator populations (intermediate age and elderly) (Parts 2 and 3). For the purposes of this study, "young" refers to a subject who is 18 to 45 years of age, "intermediate age" refers to a subject who is 46 to 64 years of age, and "elderly" refers to a subject who is 65 years of age or older.

Part 1:

After a screening period of up to 21 days (Days −23 to −3), 16 healthy, young male and female subjects are randomly assigned to a dose group as shown in Table 9.

TABLE 9

| Part 1 Parallel Dose Groups (Dosing Days 1-7) | | | |
|---|---|---|---|
| Age | Group* | Study Drug | Dosing Regimen |
| Young | 1 (N = 6) | Crystalline Form II of Compound (I) 8 mg | Two 4-mg tablets + one placebo tablet once-daily with food |
| Young | 2 (N = 6) | Crystalline Form II of Compound (I) 12 mg | Three 4-mg tablets once-daily with food |
| Young | 3 (N = 4) | Placebo | Three placebo tablets once-daily with food |

*Randomization is stratified such that three male subjects and three female subjects are randomized to each dose group.

Note: On Day-1 (time-matched baseline day), all subjects receive placebo in the fed state.

Each parallel dose group is balanced for gender (approximately equal number of males and females). The randomized subjects are domiciled from Day −1 through Day 8. On Day −1, the subjects receive placebo tablets in the fed state and undergo ambulatory blood pressure monitoring (ABPM) and safety assessments to establish time-matched baselines. On Days 1-7, the subjects receive the study drug in the fed state and undergo safety, pharmacokinetic (PK) and pharmacodynamics (PD) assessments. On Days 8-11, follow-up PK and safety assessments are performed.

Safety assessments include Clinician-Administered Dissociative States Scale (CADSS), Columbia-Suicide Severity Rating Scale (C-SSRS), concomitant medication, adverse event (AE) and vital sign assessments. In PK assessments, blood samples are taken and analyzed to determine PK parameters such as $C_{max}$, $T_{max}$, $AUC_{0-24}$, and $t_{1/2}$. PD assessments include ABPM, plasma brain-derived neurotrophic factor (BDNF) measurements, and Profile of Mood States (POMS) assessments. Since BDNF levels have been shown to correlate with the severity of major depressive disorder (MDD) and change in response to antidepressant treatment, BDNF levels are measured in this study as a biomarker of drug activity.

Part 1 Safety Review:

After completion of Part 1, safety data from Day −1 to Day 8 is reviewed. A decision is made to conduct Part 2 or an alternative dosing regimen (e.g., by changing any combination of dose level, dosing interval, and fed state).

Part 2:

After a screening period of up to 21 days (Days −23 to −3), 16 subjects (8 healthy, young male and female subjects, and 8 healthy, intermediate age male and female subjects) are randomly assigned to a dose group as shown in Table 10.

TABLE 10

Part 2 Parallel Dose Groups (Dosing Days 1-7)

| Age | Group* | Study Drug† | Dosing Regimen** |
|---|---|---|---|
| Young | 4 (N = 6) | Crystalline Form II of Compound (I) 16 mg | Four 4-mg tablets once-daily with food |
| Young | 5 (N = 2) | Placebo | Four placebo tablets once-daily with food |
| Intermediate | 6 (N = 6) | Crystalline Form II of Compound (I) 12 mg | Three 4-mg tablets once-daily with food |
| Intermediate | 7 (N = 2) | Placebo | Three placebo tablets once-daily with food |

*Randomization is stratified such that an equal number of males and females are randomized to each dose group.
**The dosing regimen may be changed based on the outcome of the Part 1 safety review. The regimen may be altered by any combination of changing the dose level, dosing interval, or fed state; or repeating a dose level.
†The planned dose level may be changed based on the outcome of Part 1 safety review. The maximum dose in young subjects is 16 mg and the maximum dose in intermediate age subjects is 12 mg Note: On Day −1 (time-matched baseline day), all subjects receive placebo in the fed state.

As in Part 1, the randomized subjects undergo placebo administration in the fed state and time-matched baseline ABPM and safety assessments on Day −1, followed by once-daily dosing of the study drug and pharmacokinetic (PK) and pharmacodynamics (PD) assessments on Days 8-11, and follow-up PK and safety assessments on Days 8-11. Each parallel dose group is balanced for gender (approximately equal number of males and females).

Part 2 Safety Review:

After completion of Part 2, safety data from Day −1 to Day 8 is reviewed. A decision is made to conduct Part 3 or an alternative dosing regimen.

Part 3:

After a screening period of up to 21 days (Days −23 to −3), 16 subjects (8 healthy, young male and female subjects, and 8 healthy, elderly male and female subjects) are randomly assigned to a dose group as shown in Table 11.

TABLE 11

Part 3 Parallel Dose Groups (Dosing Days 1-7)

| Age | Group* | Study Drug† | Dosing Regimen** |
|---|---|---|---|
| Young | 8 (N = 6) | Crystalline Form II of Compound (I) 20 mg | Five 4-mg tablets once-daily with food |
| Young | 9 (N = 2) | Placebo | Five placebo tablets once-daily with food |
| Elderly | 10 (N = 6) | Crystalline Form II of Compound (I) 12 mg | Three 4-mg tablets once-daily with food |
| Elderly | 11 (N = 2) | Placebo | Three placebo tablets once-daily with food |

*Randomization is stratified such that an equal number of males and females are randomized to each dose group.
**The dosing regimen may be changed based on the outcome of the Part 2 safety review. The regimen may be altered by any combination of changing the dose level, dosing interval, or fed state, or repeating a dose level.
†The planned dose level may be changed based on the outcome of Part 2 safety review.

The maximum dose in young subjects is 20 mg and the maximum dose in elderly subjects is 16 mg.

Note: On Day −1 (time-matched baseline day), all subjects receive placebo in the fed state.

As in Parts 1 and 2, the randomized subjects undergo placebo administration in the fed state and time-matched baseline ABPM and safety assessments on Day −1, followed by once-daily dosing of the study drug and pharmacokinetic (PK) and pharmacodynamics (PD) assessments on Days 8-11, and follow-up PK and safety assessments on Days 8-11. Each parallel dose group is balanced for gender (approximately equal number of males and females).

After completion of Part 3, safety data from Day −1 to Day 8 is reviewed. A decision is made as to whether or not to add additional dosing cohorts to investigate alternate dosing regimens or to repeat a regimen.

All data is subsequently analyzed for PD effects, PK profiles, safety and tolerability, as well as age and gender effects on PK, blood pressure and other safety parameters such as AE.

Following repeated daily doses of Crystalline Form II of Compound (I), steady-state predose plasma Crystalline Form II of Compound (I) concentrations were achieved by study day 5. Crystalline Form II of Compound (I) was orally bioavailable with median Tmax values ranged from 2.00 to 3.00 hours on Day 1 and from 1.50 to 3.00 hours on Day 7 of dosing. On Days 1 and 7, Cmax and AUC values increased in an approximately dose-proportional manner over the dose range studied of Crystalline Form II of Compound (I) 8 to 20 mg. Mean plasma Crystalline Form II of Compound (I) concentrations on Day 7 were approximately 20% to 40% higher from 2 to 24 hours postdose in the intermediate age and elderly subgroups, respectively, compared to the young age subgroup, and were approximately 20% higher from 2 to 24 hours postdose in female subjects compared to male subjects.

On Day 7, average t½ ranged from approximately 17 to 25 hours, average apparent oral clearance values ranged from approximately 3 to 4 L/h, and average apparent volume of distribution ranged from approximately 83 to 116 L. Modest accumulation was observed with seven days of daily Crystalline Form II of Compound (I) dosing as the observed accumulation index was approximately 1.6 to 1.9, on average, and steady-state accumulation index was 1.1, on average. Average Day 7 to Day 1 Cmax ratios were 1.3 to 1.4.

Clinically modest differences in PK parameters were observed in intermediate age and elderly subjects compared to young subjects, and in female subjects compared to male subjects. On Day 7, average Cmax values were approximately 30% higher in the intermediate age and elderly subgroups compared to the young age group. On Day 1, average AUC values were approximately 25% to 37% higher in the intermediate age group compared to the young age group and average AUC values were approximately 6% to 29% higher in female subjects compared to male subjects. On Day 7, average AUC values were approximately 48% to 74% higher in the elderly age group compared to the young age group and average AUC values were approximately 19% to 38% higher in female subjects compared to male subjects. On Day 7, apparent oral clearance values were approximately 18% and 30%, on average, lower in the intermediate age and elderly groups, respectively, compared to the young age group and apparent oral clearance values were approximately 15%, on average, lower in female subjects compared to male subjects. On Day 7, average t½ ranged from approximately 20 to 28 hours, and was approximately 27% and 38% higher in the intermediate age and elderly age groups, respectively, compared to the young age group. On Day 7, average t½ ranged from approximately 21 to 24 hours, and was approximately 16% higher in female subjects compared to male subjects.

TABLE 12

Summary of Plasma for Crystalline Form II of Compound (I) Pharmacokinetic Parameters by Dose and Day for Young Subjects

| PK Parameter Statistic | Study Day | CRYSTALLINE FORM 11 OF COMPOUND (1) Dose-Young Subjects By Dose | | | |
|---|---|---|---|---|---|
| | | 8 mg | 12 mg | 16 mg | 20 mg |
| $C_{max}$ (ng/mL) | Day 1 | | | | |
| N | | 6 | 6 | 6 | 6 |
| Mean (SD) | | 179.33 (18.18) | 239.00 (33.36) | 305.83 (31.59) | 383.50 (57.48) |
| Min, Max | | 164, 214 | 209, 294 | 264, 346 | 314, 476 |
| CV % | | 10.14 | 13.96 | 10.33 | 14.99 |
| $C_{max}$ (ng/mL) | Day 7 | | | | |
| N | | 4 | 6 | 6 | 6 |
| Mean (SD) | | 224.00 (30.01) | 273.50 (44.00) | 412.75 (65.06) | 534.33 (97.69) |
| Min, Max | | 191, 260 | 219, 325 | 331, 483 | 365, 628 |
| CV % | | 13.40 | 16.09 | 15.76 | 18.28 |
| $t_{max}$ (h) | Day 1 | | | | |
| N | | 6 | 6 | 6 | 6 |
| Median | | 2.00 | 1.50 | 3.00 | 2.25 |
| Min, Max | | 2.00, 3.03 | 1.00, 3.00 | 1.50, 3.00 | 1.00, 3.00 |
| Mean (SD) | | 2.17 (0.42) | 1.77 (0.70) | 2.58 (0.66) | 2.17 (0.93) |
| CV % | | 19.42 | 39.52 | 25.73 | 42.97 |
| $t_{max}$ (h) | Day 7 | | | | |
| N | | 4 | 6 | 4 | 6 |
| Median | | 3.00 | 2.50 | 1.75 | 1.50 |
| Min, Max | | 2.00, 3.00 | 1.50, 3.00 | 1.50, 2.00 | 1.50, 2.00 |
| Mean (SD) | | 2.75 (0.50) | 2.42 (0.66) | 1.75 (0.29) | 1.67 (0.26) |
| CV % | | 18.18 | 27.50 | 16.50 | 15.49 |
| $AUC_{0-24}$ (h*ng/mL) | Day 1 | | | | |
| N | | 6 | 6 | 6 | 6 |
| Mean (SD) | | 1503.0 (134.7) | 1857.8 (51.9) | 2663.3 (393.9) | 3521.5 (706.6) |
| Min, Max | | 1322.6, 1713.8 | 1777.4, 1906.3 | 2197.0, 3133.1 | 2507.4, 4265.5 |
| CV % | | 8.96 | 2.80 | 14.79 | 20.07 |
| $AUC_{0-24}$ (h*ng/mL) | Day 7 | | | | |
| N | | 4 | 6 | 4 | 6 |
| Mean (SD) | | 2397.7 (262.1) | 3062.5 (512.2) | 4301.2 (1411.2) | 6039.3 (1530.7) |
| Min, Max | | 2107.3, 2688.1 | 2614.4, 3972.0 | 2894.4, 6260.5 | 4087.2, 7880.0 |
| CV % | | 10.93 | 16.72 | 32.81 | 25.35 |
| $AUC_{last}$ (h*ng/mL) | Day 1 | | | | |
| N | | 6 | 6 | 6 | 6 |
| Mean (SD) | | 1488.7 (134.3) | 1835.9 (51.68) | 2631.8 (392.1) | 3476.8 (692.5) |
| Min, Max | | 1308.2, 1699.7 | 1751.6, 1880.6 | 2171.1, 3101.1 | 2481.9, 4206.0 |
| CV % | | 9.02 | 2.82 | 14.90 | 19.92 |
| $AUC_{last}$ (h*ng/mL) | Day 7 | | | | |
| N | | 4 | 6 | 4 | 6 |
| Mean (SD) | | 3770.6 (1355.2) | 5606.7 (1836.0) | 7450.6 (4389.7) | 10132 (3267.1) |
| Min, Max | | 2534.3, 5650.9 | 3680.6, 8885.6 | 3657.8, 13614.4 | 6494.6, 14653.4 |
| CV % | | 35.94 | 32.75 | 58.92 | 32.25 |
| $AUC_{inf}$ (h*ng/mL) | Day 7 | | | | |
| N | | 4 | 6 | 4 | 6 |
| Mean (SD) | | 4109.8 (1398.1) | 5933.1 (2133.5) | 8023.5 (4985.1) | 10468 (3506.7) |
| Min, Max | | 3187.2, 6145.9 | 3824.9, 9805.7 | 3692.1, 14922.9 | 6630.9, 15396.7 |
| CV % | | 34.02 | 35.96 | 62.13 | 33.50 |
| $AUC_{\%extrap}$ (%) | Day 7 | | | | |
| N | | 4 | 6 | 4 | 6 |
| Mean (SD) | | 8.61 (8.27) | 4.77 (2.72) | 5.38 (5.13) | 2.88 (1.30) |
| Min, Max | | 2.84, 20.48 | 1.38, 9.38 | 0.93, 10.77 | 1.62, 4.83 |
| CV % | | 96.11 | 57.15 | 95.36 | 45.18 |

TABLE 12-continued

Summary of Plasma for Crystalline Form II of Compound (I)
Pharmacokinetic Parameters by Dose and Day for Young Subjects

| PK Parameter Statistic | Study Day | CRYSTALLINE FORM 11 OF COMPOUND (1) Dose-Young Subjects By Dose | | | |
|---|---|---|---|---|---|
| | | 8 mg | 12 mg | 16 mg | 20 mg |
| CL/F (L/h) | Day 1 | | | | |
| N | | 6 | 6 | 6 | 6 |
| Mean (SD) | | 5.36 (0.48) | 6.46 (0.18) | 6.12 (0.90) | 5.90 (1.31) |
| Min, Max | | 4.67, 6.05 | 6.29, 6.75 | 5.11, 7.28 | 4.69, 7.98 |
| CV % | | 8.91 | 2.84 | 14.67 | 22.17 |
| CL/F (L/h) | Day 7 | | | | |
| N | | 4 | 6 | 4 | 6 |
| Mean (SD) | | 3.37 (0.37) | 4.00 (0.60) | 4.01 (1.21) | 3.51 (0.97) |
| Min, Max | | 2.98, 3.80 | 3.02, 4.59 | 2.56, 5.53 | 2.54, 4.89 |
| CV % | | 10.99 | 14.98 | 30.30 | 27.69 |
| $V_z/F$ (L) | Day 1 | | | | |
| N | | 6 | 6 | 6 | 6 |
| Mean (SD) | | 101.03 (43.82) | 196.87 (93.73) | 175.02 (104.02) | 147.76 (56.52) |
| Min, Max | | 60.75, 172.75 | 112.49, 376.03 | 64.13, 288.86 | 94.54, 256.58 |
| CV % | | 43.37 | 47.61 | 59.43 | 38.25 |
| $V_{ss}/F$ (h) | Day 7 | | | | |
| N | | 4 | 6 | 4 | 6 |
| Mean (SD) | | 82.60 (25.30) | 115.44 (14.55) | 108.19 (51.29) | 93.18 (19.02) |
| Min, Max | | 49.78, 108.30 | 99.20, 133.36 | 64.42, 182.39 | 76.51, 123.31 |
| CV % | | 30.62 | 12.60 | 47.41 | 20.41 |
| $t_{1/2}$ (h) | Day 7 | | | | |
| N | | 4 | 6 | 4 | 6 |
| Mean (SD) | | 17.22 (6.20) | 20.49 (4.55) | 20.00 (10.22) | 18.75 (2.22) |
| Min, Max | | 10.93, 25.23 | 15.18, 27.02 | 11.35, 31.46 | 16.31, 21.56 |
| CV % | | 35.98 | 22.23 | 51.10 | 11.84 |
| Dose-Normalized $C_{max}$ (ng/mL/mg) | Day 1 | | | | |
| N | | 6 | 6 | 6 | 6 |
| Mean (SD) | | 22.42 (2.27) | 19.92 (2.78) | 19.11 (1.97) | 19.18 (2.87) |
| Min, Max | | 20.50, 26.75 | 17.42, 24.50 | 16.50, 21.63 | 15.70, 23.80 |
| CV % | | 10.14 | 13.96 | 10.33 | 14.99 |
| Dose-Normalized $C_{max}$ (ng/mL/mg) | Day 7 | | | | |
| N | | 4 | 6 | 4 | 6 |
| Mean (SD) | | 28.00 (3.75) | 22.79 (3.67) | 25.80 (4.07) | 26.72 (4.88) |
| Min, Max | | 23.88, 32.50 | 18.25, 27.08 | 20.69, 30.19 | 18.25, 31.40 |
| CV % | | 13.40 | 16.09 | 15.76 | 18.28 |
| Dose-Normalized $AUC_{inf}$ (h*ng/mL/mg) | Day 7 | | | | |
| N | | 4 | 6 | 4 | 6 |
| Mean (SD) | | 513.73 (174.76) | 494.43 (177.79) | 501.47 (311.57) | 523.40 (175.33) |
| Min, Max | | 398.40, 768.23 | 318.70, 817.14 | 230.76, 932.68 | 331.55, 769.83 |
| CV % | | 34.02 | 35.96 | 62.13 | 33.50 |
| Observed Accumulation Index | | | | | |
| N | | 4 | 6 | 4 | 6 |
| Mean (SD) | | 1.58 (0.19) | 1.65 (0.31) | 1.70 (0.54) | 1.71 (0.22) |
| Min, Max | | 1.36, 1.77 | 1.42, 2.23 | 1.26, 2.41 | 1.41, 2.00 |
| CV % | | 12.15 | 18.56 | 31.83 | 12.77 |

TABLE 13

Summary of Plasma for Crystalline Form II of Compound (I) Pharmacokinetic Parameters
by Dose and Day for Young, Intermediate Age and Elderly Subjects at 12 mg Dose

| PK Parameter Statistic | Study Day | CRYSTALLINE FORM II OF COMPOUND (I) Dose | | |
|---|---|---|---|---|
| | | Young 12 mg | Intermediate Age 12 mg | Elderly 12 mg |
| $C_{max}$ (ng/mL) | Day 1 | | | |
| N | | 6 | 6 | 6 |
| Mean (SD) | | 239.00 (33.36) | 257.00 (50.66) | 228.83 (30.73) |
| Min, Max | | 209, 294 | 190, 345 | 174, 260 |
| CV % | | 13.96 | 19.71 | 13.43 |

TABLE 13-continued

Summary of Plasma for Crystalline Form II of Compound (I) Pharmacokinetic Parameters by Dose and Day for Young, Intermediate Age and Elderly Subjects at 12 mg Dose

| | | CRYSTALLINE FORM II OF COMPOUND (I) Dose | | |
|---|---|---|---|---|
| PK Parameter Statistic | Study Day | Young 12 mg | Intermediate Age 12 mg | Elderly 12 mg |
| $C_{max}$ (ng/mL) | Day 7 | | | |
| N | | 6 | 6 | 6 |
| Mean (SD) | | 273.50 (44.00) | 360.33 (64.86) | 349.33 (47.56) |
| Min, Max | | 219, 325 | 247, 432 | 279, 401 |
| CV % | | 16.09 | 18.00 | 13.61 |
| $t_{max}$ (h) | Day 1 | | | |
| N | | 6 | 6 | 6 |
| Median | | 1.50 | 2.50 | 1.75 |
| Min, Max | | 1.00, 3.00 | 1.00, 4.00 | 1.50, 3.00 |
| Mean (SD) | | 1.77 (0.70) | 2.50 (1.05) | 1.93 (0.59) |
| CV % | | 39.52 | 41.95 | 30.46 |
| $t_{max}$ (h) | Day 7 | | | |
| N | | 6 | 6 | 6 |
| Median | | 2.50 | 1.50 | 2.00 |
| Min, Max | | 1.50, 3.00 | 1.00, 3.00 | 1.50, 3.03 |
| Mean (SD) | | 2.42 (0.66) | 1.83 (0.98) | 2.26 (0.62) |
| CV % | | 27.50 | 53.63 | 27.52 |
| $AUC_{0-24}$ (h*ng/mL) | Day 1 | | | |
| N | | 6 | 6 | 6 |
| Mean (SD) | | 1857.8 (51.9) | 2001.2 (400.0) | 2127.2 (438.9) |
| Min, Max | | 1777.4, 1906.3 | 1412.4, 2523.8 | 1503.8, 2612.2 |
| CV % | | 2.80 | 19.99 | 20.63 |
| $AUC_{0-24}$ (h*ng/mL) | Day 7 | | | |
| N | | 6 | 6 | 6 |
| Mean (SD) | | 3062.5 (512.2) | 3841.1 (827.6) | 4516.9 (1022.1) |
| Min, Max | | 2614.4, 3972.0 | 2570.6, 4903.3 | 2934.5, 5958.0 |
| CV % | | 16.72 | 21.55 | 22.63 |
| $AUC_{last}$ (h*ng/mL) | Day 1 | | | |
| N | | 6 | 6 | 6 |
| Mean (SD) | | 1835.9 (51.68) | 1975.8 (395.6) | 2099.4 (431.6) |
| Min, Max | | 1751.6, 1880.6 | 1392.7, 2490.7 | 1488.2, 2580.7 |
| CV % | | 2.82 | 20.02 | 20.56 |
| $AUC_{last}$ (h*ng/mL) | Day 7 | | | |
| N | | 6 | 6 | 6 |
| Mean (SD) | | 5606.7 (1836.0) | 7466.8 (1967.8) | 9143.7 (2972.6) |
| Min, Max | | 3680.6, 8885.6 | 4807.4, 10204.7 | 5123.6, 13850.9 |
| CV % | | 32.75 | 26.35 | 32.51 |
| $AUC_{inf}$ (h*ng/mL) | Day 7 | | | |
| N | | 6 | 6 | 6 |
| Mean (SD) | | 5933.1 (2133.5) | 8104.1 (2270.0) | 10304.0 (3904.9) |
| Min, Max | | 3824.4, 9805.7 | 5116.2, 11320.1 | 5412.3, 16659.1 |
| CV % | | 35.96 | 28.01 | 37.90 |
| $AUC_{\%extrap}$ (%) | Day 7 | | | |
| N | | 6 | 6 | 6 |
| Mean (SD) | | 4.77 (2.72) | 7.51 (1.85) | 9.70 (5.93) |
| Min, Max | | 1.38, 9.38 | 5.08, 9.85 | 2.92, 16.86 |
| CV % | | 57.15 | 24.61 | 61.20 |
| CL/F (L/h) | Day 1 | | | |
| N | | 6 | 6 | 6 |
| Mean (SD) | | 6.46 (0.18) | 6.22 (1.34) | 5.87 (1.32) |
| Min, Max | | 6.29, 6.75 | 4.75, 8.50 | 4.59, 7.98 |
| CV % | | 2.84 | 21.62 | 22.51 |
| CL/F (L/h) | Day 7 | | | |
| N | | 6 | 6 | 6 |
| Mean (SD) | | 4.00 (0.60) | 3.27 (0.80) | 2.79 (0.72) |
| Min, Max | | 3.02, 4.59 | 2.45, 4.67 | 2.01, 4.09 |
| CV % | | 14.98 | 24.62 | 25.75 |
| $V_z/F$ (L) | Day 1 | | | |
| N | | 6 | 6 | 6 |
| Mean (SD) | | 196.87 (93.73) | 201.33 (70.22) | 164.01 (47.57) |
| Min, Max | | 112.49, 376.03 | 147.36, 341.22 | 114.66, 244.64 |
| CV % | | 47.61 | 34.88 | 29.00 |
| $V_{ss}/F$ (L) | Day 7 | | | |
| N | | 6 | 6 | 6 |
| Mean (SD) | | 115.44 (14.55) | 121.40 (23.97) | 110.72 (31.49) |
| Min, Max | | 99.20, 133.36 | 96.43, 159.29 | 77.31, 160.37 |
| CV % | | 12.60 | 19.74 | 28.45 |

TABLE 13-continued

Summary of Plasma for Crystalline Form II of Compound (I) Pharmacokinetic Parameters by Dose and Day for Young, Intermediate Age and Elderly Subjects at 12 mg Dose

| | | CRYSTALLINE FORM II OF COMPOUND (I) Dose | | |
|---|---|---|---|---|
| PK Parameter Statistic | Study Day | Young 12 mg | Intermediate Age 12 mg | Elderly 12 mg |
| $t_{1/2}$ (h) | Day 7 | | | |
| N | | 6 | 6 | 6 |
| Mean (SD) | | 20.49 (4.55) | 26.09 (2.78) | 28.28 (8.11) |
| Min, Max | | 15.18, 27.02 | 22.18, 29.85 | 18.93, 37.88 |
| CV % | | 22.23 | 10.67 | 28.66 |
| Dose-Normalized $C_{max}$ (ng/mL/mg) | Day 1 | | | |
| N | | 6 | 6 | 6 |
| Mean (SD) | | 19.92 (2.78) | 21.42 (4.22) | 29.11 (3.96) |
| Min, Max | | 17.42, 24.50 | 15.83, 28.75 | 23.25, 33.42 |
| CV % | | 13.96 | 19.71 | 13.61 |
| Dose-Normalized $C_{max}$ (ng/mL/mg) | Day 7 | | | |
| N | | 6 | 6 | 6 |
| Mean (SD) | | 22.79 (3.67) | 30.03 (5.40) | 29.11 (3.96) |
| Min, Max | | 18.25, 27.08 | 20.58, 36.00 | 23.25, 33.42 |
| CV % | | 16.09 | 18.00 | 13.61 |
| Dose-Normalized $AUC_{inf}$ (h*ng/mL/mg) | Day 7 | | | |
| N | | 6 | 6 | 6 |
| Mean (SD) | | 494.43 (177.79) | 675.34 (189.17) | 858.67 (325.40) |
| Min, Max | | 318.70, 817.14 | 426.35, 943.34 | 451.02, 1388.25 |
| CV % | | 35.96 | 28.01 | 37.90 |
| Observed Accumulation Index | | | | |
| N | | 6 | 6 | 6 |
| Mean (SD) | | 1.65 (0.31) | 1.92 (0.25) | 2.12 (0.22) |
| Min, Max | | 1.42, 2.23 | 1.73, 2.41 | 1.85, 2.34 |
| CV % | | 18.56 | 12.91 | 10.34 |
| Steady State Accumulation Index | | | | |
| N | | 6 | 6 | 6 |
| Mean (SD) | | 1.01 (0.08) | 1.13 (0.16) | 1.30 (0.11) |
| Min, Max | | 0.92, 1.14 | 0.93, 1.41 | 1.13, 1.46 |
| CV % | | 7.51 | 14.05 | 8.74 |
| Day 7/Day 1 $C_{max}$ Ratio | | | | |
| N | | 6 | 6 | 6 |
| Mean (SD) | | 1.15 (0.18) | 1.41 (0.17) | 1.53 (0.13) |
| Min, Max | | 0.95, 1.42 | 1.25, 1.68 | 1.34, 1.71 |
| CV % | | 15.95 | 11.74 | 8.26 |

TABLE 14

Summary of Plasma for Crystalline Form II of Compound (I) Pharmacokinetic Parameters by Gender and Day for All Crystalline Form II Of Compound (I) Doses Pooled

| PK Parameter Statistic | Study Day | Gender | |
|---|---|---|---|
| | | Males | Females |
| $C_{max}$ (ng/mL) | Day 1 | | |
| N | | 18 | 18 |
| Mean (SD) | | 261.56 (84.47) | 269.61 (66.40) |
| Min, Max | | 168, 476 | 164, 375 |
| CV % | | 32.30 | 24.63 |
| $C_{max}$ (ng/mL) | Day 7 | | |
| N | | 16 | 16 |
| Mean (SD) | | 355.31 (126.67) | 372.94 (107.85) |
| Min, Max | | 210, 628 | 191, 586 |
| CV % | | 35.65 | 28.92 |
| $t_{max}$ (h) | Day 1 | | |
| N | | 18 | 18 |
| Median | | 2.00 | 2.00 |
| Min, Max | | 1.00, 3.03 | 1.00, 4.00 |
| Mean (SD) | | 2.12 (0.72) | 2.26 (0.81) |
| CV % | | 34.06 | 35.78 |
| $t_{max}$ (h) | Day 7 | | |
| N | | 16 | 16 |
| Median | | 1.75 | 2.00 |
| MM, Max | | 1.00, 3.00 | 1.00, 3.03 |
| Mean (SD) | | 1.88 (0.65) | 2.31 (0.68) |
| CV % | | 34.43 | 29.48 |
| $AUC_{0-24}$ (h*ng/mL) | Day 1 | | |
| N | | 18 | 18 |
| Mean (SD) | | 2214.7 (788.1) | 2343.3 (761.6) |

TABLE 14-continued

Summary of Plasma for Crystalline Form II of Compound (I) Pharmacokinetic Parameters by Gender and Day for All Crystalline Form II Of Compound (I) Doses Pooled

| PK Parameter Statistic | Study Day | Gender | |
|---|---|---|---|
| | | Males | Females |
| Min, Max | | 1412.4, 4265.5 | 1322.6, 4099.3 |
| CV % | | 35.58 | 32.50 |
| AUC$_{0-24}$ (h*ng/mL) | Day 7 | | |
| N | | 16 | 16 |
| Mean (SD) | | 3749.3 (1388.3) | 4472.9 (1570.0) |
| Min, Max | | 2543.3, 7364.8 | 2107.3, 7880.0 |
| CV % | | 37.03 | 35.10 |
| AUC$_{last}$ (h*ng/mL) | Day 1 | | |
| N | | 18 | 18 |
| Mean (SD) | | 2190.3 (778.5) | 2312.5 (749.4) |
| Min, Max | | 1392.7, 4206.0 | 1308.2, 4054.0 |
| CV % | | 35.54 | 32.41 |
| AUC$_{last}$ (h*ng/mL) | Day 7 | | |
| N | | 16 | 16 |
| Mean (SD) | | 6353.6 (2692.0) | 8582.7 (3497.9) |
| Min, Max | | 2534.3, 12849.0 | 3103.4, 14653.4 |
| CV % | | 42.37 | 40.76 |
| AUC$_{inf}$ (h*ng/mL) | Day 7 | | |
| N | | 16 | 16 |
| Mean (SD) | | 6767.1 (2890.3) | 9319.7 (4031.5) |
| Min, Max | | 3187.2, 13362.2 | 3201.4, 16659.1 |
| CV % | | 42.71 | 43.26 |
| AUC$_{\%extrap}$ (%) | Day 7 | | |
| N | | 16 | 16 |
| Mean (SD) | | 6.06 (5.38) | 6.76 (4.26) |
| Min, Max | | 0.93, 20.48 | 1.38, 16.86 |
| CV % | | 88.81 | 62.97 |
| CL/F (L/h) | Day 1 | | |
| N | | 18 | 18 |
| Mean (SD) | | 6.19 (1.15) | 5.79 (0.84) |
| Min, Max | | 4.67, 8.50 | 4.59, 7.28 |
| CV % | | 18.58 | 14.53 |
| CL/F (L/h) | Day 7 | | |
| N | | 16 | 16 |
| Mean (SD) | | 3.74 (0.83) | 3.19 (0.84) |
| Min, Max | | 2.72, 5.53 | 2.01, 4.89 |
| CV % | | 22.09 | 26.17 |
| V$_z$/F (L) | Day 1 | | |
| N | | 18 | 18 |
| Mean (SD) | | 147.17 (70.09) | 181.51 (79.11) |
| Min, Max | | 60.75, 341.22 | 83.53, 376.03 |
| CV % | | 47.62 | 43.59 |
| V$_{ss}$/F (L) | Day 7 | | |
| N | | 16 | 16 |
| Mean (SD) | | 107.79 (32.05) | 105.19 (26.24) |
| Min, Max | | 49.78, 160.37 | 76.51, 182.39 |
| CV % | | 29.73 | 24.95 |
| t$_{1/2}$, (h) | Day 7 | | |
| N | | 16 | 16 |
| Mean (SD) | | 20.57 (6.87) | 23.84 (6.58) |
| Min, Max | | 10.93, 37.88 | 14.12, 37.50 |
| CV % | | 33.42 | 27.61 |
| Dose-Normalized C$_{max}$ (ng/mL/mg) | Day 1 | | |
| N | | 18 | 18 |
| Mean (SD) | | 19.78 (3.09) | 20.59 (2.86) |
| Min, Max | | 14.50, 26.75 | 16.50, 28.75 |
| CV % | | 15.62 | 13.89 |
| Dose-Normalized C$_{max}$ (ng/mL/mg) | Day 7 | | |
| N | | 16 | 16 |
| Mean (SD) | | 26.21 (3.94) | 27.98 (5.43) |
| Min, Max | | 19.67, 32.50 | 18.25, 36.00 |
| CV % | | 15.04 | 19.42 |
| Dose-Normalized AUC$_{inf}$ (h*ng/mL/mg) | Day 7 | | |
| N | | 16 | 16 |
| Mean (SD) | | 512.15 (188.98) | 698.59 (282.19) |
| Min, Max | | 230.76, 937.07 | 331.55, 1388.25 |
| CV % | | 36.90 | 40.39 |
| Observed Accumulation Index | | | |
| N | | 16 | 16 |
| Mean (SD) | | 1.72 (0.28) | 1.88 (0.37) |
| Min, Max | | 1.26, 2.34 | 1.36, 2.41 |
| CV % | | 16.08 | 19.60 |
| Steady State Accumulation Index | | | |
| N | | 16 | 16 |
| Mean (SD) | | 1.15 (0.16) | 1.10 (0.15) |
| Min, Max | | 0.93, 1.46 | 0.80, 1.41 |
| CV % | | 13.91 | 13.88 |
| Day 7/Day 1 C$_{max}$ Ratio | | | |
| N | | 16 | 16 |
| Mean (SD) | | 1.36 (0.22) | 1.38 (0.27) |
| Min, Max | | 1.06, 2.00 | 0.95, 1.83 |
| CV % | | 16.44 | 19.28 |

Effects of Crystalline Form II of Compound (I) on arterial blood pressure are as follows. Briefly, the average 24 hour and daytime systolic blood pressure (SBP) and diastolic blood pressure (DBP) increased with all Crystalline Form II of Compound (I) doses compared to placebo, with the maximal increases in BP being observed by Day 4, except for the Crystalline Form II of Compound (I) 20 mg dose which increased further from Day 4 to Day 7. The effects of Crystalline Form II of Compound (I) on average nighttime SBP and DBP were smaller and less consistently observed. The effects of Crystalline Form II of Compound (I) on blood pressure appeared similar regardless of age subgroup. The effect of Crystalline Form II of Compound (I) 20 mg on SBP appeared slightly more pronounced in females compared to males on Day 7, however, overall, the BP effects of Crystalline Form II of Compound (I) appeared similar in males and females.

There was a high degree of variability in the plasma BDNF measurements in this study. However, there appeared to be a trend for an increase on average 7-day BDNF values compared to placebo at the higher two doses of 16 and 20 mg.

Example 21: Antidepressant Effect in Subjects with MDD and Suicidal Ideation

A randomized, double-blind, placebo-controlled, sequential parallel study is conducted to evaluate the antidepressant effect of crystalline Form II of Compound (I) after 7 days of treatment.

Following a screening period of up to 14 days, approximately 135 subjects (male and female, 18 to 70 years of age with NIDD and experiencing a severe depressive episode with recent active suicidal ideation despite current, stable treatment with an SSRI or SNRI) are randomly assigned to one of three treatment sequences with unequal distribution as shown in Table 15.

TABLE 15

| Treatment Sequence | Period 1 (7 days) | Period 2 (28 days) |
|---|---|---|
| 1 (N = 27) | Crystalline Form II of Compound (I) 12 mg on Day 0 followed by 8 mg on Days 1-6 | Crystalline Form II of Compound (I) 8 mg on Days 7-27 followed by placebo on Days 28-34 |
| 2 (N = 54) | Placebo on Days 0-6 | Crystalline Form II of Compound (I) (8 mg) on Days 7-34 |
| 3 (N = 54) | Placebo on Days 0-6 | Placebo on Days 7-34 |

The randomized subjects participate in two treatment periods (Period 1 and Period 2) and a follow-up safety assessment. In Period 1, the subjects receive their first dose of study drug and undergo safety, PK and efficacy assessments on Day 0. On Day 4 (±1 day), the subjects undergo pre-dose safety, PK and efficacy assessments, followed by dosing procedures and post-dose safety and efficacy assessments. On Day 7 (±1 day), the subjects undergo safety, PK and efficacy assessments, thereby completing Period 1. Upon completion of Period 1 study assessments, the subjects receive their first dose of Period 2 study drug on that same day (Day 7±1 day) and undergo post-dose safety and efficacy assessments. On Days 11, 14, 21 and 28 (±1 day), the subjects undergo pre-dose safety, PK and efficacy assessments, followed by dosing procedures and post-dose safety and efficacy assessments. On Day 35 (±1 day), the subjects undergo safety, PK and efficacy assessments, thereby concluding Period 2. On Day 49 (±2 days), the subjects undergo follow-up safety assessments.

Efficacy is assessed based on the following:
NIDD: HAM-D17, Clinical Global Impression-Severity (CGI-S), and Clinical Global Impression-Improvement (CGI-I);
suicidality: Beck Scale for Suicide Ideation (BSSI);
biomarker: plasma BDNF; and
genotype: BDNF polymorphism.

Safety is assessed based on the following:
vital signs (semi-recumbent blood pressure, heart rate and oral body temperature);
blood pressure measurements performed in triplicate (within 5 minutes) at each time point and the average determined;
12-lead electrocardiogram (ECG);
clinical laboratory testing (hematology, clinical chemistry and urinalysis)
physical examinations
adverse event (AE) assessments
Columbia-Suicide Severity Rating Scale (C-SSRS, "Baseline/Screening" version and "Since Last Visit" version)
Brief Psychiatric Rating Scale (BPRS)
concomitant medication assessments Safety, PK and efficacy data (e.g., changes from baseline in HAM-D17, duration of HAM-D17 response, time to meet HAM-D17 responder criterion (≥50% decrease from baseline), BSSI scores and changes from baseline, BDNF levels and changes from baseline, CGI-S and CGI-I scores, blood pressure and changes from baseline, and trough concentrations of crystalline Form II of Compound (I)) are assessed to evaluate the antidepressant effect of crystalline Form II of Compound (I), as well as its safety and tolerability as an adjunctive treatment in subjects with MDD, its effect as adjunctive therapy on suicidal ideation, its effects on specific depressive symptoms, its effects on plasma BDNF, the need for a loading dose, the relationship between onset of antidepressant effect and plasma BDNF in subjects with MDD, the relationship between baseline symptoms and rate and magnitude of response in subjects with MDD, and differences of antidepressant effect in subjects with BDNF Val66Val vs. Val66Met polymorphism.

Example 22: Antidepressant Effect in Subjects with MDD

A randomized, double-blind, placebo-controlled, sequential parallel study is conducted to evaluate the antidepressant effect of a single dose of crystalline Form II of Compound (I) after a single dose of treatment.

Following a screening period of up to 14 days, approximately 60 subjects (male and female, 18 to 65 years of age, diagnosed with MDD without psychotic features, and undergoing stable treatment with an SSRI or SNRI) are randomly assigned to one of three treatment sequences with unequal distribution as shown in Table 16.

TABLE 16

| Treatment Sequence | Period 1 Study Drug | Period 2 Study Drug |
|---|---|---|
| 1 (N = 10) | Crystalline Form II of Compound (I) (20 mg) on Day 0 | Crystalline Form II of Compound (I) (20 mg) on Day 3 |
| 2 (N = 25) | Placebo on Day 0 | Crystalline Form II of Compound (I) (20 mg) on Day 3 |
| 3 (N = 25) | Placebo on Day 0 | Placebo on Day 3 |

The randomized subjects participate in two treatment periods (Period 1 and Period 2) and follow-up safety and efficacy assessments. On Day 0 of Period 1, the subjects undergo baseline assessments, receive their Period 1 study drug, and undergo post-dose safety, PK and efficacy assessments. On Day 1 of Period 1, the subjects undergo additional safety, PK and efficacy assessments, after which the subjects are re-randomized into Period 2 treatment sequences. On Day 3 of Period 2, the subjects undergo baseline assessments, receive their Period 2 study drug, and undergo post-dose safety, PK and efficacy assessments. On Day 4 of Period 2, the subjects undergo additional safety, PK and efficacy assessments. Following Period 2, the subjects undergo follow-up safety and efficacy assessments on Day 6, Day 10 (±1 day), and Day 17 (±1 day).

Safety, PK and efficacy data are assessed to evaluate the antidepressant effect of a single dose of crystalline Form II of Compound (I), as well as its safety and tolerability as an adjunctive treatment in subjects with MDD, its effects on specific depressive symptoms, the relationship between antidepressant effect and plasma BDNF in subjects with MDD, the relationship between baseline symptoms and rate and magnitude of response in subjects with MDD, and differences of antidepressant effect in subjects with BDNF Val66Val vs. Val66Met polymorphism.

Example 23: Study of the Hemodynamic Effects of Compound (I)

Figure 11:
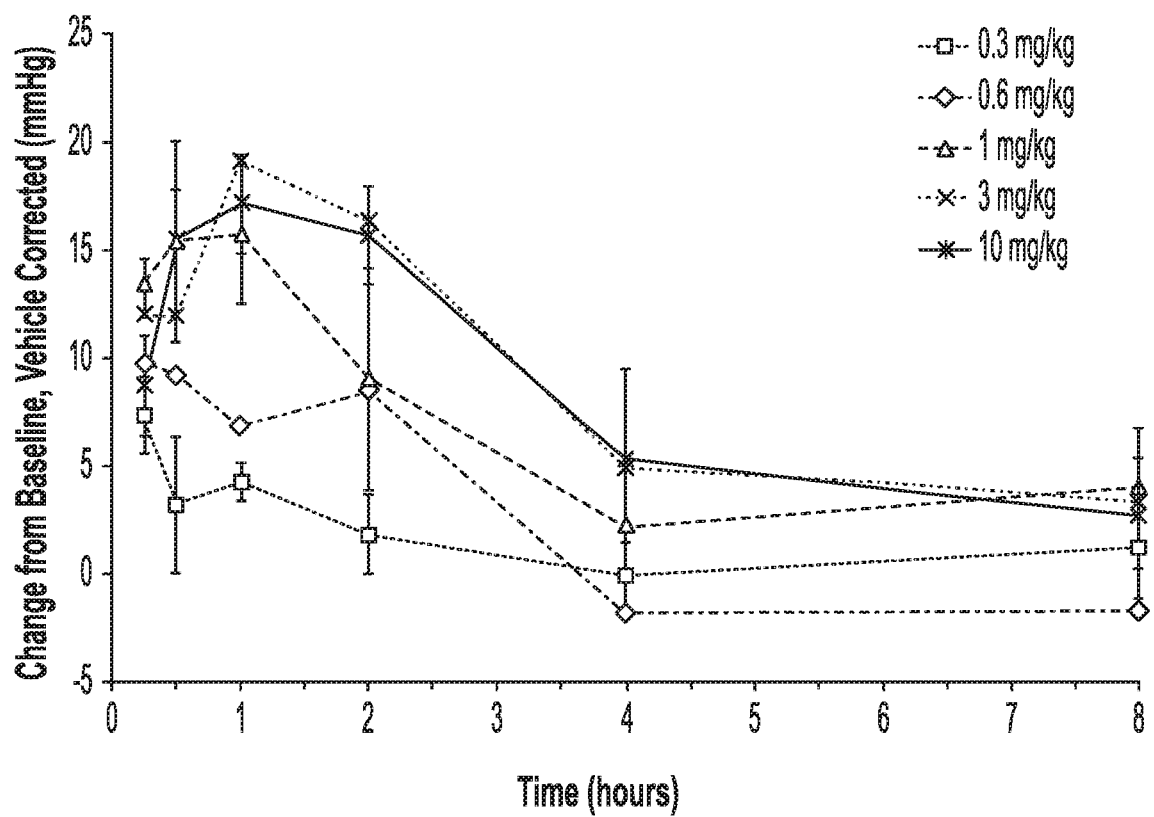
FIG. 11 shows effects of a single oral dose of Compound (I) on systolic blood pressure.

To determine its systemic hemodynamic effects, Compound (I) was administered as a single oral gavage dose to six (n=6) chronically telemetered rats (implantation at least 7 days prior to the dosing day) at doses of 0.3, 0.6, 1, 3, and 10 mg/kg and systemic blood pressure and heart rate values were recorded (FIG. 11). The hemodynamic effects were compared to Dizocilpine (MK-801) at a dose of 0.2 mg/kg given intravenously (in 0.9% saline). In each animal, a single oral gavage dose of Compound (I) or vehicle (0.5% MC/0.02% SLS) was administered (volume: 5 mL/kg). A 24-hour recording was performed prior to dosing (vehicle alone) and after each oral dose. In another set of studies, Compound (I) (1 mg/kg) was administered in combination with the α1-adrenergic receptor antagonist prazosin (al-adrenergic receptor antagonist, 200 µg/kg, IV bolus) to elucidate the underlying mechanism of hypertension. Data were analyzed and compared to baseline, with correction for 24-h predose vehicle control.

The studies in conscious telemetered rats demonstrate that Compound (I), when given orally, increased arterial blood pressure transiently, and in a dose-dependent manner between 0.3-1 mg/kg, and this effect plateaued at 1-10 mg/kg. Interestingly, the ED50 for blood pressure effects was similar to ED50 for the forced swim test. The magnitude of change in hemodynamics with Compound (I) was significantly less than that of MK-801, a broad NMDA receptor antagonist. In addition, Compound (I) modestly increased heart rate at 0.3 and 0.6 mg/kg doses, and increased HR dose proportionally between 1 and 10 mg/kg. Further, a strong correlation between locomotor activity level and change in heart rate was observed ($R^2$=0.67). The changes in heart rate may be partially explained by the central nervous system excitatory effects of Compound (I). Similar dose-dependent movement effects (dose proportional between 1 and 10 mg/kg) were also observed in a study of the locomotor effects of Compound (I) in rats.

Figure 12:
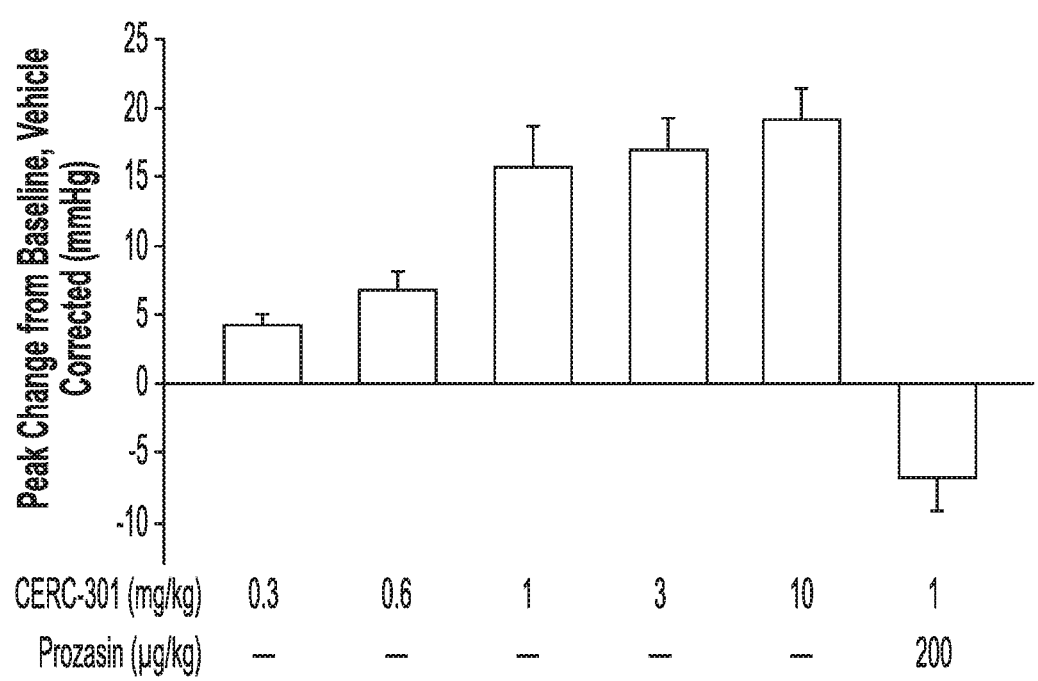
FIG. 12 shows effects of a single oral dose of Compound (I) on systolic blood pressure, with or without prazosin.

As shown in FIG. 12, the effects of a single oral dose of Compound (I) on systolic blood pressure, with or without prazosin, were also investigated. This study demonstrated that α1-adernergic blockade provided protection from Compound (I) mediated increases in blood pressure. Alpha-adrenoceptors predominate in the innervation of the vascular smooth muscle causing vasoconstriction and increases in afterload. The sympathetic nervous system's adrenergic neurotransmitter, norepinephrine, produces its vascular effects by binding to these adrenoceptors in the vasculature. The administration of agents that blocked peripheral α1-adrenergic receptors, such as the prazosin quinazoline compounds, effectively blocked and can be used to treat the blood pressure effects of Compound (I). Further, in human studies of Compound (I) administered orally at doses up to 20 mg, the primary hemodynamic observation has been a transient increase in systolic and diastolic blood pressure, with a maximum and minimum that tends to correlate with TMAX and redistribution time. Heart rates have not been observed to increase to any significant degree, either clinically or statistically. Blood pressure increases in the absence of heart rate increases suggests a vasoconstrictive effect of Compound (I) ($\alpha_1$-adrenergic activity) with limited effects on cardiac contractility or inotropy (little to no $\beta_1$-adrenergic effect). Increases in tone of the $\alpha_1$-adrenergic system in animals and humans, induced either directly with $\alpha_1$-agonists, or indirectly with drugs that increase norepinephrine activity, can be easily and safely counteracted by agents that block $\alpha_1$-adrenergic receptors in the vasculature, or $\alpha_1$-adrenergic blockers.

Figure 13:
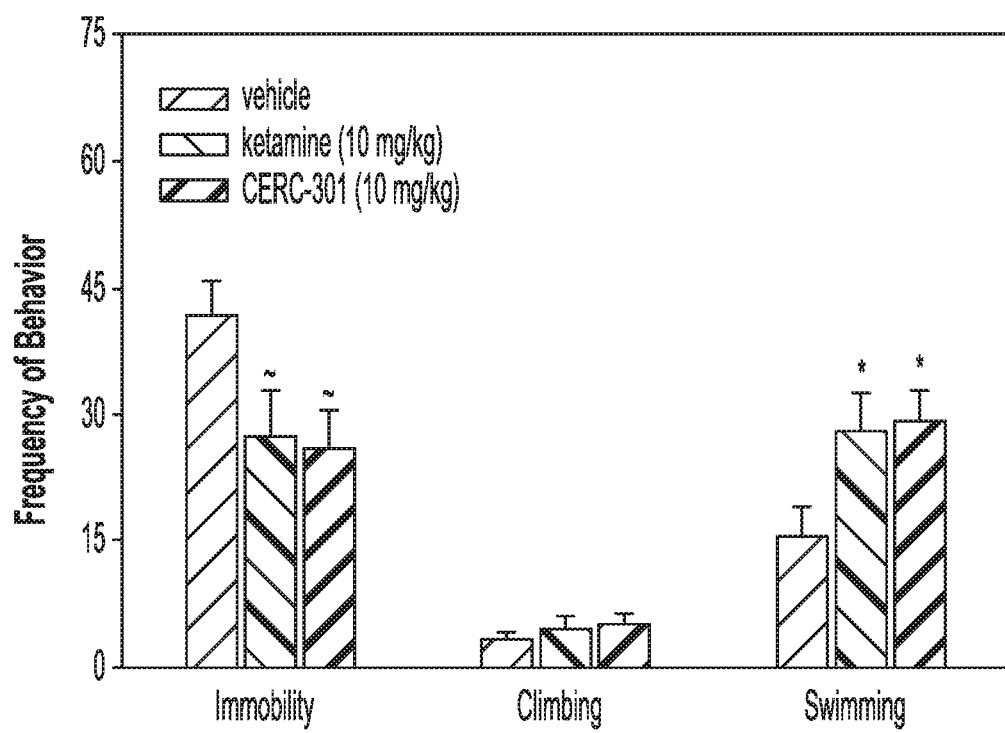
FIG. 13 shows the effect of Compound (I) and ketamine on behaviors in the rat forced swim test 24 hours after administration (*p<0.05 compare to vehicle group ~p>0.05).

Example 24: Effect of Compound (1) and Ketamine on Behaviors in the Rat Forced Swim Test 24 Hours after Administration This study aimed to evaluate the duration of the antidepressant-like effects of Form II of Compound (I) using the forced swim test in male, Sprague-Dawley rats. Clinically effective antidepressant compounds reduce immobility time and increase swimming in rodents subjected to this test. Rats received Compound (I) (10 mg/kg, p.o.) or ketamine (10 mg/kg, i.p.) and 24 hours later were subjected to testing. As shown in FIG. 13, both ketamine and Form II of Compound (I) reduced immobility and increased swim time significantly in this behavioral procedure (p<0.05). The data represent mean±SEM. Similar to ketamine, these data are consistent with a long lasting antidepressant-like effect of Compound (I).

Example 25: Preparation of Tablets

Step 1: Preparation for Roller Compaction
Dispensing and De-Lumping:
 1. The following components were dispensed into individual containers:
    a. Microcrystalline cellulose (Avicel® PH 102)
    b. Lactose monohydrate (310)
    c. Croscarmellose sodium (Ac-Di-Sol®)
    d. Magnesium stearate (Hyqual®; vegetable source)
    e. Crystalline Form II of Compound (I)
 2. All ingredients except magnesium stearate were de-lumped through a 20 mesh hand screen. Magnesium stearate was de-lumped through a 60 mesh hand screen.
Blending and Pre-Roller Compaction Lubrication:
 1. The ingredients were loaded in the v-blender in the following order:
    a. Approximately half of microcrystalline cellulose
    b. Crystalline Form II of Compound (I)
    c. Remaining half of microcrystalline cellulose
    d. Materials were blended for 8.5 min at 30 rpm.
 2. Croscarmellose sodium was then added, followed by lactose monohydrate and blended for 17 min at 30 rpm.
 3. Magnesium stearate was added to the v-blender and blended for an additional 4.5 min at 30 rpm.
 4. The blend was discharged in a low-density polyethylene (LDPE) bags.

Step 2: Preparation of Roller Compaction Granules
Roller Compaction:
 1. The blend was manually loaded into the hopper. Feeder screw and roller compactor parameters were adjusted to yield a ribbon of the desired density. The parameters were recorded at a preset time interval.
 2. The ribbons were collected in a double LDPE bags.
 3. Ribbon Reconciliation. The ribbon thickness, weight, and length to yield ribbon density were evaluated.
Milling
The collected ribbons were milled at 800±300 rpm through a Comil fitted with a round hole (diameter, 0.039") and a round impeller.
Post Roller Compaction Lubrication
The granules were loaded in the v-blender followed by de-lumped magnesium stearate and blended for a 4.5 min at 30 rpm.

Step 3: Preparation of Finished Tablets
Tableting
The blend was manually charged into the hopper. The die fill amount and compression parameters (press speed, fill depth, pre-compression thickness setting, compression thickness setting, and force feeder speed) were adjusted to yield a tablet with the target weight and hardness. All finished tablets were collected in a double LDPE bags.

The composition of the tablets is provided in Table 17.

TABLE 17

Composition of Tablets

| Component | Function | Strength (label claim) 4 mg | |
|---|---|---|---|
| | | Qty per tablet (mg) | % w/w |
| Crystalline Form II of Compound (I) | Active Ingredient | 4.0 | 5.0 |
| Microcrystalline Cellulose (Avicel ® PH 102) | Diluent | 36.8 | 46.0 |
| Lactose Monohydrate 310 | Diluent | 36.8 | 46.0 |
| Croscarmellose Sodium (Ac-Di-Sol ®) | Disintegrant | 1.6 | 2.0 |
| Magnesium Stearate (Hyqual ®; vegetable source) | Lubricant | 0.8 | 1.0 |
| Total Weight per Tablet (mg) | | 80 | 100 |

SPECIFIC EMBODIMENTS

1. A compound which is substantially pure crystalline Form II of Compound (I)

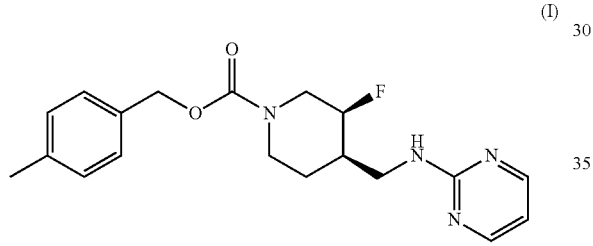

(I)

exhibiting at least one of:
  (i) an X-ray powder diffraction pattern, obtained using copper Kα radiation, comprising peaks of 2-theta angle of about 5.9 and 8.8 degrees;
  (ii) an X-ray powder diffraction pattern, obtained using copper Kα radiation, substantially as shown in FIG. 1A;
  (iii) an ultraviolet absorbance spectrum, obtained using methanol as diluent, substantially as shown in FIG. 2;
  (iv) an infrared spectrum substantially as shown in FIG. 3;
  (v) a proton nuclear magnetic resonance spectrum at about 600 MHz in $CD_3CN$ substantially as shown in FIG. 4;
  (vi) a $^{13}C$ nuclear magnetic resonance spectrum at about 150 MHz in $CD_3CN$ substantially as shown in FIG. 5;
  (vii) a thermogravimetric analysis curve substantially as shown in FIG. 6; and
  (viii) a differential scanning calorimetry thermogram substantially as shown in FIG. 7.

2. The compound of embodiment 1, wherein the compound exhibits an X-ray powder diffraction pattern comprising peaks of 2-theta angles of about 5.9 and 8.8 degrees which correspond, respectively, to d-spacing at about 14.9 and 10.0 Angstroms (Å).

3. The compound of embodiment 1 or 2, wherein the compound exhibits an X-ray powder diffraction pattern substantially as shown in FIG. 1A.

4. The compound of any one of embodiments 2 and 3, wherein the compound further exhibits at least one of: an ultraviolet absorbance spectrum substantially as shown in FIG. 2, an infrared spectrum substantially as shown in FIG. 3, a proton nuclear magnetic resonance spectrum substantially as shown in FIG. 4, a $^{13}C$ nuclear magnetic resonance spectrum substantially as shown in FIG. 5, a thermogravimetric analysis curve substantially as shown in FIG. 6, and a differential scanning calorimetry thermogram substantially as shown in FIG. 7.

5. The compound of any one of embodiments 1-4, wherein the compound exhibits an ultraviolet absorbance spectrum substantially as shown in FIG. 2.

6. The compound of embodiment 5, wherein the ultraviolet absorbance spectrum comprises an absorbance maximum at about 236±2 nm.

7. The compound of any one of embodiments 1-4, wherein the compound exhibits an infrared spectrum substantially as shown in FIG. 3.

8. The compound of any one of embodiments 1-4, wherein the compound exhibits a proton nuclear magnetic resonance spectrum substantially as shown in FIG. 4.

9. The compound of embodiment 8, wherein the proton nuclear magnetic resonance spectrum comprises peaks substantially as set out in Table 1.

10. The compound of any one of embodiments 1-4, wherein the compound exhibits a $^{13}C$ nuclear magnetic resonance spectrum comprises peaks substantially as shown in FIG. 5.

11. The compound of embodiment 10, wherein the $^{13}C$ nuclear magnetic resonance spectrum comprises peaks substantially as set out in Table 2.

12. The compound of any one of embodiments 1-4, wherein the compound exhibits a thermogravimetric analysis curve substantially as shown in FIG. 6.

13. The compound of embodiment 12, wherein the thermogravimetric analysis curve corresponds to a weight loss of about 0.16% up to about 250° C.

14. The compound of any one of embodiments 1-4, wherein the compound exhibits a differential scanning calorimetry thermogram substantially as shown in FIG. 7.

15. The compound of embodiment 14, wherein the differential scanning calorimetry thermogram comprises an endothermic peak at a temperature of about 124° C.

16. A pharmaceutical composition comprising an effective amount of the compound of any one of embodiments 1-15.

17. The pharmaceutical composition of embodiment 16, further comprising a pharmaceutically acceptable excipient.

18. A pharmaceutical composition of any one of embodiments 16 and 17, wherein the Compound (I) is in particulate form with an X90 particle size of about 10 μm or less.

19. The pharmaceutical composition of embodiment 18, wherein the X90 particle size is about 8 μm or less.

20. The pharmaceutical composition of embodiment 18, wherein the X90 particle size is about 6 μm or less.

21. The pharmaceutical composition of embodiment 18, wherein the X90 particle size is about 5 μm or less.

22. The pharmaceutical composition of embodiment 18, wherein the X90 particle size is between about 1 μm and about 10 μm.
23. The pharmaceutical composition of embodiment 18, wherein the X90 particle size is between about 2 μm and about 8 μm.
24. The pharmaceutical composition of embodiment 18, wherein the X90 particle size is between about 3 μm and about 6 μm.
25. The pharmaceutical composition of embodiment 18, wherein the X90 particle size is between about 4 μm and about 5 μm.
26. The pharmaceutical composition of embodiment 18, wherein the X90 particle size is about 4.5 μm.
27. The pharmaceutical composition of any one of embodiments 16-26, wherein the pharmaceutical composition is formulated for oral administration.
28. The pharmaceutical composition of embodiment 27, wherein the pharmaceutical composition is in tablet or capsule form.
29. A method of treating a condition responsive to an NR2B antagonist, comprising administering to a patient in need thereof an effective amount of a compound of any one of embodiments 1-15 or a pharmaceutical composition of any one of embodiments 16-28.
30. The method of embodiment 29, wherein the condition is a depressive disorder.
31. The method of embodiment 29, wherein the condition is major depressive disorder.
32. The method of embodiment 29, wherein the condition is treatment-resistant major depressive disorder.
33. The method of any one of embodiments 29-32, wherein the compound is administered as an adjunct to a serotonin reuptake inhibitor or a serotonin and norepinephrine reuptake inhibitor.
34. The method of any one of embodiments 29-33, wherein the compound is administered intermittently.
35. The method of any one of embodiments 29-34, wherein the effective amount is between about 4 mg and about 60 mg daily or intermittently.
36. The method of any one of embodiments 29-35 where the compound is administered without food.
37. The method of any one of embodiments 29-35 wherein the compound is administered with food.
38. A pharmaceutical composition comprising particles of Compound (I)

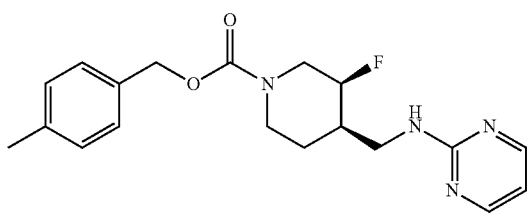

(I)

with an X90 particle size of about 10 μm or less.
39. The pharmaceutical composition of embodiment 38, wherein the X90 particle size is about 8 μm or less.
40. The pharmaceutical composition of embodiment 38, wherein the X90 particle size is about 6 μm or less.
41. The pharmaceutical composition of embodiment 38, wherein the X90 particle size is about 5 μm or less.
42. The pharmaceutical composition of embodiment 38, wherein the X90 particle size is between about 1 μm and about 10 μm.
43. The pharmaceutical composition of embodiment 38, wherein the X90 particle size is between about 2 μm and about 8 μm.
44. The pharmaceutical composition of embodiment 38, wherein the X90 particle size is between about 3 μm and about 6 μm.
45. The pharmaceutical composition of embodiment 38, wherein the X90 particle size is between about 4 μm and about 5 μm.
46. The pharmaceutical composition of embodiment 38, wherein the X90 particle size is about 4.5 μM.
47. The pharmaceutical composition of any one of embodiments 38-46, further comprising a pharmaceutically acceptable excipient.
48. The pharmaceutical composition of any one of embodiments 38-47, wherein the pharmaceutical composition is formulated for oral administration.
49. The pharmaceutical composition of any one of embodiments 38-47, wherein the pharmaceutical composition is in the form of a tablet or capsule.
50. The pharmaceutical composition of any one of embodiments 38-49, wherein the Compound (I) is in crystalline Form II as characterized in any one of embodiments 1-15.
51. A method of increasing bioavailability of Compound (I)

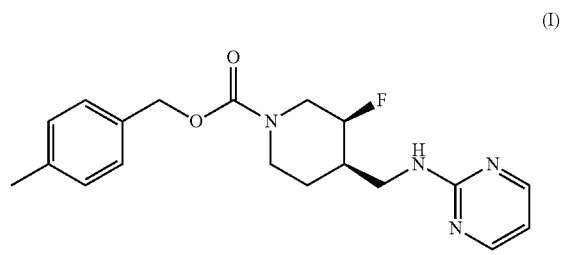 [SMILES: Cc1ccc(COC(=O)N2CC[C@H](CNc3ncccn3)[C@H](F)C2)cc1]

(I)

comprising administering to a patient in need thereof an effective amount of a pharmaceutical composition of any one of embodiments 38-50.
52. The method of embodiment 51, wherein the method results in a higher area under the curve compared to that of a method comprising administering Compound (I) with an X90 particle size of about 10 μm or higher.
53. The method of embodiment 51, wherein the method results in a higher area under the curve compared to that of a method comprising administering Compound (I) with an X90 particle size of about 11 μm or higher.
54. The method of embodiment 51, wherein the method results in a higher area under the curve compared to that of a method comprising administering Compound (I) with an X90 particle size of about 12 μm or higher.
55. The method of embodiment 51, wherein the method results in a higher area under the curve compared to that of a method comprising administering Compound (I) with an X90 particle size of about 13 μm or higher.
56. The method of embodiment 51, wherein the method results in a higher area under the curve compared to that of a method comprising administering Compound (I) with an X90 particle size of about 14 μm or higher.
57. A method of treating a condition responsive to an NR2B antagonist, comprising administering to a patient in need thereof an effective amount of a pharmaceutical composition of any one of embodiments 38-50.
58. The method of embodiment 57, wherein the condition is a depressive disorder.
59. The method of embodiment 57, wherein the condition is major depressive disorder.

60. The method of embodiment 57, wherein the condition is treatment-resistant major depressive disorder.
61. The method of any one of embodiments 57-60, wherein the compound is administered as an adjunct to a serotonin reuptake inhibitor or a serotonin and norepinephrine reuptake inhibitor.
62. A method of treating suicidal ideation, comprising administering an effective amount of Compound (I)

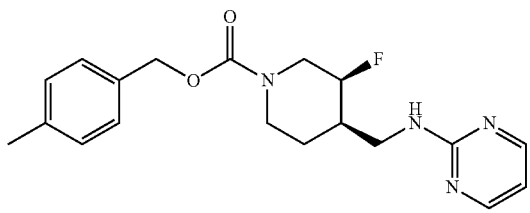

(I)

to a patient who has, is suspected of having, or has been diagnosed with having suicidal ideation.
63. The method of embodiment 62, wherein the patient has been diagnosed with having suicidal ideation within about 4 weeks prior to administration of the compound.
64. The method of any one of embodiments 62 and 63, wherein the patient has been further diagnosed with having a depressive disorder.
65. The method of any one of embodiments 62 and 63, wherein the patient has been further diagnosed with having major depressive disorder.
66. The method of any one of embodiments 62 and 63, wherein the patient has been further diagnosed with having treatment-resistant major depressive disorder.
67. The method of any one of embodiments 62-66, wherein the Compound (I) is in crystalline Form II as characterized in any one of embodiments 1-15.
68. The method of any one of embodiments 62-67, wherein the Compound (I) is in a pharmaceutical composition as characterized in any one of embodiments 38-50.
69. The method of any one of embodiments 51-68, wherein the Compound (I) or pharmaceutical composition is administered without food.
70. The method of any one of embodiments 51-68, wherein the Compound (I) or pharmaceutical composition is administered with food.
71. A method of reducing absorption rate of Compound (I)

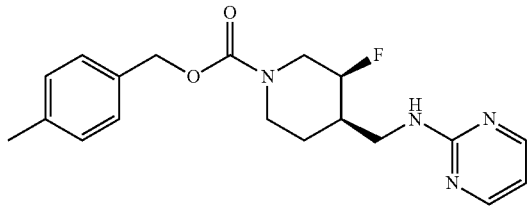

(I)

comprising administering to a patient in need thereof an effective amount of the Compound (I) with food, wherein the compound is administered either substantially concurrently with, or up to about 2 hours after, or up to about 30 minutes before administration of food.
72. The method of embodiment 71, wherein the method results in a lower $C_{max}$ or a higher $T_{max}$ compared to that of a method comprising administering the Compound (I) without food.
73. The method of any one of embodiments 71 and 72, wherein the Compound (I) is administered either substantially concurrently with, or up to about 90 minutes after, or up to about 15 minutes before administration of food.
74. The method of any one of embodiments 71 and 72, wherein the Compound (I) is administered either substantially concurrently with, or up to about 60 minutes after, or up to about 10 minutes before administration of food.
75. The method of any one of embodiments 71 and 72, wherein the Compound (I) is administered substantially concurrently with administration of food.
76. The method of any one of embodiments 71-75, wherein the compound is administered orally.
77. The method of any one of embodiments 71-76, wherein the compound is in crystalline Form II as characterized in any one of embodiments 1-15.
78. The method of any one of embodiments 71-77, wherein the compound is in a pharmaceutical composition as characterized in any one of embodiments 38-50.
79. The method of any one of embodiments 51-78, wherein the effective amount is between about 4 mg and about 60 mg daily or intermittently.
80. The method of any one of embodiments 29-37 and 51-79, further comprising monitoring the patient's blood pressure; and if hypertension is detected, administering an anti-hypertensive to the patient.
81. A method of preparing Compound (I)

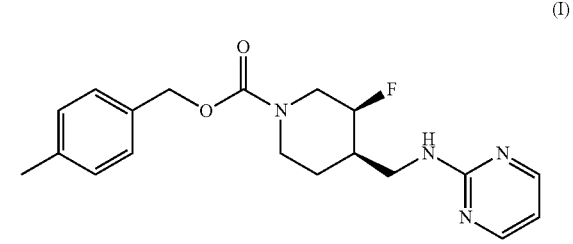 [SMILES: Cc1ccc(COC(=O)N2CC[C@H](CNc3ncccn3)[C@H](F)C2)cc1]

(I)

comprising:
(i) reacting Compound (8)

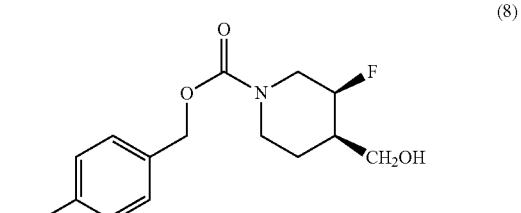

(8)

with triflic anhydride to yield a triflate;
(ii) reacting the triflate with ammonia to yield Compound (9)

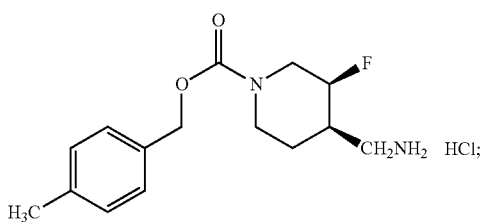

and (iii) reacting the Compound (9) with 2-chloropyrimidine to yield Form I of Compound (I).

82. The method of embodiment 81, further comprising seeding Form I of Compound (I) with Form II of Compound (I).

83. The method of embodiment 81 or 82, further comprising reacting Compound (6)

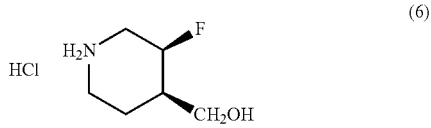

with carbonyldiimidazole and Compound (7)

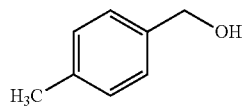

to yield Compound (8).

84. The method of embodiment 82, further comprising debenzylating Compound (5)

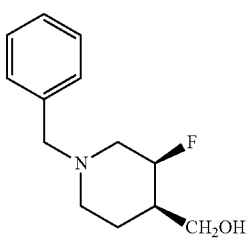

with hydrogen over palladium to yield Compound (6).

85. The method of embodiment 84, further comprising reducing Compound (4)

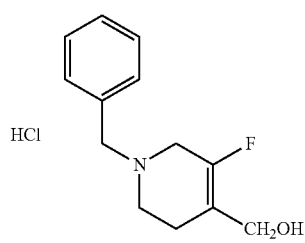

with chloro(1,5-cyclooctadiene)rhodium (I) dimer under hydrogen atmosphere to yield Compound (5).

86. The method of any one of embodiments 81-85, further comprising purifying the Compound (I).

87. The method of embodiment 86, wherein the purifying comprises slurrying or recrystallization.

88. The method of embodiment 85, wherein the purifying comprises slurrying followed by recrystallization.

It will be apparent to those in the art that specific embodiments of the disclosed subject matter may be directed to one or more of the above- and below-indicated embodiments in any combination.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:

1. A method of treating a condition responsive to an NR2B antagonist, comprising administering to a patient in need thereof an effective amount of crystalline Form II of Compound (I)

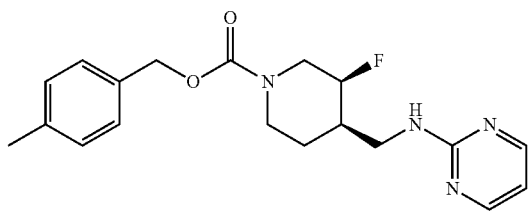

exhibiting at least one of:

(a) an X-ray powder diffraction pattern, obtained using copper Kα radiation, comprising a peak of 2-theta angle of about 5.9 degree;

(b) an infrared spectrum substantially as shown in FIG. 3;

(c) a thermogravimetric analysis curve substantially as shown in FIG. 6; and (d) a differential scanning calorimetry thermogram substantially as shown in FIG. 7.

2. The method of claim 1, wherein the X-ray powder diffraction pattern comprises peaks of 2-theta angles of about 5.9 and 8.8 degrees.

3. The method of claim 1, wherein the X-ray powder diffraction pattern is substantially as shown in FIG. 1A.

4. The method of claim 1, wherein the differential scanning calorimetry thermogram of the compound is substantially as shown in FIG. 7.

5. The method of claim 1, wherein the crystalline Form II of compound I has a purity of at least 95%.

6. The method of claim 1, wherein the condition is selected from Parkinson's disease, neuropathic pain, bone and joint pain, repetitive motion pain, dental pain, cancer pain, myofascial pain, perioperative pain, chronic pain, dysmennorhea, as well as pain associated with angina, and inflammatory pain of varied origins, headache, migraine and cluster headache, schizophrenia, stroke, traumatic brain injury, Alzheimer's disease, cerebral ischemia, amyotrophic lateral sclerosis, Huntington's disease, sensorineural hearing loss, tinnitus, glaucoma, neurological damage caused by epileptic seizures or by neurotoxin poisoning or by impairment of glucose and/or oxygen to the brain, vision loss caused by neurodegeneration of the visual pathway, Restless Leg Syndrome, multi-system atrophy, non-vascular headache, chronic, subchronic or acute cough, primary hyperalgesia, secondary hyperalgesia, primary allodynia, secondary allodynia, or other pain caused by central sensitization, dyskinesias, depressive disorders, trauma- and stressor-related disorders, bipolar disorders with depressive features, anxiety disorders, and obsessive-compulsive and related disorders.

7. The method of claim 1, wherein the condition is major depressive disorder.

8. The method of claim 1, wherein the condition is treatment-resistant major depressive disorder.

9. The method of claim 8, wherein the compound is administered as an adjunct to a serotonin reuptake inhibitor or a serotonin and norepinephrine reuptake inhibitor.

10. The method of claim 7, wherein the compound is administered as an adjunct to a serotonin reuptake inhibitor or a serotonin and norepinephrine reuptake inhibitor.

11. The method of claim 6, wherein the compound is administered as an adjunct to a therapeutic agent selected from the group consisting of: (1) a non-steroidal anti-inflammatory agent; (2) a COX-2 inhibitor; (3) a bradykinin B1 receptor antagonist; (4) a sodium channel blocker and antagonist; (5) a nitric oxide synthase (NOS) inhibitor; (6) a glycine site antagonist; (7) a potassium channel opener; (8) an AMPA/kainate receptor antagonist; (9) a calcium channel antagonist; (10) a GABA-A receptor modulator; (11) a matrix metalloprotease (MMP) inhibitor; (12) a thrombolytic agent; (13) an opioid; (14) a neutrophil inhibitory factor (NIF); (15) L-Dopa; (16) carbidopa; (17) levodopa/carbidopa; (18) a dopamine agonist; (19) an anticholinergic; (20) amantadine; (21) a catechol O-methyltransferase (COMT) inhibitor; (22) a monoamine oxidase B (MAO-B) inhibitor; (23) an opiate agonist or antagonist; (24) a 5HT receptor agonist or antagonist; (25) an NMDA receptor agonist or antagonist; (26) a NK1 antagonist; (27) a selective serotonin reuptake inhibitor (SSRI) and a selective serotonin and norepinephrine reuptake inhibitor (SSNRI); (28) a tricyclic antidepressant, (29) a norepinephrine modulator; (30) lithium; (31) valproate; (32) D-serine; (33) neurontin; (34) an antitussive; (35) an antihistamine; (36) a decongestant; (37) an expectorant; (38) a mucolytic; (39) an antipyretic; and (40) an analgesic.

12. The method of claim 1, wherein the compound is administered as an adjunct to a therapeutic agent selected from the group consisting of: (1) a non-steroidal anti-inflammatory agent; (2) a COX-2 inhibitor; (3) a bradykinin B1 receptor antagonist; (4) a sodium channel blocker and antagonist; (5) a nitric oxide synthase (NOS) inhibitor; (6) a glycine site antagonist; (7) a potassium channel opener; (8) an AMPA/kainate receptor antagonist; (9) a calcium channel antagonist; (10) a GABA-A receptor modulator; (11) a matrix metalloprotease (MMP) inhibitor; (12) a thrombolytic agent; (13) an opioid; (14) a neutrophil inhibitory factor (NIF); (15) L-Dopa; (16) carbidopa; (17) levodopa/carbidopa; (18) a dopamine agonist; (19) an anticholinergic; (20) amantadine; (21) a catechol O-methyltransferase (COMT) inhibitor; (22) a monoamine oxidase B (MAO-B) inhibitor; (23) an opiate agonist or antagonist; (24) a 5HT receptor agonist or antagonist; (25) an NMDA receptor agonist or antagonist; (26) a NK1 antagonist; (27) a selective serotonin reuptake inhibitor (SSRI) and a selective serotonin and norepinephrine reuptake inhibitor (SSNRI); (28) a tricyclic antidepressant, (29) a norepinephrine modulator; (30) lithium; (31) valproate; (32) D-serine; (33) neurontin; (34) an antitussive; (35) an antihistamine; (36) a decongestant; (37) an expectorant; (38) a mucolytic; (39) an antipyretic; and (40) an analgesic.

* * * * *